(12) United States Patent
Wang et al.

(10) Patent No.: US 11,345,703 B2
(45) Date of Patent: May 31, 2022

(54) SUBSTITUTED PYRAZOLO[1,5-A]PYRIMIDINE MACROCYCLIC COMPOUND

(71) Applicant: SHENZHEN TARGETRX, INC., Guangdong (CN)

(72) Inventors: Yihan Wang, Guangdong (CN); Jiuyang Zhao, Guangdong (CN)

(73) Assignee: SHENZHEN TARGETRX, INC., Guangdong (CN)

( * ) Notice: Subject to any disclaimer, the term of this patent is extended or adjusted under 35 U.S.C. 154(b) by 0 days.

(21) Appl. No.: 16/964,069

(22) PCT Filed: Jan. 23, 2019

(86) PCT No.: PCT/CN2019/072833
§ 371 (c)(1),
(2) Date: Jul. 22, 2020

(87) PCT Pub. No.: WO2019/144885
PCT Pub. Date: Aug. 1, 2019

(65) Prior Publication Data
US 2021/0047330 A1     Feb. 18, 2021

(30) Foreign Application Priority Data
Jan. 23, 2018   (CN) .......................... 201810063754.X

(51) Int. Cl.
*C07D 471/22*     (2006.01)
(52) U.S. Cl.
CPC .................................. *C07D 471/22* (2013.01)
(58) Field of Classification Search
CPC ... C07D 491/22; C07D 471/22; A61K 31/519
USPC .......................................... 544/245; 514/251
See application file for complete search history.

(56) References Cited

U.S. PATENT DOCUMENTS

| | | | |
|---|---|---|---|
| 6,221,335 B1 | 4/2001 | Foster | |
| 6,334,997 B1 | 1/2002 | Foster et al. | |
| 6,440,710 B1 | 8/2002 | Keinan et al. | |
| 6,603,008 B1 | 8/2003 | Ando et al. | |
| 7,517,990 B2 | 4/2009 | Ito et al. | |
| 8,513,263 B2 | 8/2013 | Haas et al. | |
| 2007/0082929 A1 | 4/2007 | Gant et al. | |
| 2007/0197695 A1 | 8/2007 | Potyen et al. | |

FOREIGN PATENT DOCUMENTS

| | | | | |
|---|---|---|---|---|
| CN | 102264736 | | 11/2011 | |
| CN | 102971322 | | 3/2013 | |
| CN | 105693720 | | 6/2016 | |
| CN | 106008639 | | 10/2016 | |
| CN | 107428760 | | 12/2017 | |
| EP | 1873157 | | 1/2008 | |
| JP | 2012506446 | | 3/2012 | |
| JP | 2013530142 | | 7/2013 | |
| JP | 2015509535 | | 3/2015 | |
| JP | 2017-503867 A | | 2/2017 | |
| WO | 9526325 | | 10/1995 | |
| WO | 9526325 | | 12/1995 | |
| WO | 2010048314 | | 4/2010 | |
| WO | 2011146336 | | 11/2011 | |
| WO | WO 2011146336 | * | 11/2011 | ........... C07D 487/04 |
| WO | 2015-112806 A2 | | 7/2015 | |
| WO | 2016161572 | | 10/2016 | |
| WO | 2017004342 | | 1/2017 | |
| WO | 2017006953 | | 1/2017 | |
| WO | 2017075107 | | 5/2017 | |
| WO | WO 2017075107 | * | 5/2017 | ......... A61K 31/5025 |

(Continued)

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Chawla et. al.; CRIPS 5(1); 2004; p. 9, col. 2, para. 1.*
Newman et. al.; Drug Discovery Today 8(19); 2003; p. 898, col. 2, Para.3).*
Kushner, et. al., Canadian Journal of Physiology and Pharmacology, Feb. 1999; 77,2.*
Roger Tung, The Development of Deuterium-Containing Drugs (2010).*
Application No. CN201910064063.6 , Office Action, dated Dec. 31, 2019, 7 pages.

(Continued)

*Primary Examiner* — Jeffrey H Murray
(74) *Attorney, Agent, or Firm* — Kilpatrick Townsend & Stockton LLP

(57) ABSTRACT

Provided are a pharmaceutical composition of a substituted pyrazolo[1,5-a]pyrimidine macrocyclic compound and the use thereof. The pyrazolo[1,5-a]pyrimidine macrocyclic compound is a compound as shown in formula (Aa), or a pharmaceutically acceptable salt, a prodrug, a hydrate or a solvate, a crystal form, a stereoisomer or an isotopic variant thereof. The compound of the present invention is an inhibitor of the Trk kinase, and can be used for treating pain, cancers, inflammation, neurodegenerative diseases and certain infectious diseases.

14 Claims, No Drawings

(56) References Cited

FOREIGN PATENT DOCUMENTS

WO         2017176751         10/2017

OTHER PUBLICATIONS

Elvidge et al., "Mechanism Research", Isotope Basic Chemistry and Application, Jan. 31, 1987, pp. 206-207.
Application No. PCT/CN2019/072833, International Search Report and Written Opinion, dated Apr. 22, 2019, 10 pages.
Tsunoda et al., "The Trk Family of Neurotrophin Receptors is Downregulated in the Lumbar Spines of Rats with Congenital Kyphoscoliosis", Molecular and Cellular Biochemistry, vol. 412, No. 1-2, Jan. 2016, 20 pages.
Chinese Application No. CN202010794652.2, Office Action dated Mar. 19, 2021, 8 pages.
Drilon et al, A Next-Generation TRK Kinase Inhibitor Overcomes Acquired Resistance to Prior TRK Kinase Inhibition in Patients with TRK Fusion-Positive Solid Tumors, Cancer Discovery, vol. 7, No. 9, Jun. 3, 2017, pp. 965-966.
Baba et al., Studies on Drug Metabolism by Use of Isotopes. 23. Metabolic Study of L-Butyryl-4-Cinnamylpiperazine in the Rat During Development of Tolerance by Using Two Kinds of Deuterium-labeled Forms, Journal of Medicinal Chemistry, American Chemical Society, vol. 21, No. 6, 1978, pp. 525-529.
European Application No. EP19743399.8, Extended European Search Report dated Apr. 20, 2021, 10 pages.
International Application No. PCT/CN2019/072833, International Preliminary Report on Patentability dated Aug. 6, 2020, 5 pages.
Chinese Application No. 201811550221.0, Complimentary Search Report, dated Mar. 31, 2020, 2 pages.
Chinese Application No. 201811550221.0, Office Action, dated Jan. 20, 2020, 4 pages.
Chinese Application No. 201811550221.0, Office Action, dated Nov. 11, 2019, 9 pages.
Chinese Application No. 201811550221.0, Search Report, dated Oct. 16, 2019, 2 pages.
Chinese Application No. 202010349837.2, Office Action, dated Mar. 24, 2021, 9 pages.
European Application No. 18891153.1, Extended European Search Report, dated Jul. 13, 2021, 9 pages.
Japanese Application No. 2020-534179, Office Action, dated Sep. 14, 2021, 3 pages.
Liu et al., Deuterated Drugs Progress, Pharmaceutical and Chemical, vol. 42, No. 4, Apr. 30, 2016, pp. 199-238.
International Application No. PCT/CN2018/121781, International Preliminary Reporton Patentability, dated Jul. 2, 2020, 5 pages.
International Application No. PCT/CN2018/121781, International Search Report and Written Opinion, dated Mar. 19, 2019, 16 pages.
Office Action in JP2020-540580 dated Sep. 3, 2021, 3 pages.
Amendment filed in JP2013-530142, dated Jun. 26, 2014, 27 pages.
Amendment filed in JP2017-503867, dated Aug. 3, 2018, 15 pages.
Buteau, "Deuterated drugs: unexpectedly nonobvious." J. High Tech. L. 10 (2009): 22.
Foster, "Deuterium isotope effects in the metabolism of drugs and xenobiotics: implications for drug design." Advances in Drug Research 14 (1985): 1-40.
Harbeson et al., "Deuterium in drug discovery and development," Annual Reports in Medicinal Chemistry, vol. 46, Jan. 2011, 403-417.
U.S. Appl. No. 16/956,057, "Non-Final Office Action", dated Feb. 3, 2022, 30 pages.
Browne et al., "Stable Isotope Techniques in Early Drug Development: An Economic Evaluation", Journal of Clinical Pharmacology, vol. 38, Mar. 8, 2013, pp. 213-220.
Dorwald, "Side Reactions in Organic Synthesis: A Guide to Successful Synthesis Design", Organic Process Research and development, vol. 9, No. 3, 2005, pp. 372-374.
Dyck et al., "Effects of Deuterium Substitution on the Catabolism of (3-Phenylethylamine: An In Vivo Study", Journal of Neurochemistry, vol. 46, Issue 2, 1986,.
Jordan, "Tamoxifen: A Most Unlikely Pioneering Medicine", Nature Reviews Drug Discovery, vol. 2, Issue 3, 2003, pp. 205-213.
Pieniaszek et al., "Moricizine Bioavailability via Simultaneous, Dual, Stable Isotope Administration: Bioequivalence Implications", Journal of Clinical Pharmacology, vol. 39, 1999, pp. 817-825.
Tonn et al., "Simultaneous Analysis of Diphenhydramine and a Stable Isotope Analog (2h10)Diphenhydramine using Capillary Gas Chromatography with Mass Selective Detection in Biological Fluids from Chronically Instrumented Pregnant Ewest", Biological Mass Spectrometry, vol. 22, Issue 11, 1993, pp. 633-642.
Mppagunta et al., "Crystalline Solids", Advanced Drug Delivery Reviews, vol. 48, 2001, pp. 3-26.
Wolen, "The Application of Stable Isotopes to Studies of Drug Bioavailability and Bioequivalence", Journal of Clinical Pharmacology, vol. 26, 1986, pp. 419-424.
Japanese Application No. 2020-540580, Office Action dated Apr. 19, 2022, 4 pages.

* cited by examiner

SUBSTITUTED PYRAZOLO[1,5-A]PYRIMIDINE MACROCYCLIC COMPOUND

TECHNICAL FIELD

The invention relates to the technical field of medicine, and in particular to a substituted pyrazolo[1,5-a]pyrimidine macrocyclic compound and a composition comprising the same and use thereof. More specifically, the present invention relates to certain deuterium substituted 9-fluoro-15-methyl-2,11,16,20,21,24-hexaazapentocyclo[16.5.2.0$^{2,6}$, 0$^{7,12}$,0$^{21,25}$]pentacosane-1(24),7,9,11,18(25),19,22-heptaene-17-ones and stereoisomers thereof, and these deuterium-substituted compounds exhibit inhibition of Trk family protein tyrosine kinase and are useful for use in the treatment of pain, inflammation, cancers and certain infectious diseases, and these deuterium-substituted compounds have superior pharmacokinetic properties.

BACKGROUND TECHNIQUE

Trks are high affinity receptor tyrosine kinases activated by a group of soluble growth factors called neurotrophins (NTs). The Trk receptor family has three members, namely TrkA, TrkB and TrkC. Among the neurotrophins are (1) nerve growth factor (NGF) which can activate TrkA, (2) brain-derived neurotrophic factor (BDNF) and NT-4/5 which can activate TrkB, and (3) NT3 which can activate TrkC. Trks are widely expressed in neuronal tissues and are involved in the maintenance, signaling and survival of neuronal cells.

Literatures also show that the overexpression, activation, amplification and/or mutation of Trks are associated with many cancers including neurocytoma, ovarian cancer, breast cancer, prostate cancer, pancreatic cancer, multiple myeloma, astrocytoma, medulloblastoma, glioma, melanoma, thyroid cancer, pancreatic cancer, large cell neuroendocrine tumor and colorectal cancer. In addition, inhibitors of the Trk/neurotrophin pathway have been shown to be effective in a variety of preclinical animal models for the treatment of pain and inflammatory diseases.

The neurotrophin/Trk pathway, particularly the BDNF/TrkB pathway, has also been implicated in the pathogenesis of neurodegenerative diseases, including multiple sclerosis, Parkinson's disease, and Alzheimer's disease. The modulation of neurotrophin/Trk pathway can be used to treat these and related diseases.

It is believed that a TrkA receptor is critical for the disease process in the parasitic infection of *Trypanosoma cruzi* (Chagas disease) in human hosts. Therefore, TrkA inhibitors can be used to treat Chagas disease and related protozoal infections.

Trk inhibitors can also be used to treat diseases associated with imbalances in bone remodeling modulation, such as osteoporosis, rheumatoid arthritis, and bone metastasis. Bone metastasis is a common complication of cancer, up to 70% in patients with advanced breast or prostate cancer and about 15 to 30% in patients with lung, colon, stomach, bladder, uterine, rectal, thyroid or kidney cancer. Osteolytic metastasis can cause severe pain, pathological fractures, life-threatening hypercalcemia, spinal cord compression, and other nerve compression syndromes. For these reasons, bone metastasis is a serious cancer complication that is costly. Therefore, an agent that can induce apoptosis of proliferative bone cells is very advantageous. Expression of TrkA receptors and TrkC receptors has been observed in the osteogenic region of the fractured mouse model. In addition, almost all osteoblast apoptosis agents are very advantageous. Expression of TrkA receptors and TrkC receptors has been observed in the osteogenic region of the fractured mouse model. In addition, localization of NGF was observed in almost all osteoblasts. Recently, it was demonstrated that pan-Trk inhibitors could inhibit tyrosine signaling activated by neurotrophic factors that bind to all three Trk receptors in human hFOB osteoblasts. This data support the theory of using Trk inhibitors to treat bone remodeling diseases, such as bone metastasis in cancer patients.

Larotrectinib (LOXO-101) is the first generation of Trk inhibitor developed by Loxo Oncology. LOXO-101 began to be used for treatment of the first patient in March 2015; was granted a breakthrough drug qualification on Jul. 13, 2016 by the FDA for the unresectable or metastatic solid tumor of adults and children with positive Trk fusion gene mutations; the key enrollment was completed in February 2017. However, after treatment with the Larotrectinib inhibitor, the Trk gene of cancer patients may produce some mutations, such as NTRK1 G595R, NTRK3 G623R and other mutations, resulting in drug resistance. LOXO-195, the chemical name of which is (6R,15R)-9-fluoro-15-methyl-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one with the following structural formula, is a second-generation of Trk inhibitor developed by Loxo Oncology. It can effectively resist the drug resistance produced by Larotrectinib. It has been demonstrated that an adult patient with colorectal cancer and a child patient with fibrosarcoma developed Larotrectinib resistance and then received LOXO-195 for purpose of treatment, resulting in prolonging the course of diseases of patients with a Trk gene mutation. The patients have a sustained release effect with few side effects (Drilon. A., et al., Cancer Discov. 2017, 7(9), 1-10). At present, the FDA has officially approved LOXO-195 as an experimental new drug for clinical Phase I and Phase II trials.

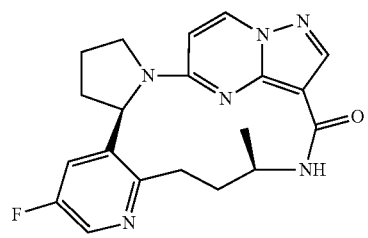

LOXO-195

Poor absorption, distribution, metabolism, and/or excretion (ADME) properties are known to be the primary cause of clinical trial failure in many drug candidates. Many of the drugs currently on the market also have limited range of applications due to poor ADME properties. The rapid metabolism of drugs can lead to the difficulty in drugability for many drugs that otherwise could effectively treat diseases because they are too quickly removed from the body. Frequent or high-dose administrations may solve the problem of rapid drug clearance, but this approach can lead to problems such as poor patient compliance, side effects caused by high-dose administrations, and increased treatment costs. In addition, rapidly metabolized drugs may also expose patients to undesirable toxic or reactive metabolites.

Although LOXO-195 is effective as a Trk inhibitor in the treatment of a variety of cancers or the like, it has been found that a novel compound having a very good oral bioavailability and a drugability for treating cancers or the like is still a challenging task. Thus, there remains a need in the art to develop compounds useful as therapeutic agents having selective inhibitory activity for Trk kinase mediated diseases or better pharmacodynamics/pharmacokinetics, and the present invention provides such compounds.

SUMMARY

For the above technical problems, the present invention discloses a novel deuterium-substituted 9-fluoro-15-methyl-2,11,16,20,21,24-hexaazapentocyclo[16.5.2.0$^{2,6}$,0$^{7,12}$,0$^{21,}$ $_{25}$]pentacosane-1(24),7,9,11,18(25),19,22-heptaene-17-one and stereoisomers thereof, such as compound Φ, compound Φ-a and compound Φ-b with the following structural formulas, and a composition and use thereof, which has better Trk kinase inhibitory activity, lower side effects, better pharmacodynamic and/or pharmacokinetic properties, and can be used to treat Trk kinase mediated diseases.

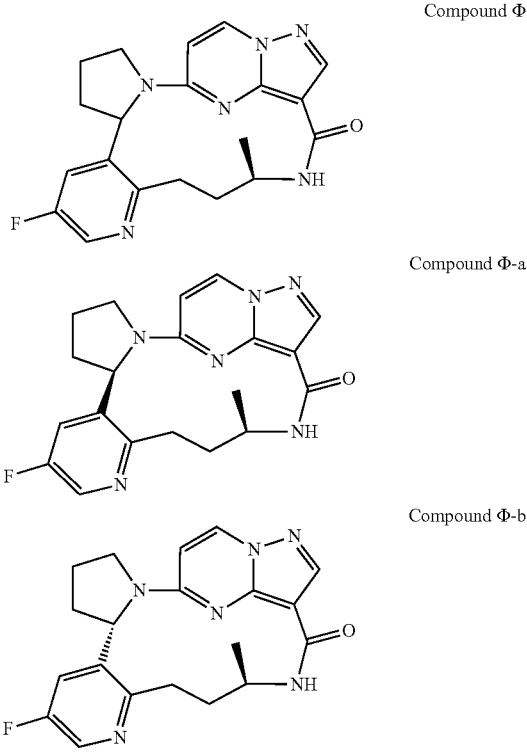

Compound Φ

Compound Φ-a

Compound Φ-b

As used herein, the term "compound of the invention" refers to compounds of formula (A), formula (A-1), formula (A-2), formula (Aa), formula (Aa-1), formula (Aa-2), formula (I), formula (II), formula (III), formula (IV), formula (Ia), formula (IIa), formula (IIIa) and formula (IVa). The term also includes a pharmaceutically acceptable salt, a prodrug, a hydrate or a solvate, a polymorph, a stereoisomer or an isotopic variant of the compounds of formula (A), formula (A-1), formula (A-2), formula (Aa), formula (Aa-1), formula (Aa-2), formula (I), formula (II), formula (III), formula (IV), formula (Ia), formula (IIa), formula (IIIa) and formula (IVa).

In this regard, the present invention adopts the following technical solutions.

In a first aspect of the invention, there is provided a compound of formula (Aa):

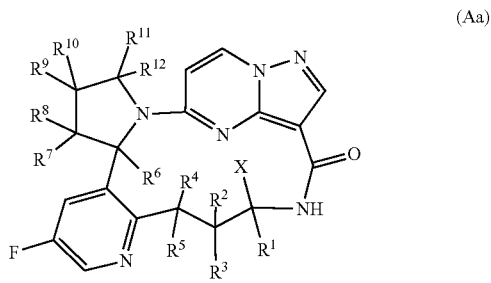

(Aa)

or a pharmaceutically acceptable salt, a prodrug, a hydrate or a solvate, a polymorph, a stereoisomer or an isotopic variant thereof,
wherein,
$R^1$, $R^2$, $R^3$, $R^4$, $R^5$, $R^6$, $R^7$, $R^8$, $R^9$, $R^{10}$, $R^{11}$ and $R^{12}$ are each independently selected from hydrogen or deuterium;
X is selected from $CH_3$, $CD_3$, $CHD_2$ or $CH_2D$;
with the proviso that if X is $CH_3$, then at least one of $R^1$, $R^2$, $R^3$, $R^4$, $R^5$, $R^6$, $R^7$, $R^8$, $R^9$, $R^{10}$, $R^{11}$ and $R^{12}$ is deuterium.

In another aspect of the invention, there is provided a compound of formula (I):

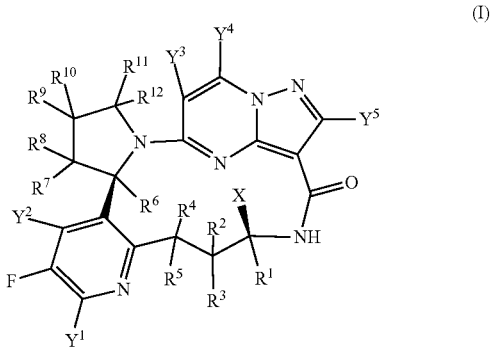

(I)

or a pharmaceutically acceptable salt, a prodrug, a hydrate or a solvate, a polymorph, a stereoisomer or an isotopic variant thereof,
wherein,
$R^1$, $R^2$, $R^3$, $R^4$, $R^5$, $R^6$, $R^7$, $R^8$, $R^9$, $R^{10}$, $R^{11}$, $R^{12}$, $Y^1$, $Y^2$, $Y^3$, $Y^4$ and $Y^5$ are each independently selected from hydrogen or deuterium;
X is selected from $CH_3$, $CD_3$, $CHD_2$ or $CH_2D$;
with the proviso that if X is $CH_3$, then at least one of $R^1$, $R^2$, $R^3$, $R^4$, $R^5$, $R^6$, $R^7$, $R^8$, $R^9$, $R^{10}$, $R^{11}$, $R^{12}$, $Y^1$, $Y^2$, $Y^3$, $Y^4$ and $Y^5$ is deuterium.

In another aspect, the invention provides a pharmaceutical composition comprising a compound of the invention and a pharmaceutically acceptable excipient. In a particular embodiment, the compound of the invention is provided in the pharmaceutical composition in an effective amount. In a particular embodiment, the compound of the invention is provided in a therapeutically effective amount. In a particular embodiment, the compound of the invention is provided in a prophylactically effective amount.

In another aspect, the present invention provides a process for the preparation of a pharmaceutical composition as described above, comprising the steps of: mixing a pharmaceutically acceptable excipient with a compound of the present invention to form the pharmaceutical composition.

In another aspect, the invention also relates to a method of treating a disease mediated by a Trk kinase in a subject. The method comprises administering to the subject a therapeutically effective amount of a compound of the invention. In a specific embodiment, the cancer is mediated by TrkA, TrkB or both. In a specific embodiment, the patient is diagnosed or identified as having a Trk-related cancer. In a specific embodiment, the compound is administered orally, subcutaneously, intravenously or intramuscularly. In a specific embodiment, the compound is administered chronically.

In a specific embodiment, the Trk kinase mediated disease is selected from the group consisting of pain, cancers, inflammation, neurodegenerative diseases or trypanosomal infections.

Other objects and advantages of the present invention will be apparent to those skilled in the art from the following detailed description, examples and claims.

DETAILED DESCRIPTION

Definition

As used herein, unless otherwise specified, "deuterated" means that one or more hydrogens in a compound or group are replaced by deuterium; deuterated may be monosubstituted, disubstituted, polysubstituted or fully substituted. The term "one or more deuterated" is used interchangeably with the term "one or multiple deuterated".

As used herein, unless otherwise specified, "a non-deuterated compound" means a compound containing a proportion of deuterium atoms not higher than the natural deuterium isotope content (0.015%).

The term "pharmaceutically acceptable salts" means those salts suitable for contact with tissues of humans and lower animals without excessive toxicity, irritation, allergies, etc., and compatible with reasonable benefit/risk ratios within the scope of sound medical judgment. Pharmaceutically acceptable salts are well known in the art. For example, the pharmaceutically acceptable salts are described in detail in Berge et al., J. Pharmaceutical Sciences (1977) 66: 1-19. Pharmaceutically acceptable salts of the compounds of the invention include those derived from suitable inorganic and organic acids and bases.

The invention also includes isotopically labeled compounds, equivalent to the original compounds disclosed herein. Examples of isotopes which may be included in the compounds of the present invention include hydrogen, carbon, nitrogen, oxygen, phosphorus, sulfur, fluorine and chlorine isotopes such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl respectively. The compounds of the present invention, or enantiomer, diastereomer, isomer, or pharmaceutically acceptable salt or solvate thereof, in which the above isotopes or other isotopic atoms are contained, are within the scope of the present invention. Certain isotopically-labeled compounds of the present invention, for example also containing the radioisotopes of $^3$H and $^{14}$C, are useful in tissue distribution experiments of drugs and substrates. Tritium, i.e. $^3$H and carbon 14, i.e. $^{14}$C, are easier to be prepared and detected and are preferred in isotopes. Isotopically labeled compounds can be prepared in a conventional manner by substituting a readily available isotopically labeled reagent for a non-isotopic reagent using the protocol of the examples.

The compounds of the invention may include one or more asymmetric centers, and thus may exist in a variety of "stereoisomer" forms, for example, enantiomeric and/or diastereomeric forms. For example, the compounds of the invention may be in the form of individual enantiomers, diastereomers or geometric isomers (e.g., cis and trans isomers), or may be in the form of a mixture of stereoisomers, including a racemic mixture and a mixture rich in one or more stereoisomers. The isomers can be separated from the mixture by methods known to those skilled in the art, including: chiral high pressure liquid chromatography (HPLC) and the formation and crystallization of a chiral salt; or preferred isomers can be prepared by asymmetric synthesis.

The compounds of the invention may be in an amorphous or crystal form. Furthermore, the compounds of the invention may exist in one or more crystal forms. Accordingly, the invention includes within its scope all amorphous or crystal forms of the compounds of the invention. The term "crystal form" refers to a different arrangement of chemical drug molecules, generally expressed as the form of a pharmaceutical material in a solid state. A drug may exist in a plurality of crystal forms, and different crystal forms of the same drug may have different dissolution and absorption in the body, thereby affecting the dissolution and release of the formulation.

The term "solvate" refers to a complex formed by the coordination of a compound of the invention with a solvent molecule in a specific ratio. The term "hydrate" refers to a complex formed by the coordination of a compound of the invention with water.

The term "prodrug" refers to a compound that is converted in vivo to an active form having its medical effect by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon, and H. Barbra "Improved oral drug delivery: Solubility limitations overcome by the use of prodrugs", Advanced Drug Delivery Reviews (1996) 19(2) 115-130, both of which are hereby incorporated by reference herein.

A prodrug is any covalently bonded compound of the invention, when administered to a patient, which releases the parent compound in vivo. Prodrugs are typically prepared by modifying functional groups in such a way that the modifications can be cleaved by routine manipulation or in vivo to yield the parent compound. Prodrugs include, for example, a compound of the invention wherein a hydroxy, amino or thiol group is bonded to any group, when administered to a patient, which can be cleaved to form a hydroxy, amino or thiol group. Thus, representative examples of prodrugs include, but are not limited to, the acetate/amide, formate/amide and benzoate/amide derivatives of hydroxy, thiol and amino functional groups of the compounds of the invention. Further, in the case of a carboxylic acid (—COOH), an ester such as a methyl ester, an ethyl ester or the like can be used. The ester itself may be active and/or may be hydrolyzed in vivo in human body. Suitable pharmaceutically acceptable in vivo hydrolysable ester groups include those groups which are readily decomposed in human body to release the parent acid or a salt thereof.

The term "crystal form" refers to a different arrangement of chemical drug molecules, generally expressed as the form of a pharmaceutical material in a solid state. A drug may exist in a plurality of crystal forms, and different crystal forms of the same drug may have different dissolution and absorption in the body, thereby affecting the dissolution and release of the formulation.

As used herein, the term "subject" includes, but is not limited to, a human (i.e., a male or female of any age group, e.g., a pediatric subject, such as an infant, a child, or an adolescent, or an adult subject, such as, a young adult, a middle-aged adult or an older adult) and/or non-human animals, for example, mammals, such as primates (e.g., cynomolgus monkeys, rhesus monkeys), cattle, pigs, horses, sheep, goats, rodents, cats and/or dogs. In some embodiments, the subject is a human. In other embodiments, the subject is a non-human animal.

The terms "disease", "disorder" and "condition" are used interchangeably herein.

Unless otherwise indicated, the term "treatment" as used herein includes the action that occurs when a subject has had a particular disease, disorder or condition, and that reduces the severity of the disease, disorder or condition, or delays or slows the development of the disease, disorder or condition ("therapeutic treatment"), but also the action that occurs before the subject begins to have a particular disease, disorder or condition ("prophylactic treatment").

Generally, an "effective amount" of a compound refers to an amount sufficient to cause a target biological response. As will be understood by one of ordinary skill in the art, an effective amount of a compound of the invention can vary depending on factors such as the biological target, the pharmacokinetics of the compound, the disease being treated, the mode of administration, and the age, health conditions and symptoms of the subject. Effective amounts include therapeutically and prophylactically effective amounts.

A "therapeutically effective amount" of a compound, as used herein, is an amount sufficient to provide a therapeutic benefit in the course of treating a disease, disorder or condition, or to delay or minimize one or more symptoms associated with a disease, disorder or condition, unless otherwise stated. A therapeutically effective amount of a compound refers to the amount of a therapeutic agent used alone or in combination with other therapies that provides a therapeutic benefit in the course of treating a disease, disorder or condition. The term "therapeutically effective amount" can include an amount that improves overall treatment, reduces or avoids the symptoms or causes of a disease or condition, or enhances the therapeutic efficacy of other therapeutic agents.

A "prophylactically effective amount" of a compound, as used herein, is an amount sufficient to prevent a disease, disorder or condition, or an amount sufficient to prevent one or more symptoms associated with a disease, disorder or condition, or an amount to prevent relapses of a disease, disorder or condition, unless otherwise stated. A prophylactically effective amount of a compound refers to the amount of a therapeutic agent used alone or in combination with other agents that provides a prophylactic benefit in the prevention of a disease, disorder or condition. The term "prophylactically effective amount" can include an amount that improves the overall prevention, or an amount that enhances the prophylactic efficacy of other prophylactic agents.

"Combination" and related terms mean the simultaneous or sequential administration of therapeutic agents of the invention. For example, a compound of the invention may be administered simultaneously or sequentially with another therapeutic agent in separate unit dosage forms, or simultaneously together with another therapeutic agent in a single unit dosage form.

Compound

In one embodiment, the invention provides a compound of formula (A),

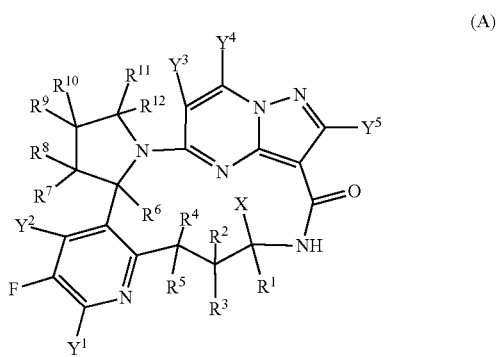

(A)

or a pharmaceutically acceptable salt, a prodrug, a hydrate or a solvate, a polymorph, a stereoisomer or an isotopic variant thereof, wherein, $R^1, R^2, R^3, R^4, R^5, R^6, R^7, R^8, R^9, R^{10}, R^{11}, R^{12}, Y^1, Y^2, Y^3, Y^4$ and $Y^5$ are each independently selected from hydrogen or deuterium;

X is selected from $CH_3$, $CD_3$, $CHD_2$ or $CH_2D$;

with the proviso that if X is $CH_3$, then at least one of $R^1, R^2, R^3, R^4, R^5, R^6, R^7, R^8, R^9, R^{10}, R^{11}, R^{12}, Y^1, Y^2, Y^3, Y^4$ and $Y^5$ is deuterium.

In a specific embodiment, the technical solution that "$R^1, R^2, R^3, R^4, R^5, R^6, R^7, R^8, R^9, R^{10}, R^{11}$ and $R^{12}$ are each independently selected from hydrogen or deuterium" includes $R^1$ being selected from hydrogen or deuterium, $R^2$ being selected from hydrogen or deuterium, $R^3$ being selected from hydrogen or deuterium, and so on, until $R^{12}$ being selected from hydrogen or deuterium; more specifically, R being hydrogen or $R^1$ being deuterium, $R^2$ being hydrogen or $R^2$ being deuterium, $R^3$ being hydrogen or $R^3$ being deuterium, and so on, until $R^{12}$ being hydrogen or $R^{12}$ being deuterium. In another specific embodiment, the technical solution that "$Y^1, Y^2, Y^3, Y^4$ and $Y^5$ are each independently selected from hydrogen or deuterium" includes $Y^1$ being selected from hydrogen or deuterium, $Y^2$ being selected from hydrogen or deuterium, $Y^3$ being selected from hydrogen or deuterium, and so on, until $Y^5$ being selected from the hydrogen or deuterium; more specifically, $Y^1$ being hydrogen or $Y^1$ being deuterium, $Y^2$ being hydrogen or $Y^2$ being deuterium, $Y^3$ being hydrogen or $Y^3$ being deuterium, and so on, until $Y^5$ being hydrogen or $Y^5$ being deuterium.

In another specific embodiment, the technical solution that "X is selected from $CH_3$, $CD_3$, $CHD_2$ or $CH_2D$" includes X being $CH_3$, X being $CD_3$, X being $CHD_2$ or X being $CH_2D$.

In a specific embodiment, the invention relates to a compound of formula (A-1),

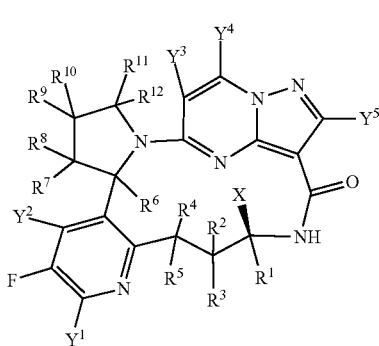

(A-1)

or a pharmaceutically acceptable salt, a prodrug, a hydrate or a solvate, a polymorph, a stereoisomer or an isotopic variant thereof,
wherein,
$R^1, R^2, R^3, R^4, R^5, R^6, R^7, R^8, R^9, R^{10}, R^{11}, R^{12}, Y^1, Y^2, Y^3, Y^4$ and $Y^5$ are each independently selected from hydrogen or deuterium;
X is selected from $CH_3$, $CD_3$, $CHD_2$ or $CH_2D$;
with the proviso that if X is $CH_3$, then at least one of $R^1, R^2, R^3, R^4, R^5, R^6, R^7, R^8, R^9, R^{10}, R^{11}, R^{12}, Y^1, Y^2, Y^3, Y^4$ and $Y^5$ is deuterium.

In another specific embodiment, the invention relates to a compound of formula (I),

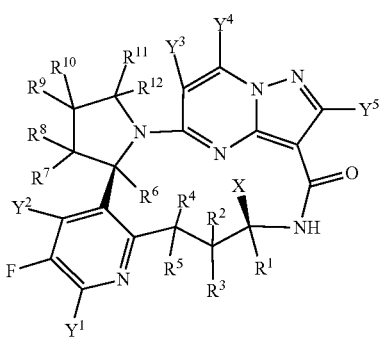

(I)

or a pharmaceutically acceptable salt, a prodrug, a hydrate or a solvate, a polymorph, a stereoisomer or an isotopic variant thereof,
wherein,
$R^1, R^2, R^3, R^4, R^5, R^6, R^7, R^8, R^9, R^{10}, R^{11}, R^{12}, Y^1, Y^2, Y^3, Y^4$ and $Y^5$ are each independently selected from hydrogen or deuterium;
X is selected from $CH_3$, $CD_3$, $CHD_2$ or $CH_2D$;
with the proviso that if X is $CH_3$, then at least one of $R^1, R^2, R^3, R^4, R^5, R^6, R^7, R^8, R^9, R^{10}, R^{11}, R^{12}, Y^1, Y^2, Y^3, Y^4$ and $Y^5$ is deuterium.

In another specific embodiment, the invention relates to a compound of formula (II),

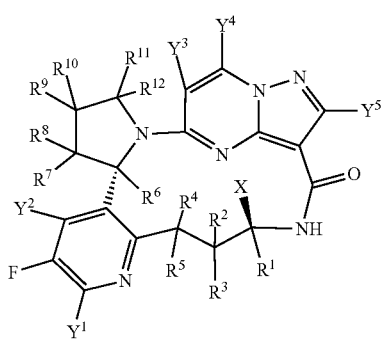

(II)

or a pharmaceutically acceptable salt, a prodrug, a hydrate or a solvate, a polymorph, a stereoisomer or an isotopic variant thereof,
wherein,
$R^1, R^2, R^3, R^4, R^5, R^6, R^7, R^8, R^9, R^{10}, R^{11}, R^{12}, Y^1, Y^2, Y^3, Y^4$ and $Y^5$ are each independently selected from hydrogen or deuterium;
X is selected from $CH_3$, $CD_3$, $CHD_2$ or $CH_2D$;
with the proviso that if X is $CH_3$, then at least one of $R^1, R^2, R^3, R^4, R^5, R^6, R^7, R^8, R^9, R^{10}, R^{11}, R^{12}, Y^1, Y^2, Y^3, Y^4$ and $Y^5$ is deuterium.

As a preferred embodiment of the present invention, the compounds of formula (A), formula (A-1), formula (I) and formula (II) contain at least one deuterium atom, more preferably one deuterium atom, more preferably two deuterium atoms, more preferably three deuterium atoms, more preferably four deuterium atoms, more preferably five deuterium atoms, more preferably six deuterium atoms, more preferably seven deuterium atoms, more preferably eight deuterium atoms, more preferably nine deuterium atoms, more preferably ten deuterium atoms, more preferably eleven deuterium atoms, more preferably twelve deuterium atoms, more preferably thirteen deuterium atoms, more preferably fourteen deuterium atoms, and more preferably fifteen deuterium atoms.

As a preferred embodiment of the invention, the content of deuterium isotope in deuterated positions is at least greater than the natural content of deuterium isotope (0.015%), preferably greater than 30%, more preferably greater than 50%, more preferably greater than 75%, more preferably greater than 95%, and more preferably greater than 99%.

Specifically, in the present invention, the content of deuterium isotope in each deuterated position of $R^1, R^2, R^3, R^4, R^5, R^6, R^7, R^8, R^9, R^{10}, R^{11}, R^{12}, Y^1, Y^2, Y^3, Y^4, Y^5$ and X is at least 5%, preferably greater than 10%, more preferably greater than 15%, more preferably greater than 20%, more preferably greater than 25%, more preferably greater than 30%, more preferably greater than 35%, more preferably greater than 40%, more preferably greater than 45%, more preferably greater than 50%, more preferably greater than 55%, more preferably greater than 60%, more preferably greater than 65%, more preferably greater than 70%, more preferably greater than 75%, more preferably greater than 80%, more preferably greater than 85%, more preferably greater than 90%, more preferably greater than 95%, and more preferably greater than 99%.

In another specific embodiment, at least one of $R^1$, $R^2$, $R^3$, $R^4$, $R^5$, $R^6$, $R^7$, $R^8$, $R^9$, $R^{10}$, $R^{11}$, $R^{12}$, $Y^1$, $Y^2$, $Y^3$, $Y^4$, $Y^5$ and X of the compounds of formula (A), formula (A-1), formula (I) and formula (II) contains deuterium, more preferably two contain deuterium, more preferably three contain deuterium, more preferably four contain deuterium, more preferably five contain deuterium, more preferably six contain deuterium, more preferably seven contain deuterium, more preferably eight contain deuterium, more preferably nine contain deuterium, more preferably ten contain deuterium, more preferably eleven contain deuterium, more preferably twelve contain deuterium, more preferably thirteen contain deuterium, more preferably fourteen contain deuterium, more preferably fifteen contain deuterium, more preferably sixteen contain deuterium, more preferably seventeen contain deuterium, more preferably eighteen contain deuterium, more preferably nineteen contain deuterium, and more preferably twenty contain deuterium. Specifically, the compounds of formula (A), formula (A-1), formula (I) and formula (II) contain at least one, two, three, four, five, six, seven, eight, nine, ten, eleven, twelve, thirteen, fourteen, fifteen, sixteen, seventeen, eighteen, nineteen, and twenty deuterium atoms.

In a specific embodiment of the invention, $R^1$ is selected from hydrogen or deuterium.

In another specific embodiment, $R^1$ is hydrogen.

In another specific embodiment, $R^1$ is deuterium.

In a specific embodiment of the invention, $R^2$, $R^3$, $R^4$, R are each independently selected from hydrogen or deuterium.

In another specific embodiment, $R^2$ and $R^3$ are the same.

In another specific embodiment, $R^4$ and $R^5$ are the same.

In another specific embodiment, $R^2$ and $R^3$ are both deuterium.

In another specific embodiment, $R^2$ and $R^3$ are both hydrogen.

In another specific embodiment, $R^4$ and $R^5$ are both deuterium.

In another specific embodiment, $R^4$ and $R^5$ are both hydrogen.

In another specific embodiment, $R^2$, $R^3$, $R^4$ and $R^5$ are all deuterium.

In another specific embodiment, $R^2$, $R^3$, $R^4$ and $R^5$ are all hydrogen.

In a specific embodiment of the present invention, $R^6$, $R^7$, $R^8$, $R^9$, $R^{10}$, $R^{11}$, $R^{12}$ are each independently selected from hydrogen or deuterium.

In another specific embodiment, $R^7$ and $R^8$ are the same.

In another specific embodiment, $R^9$ and $R^{10}$ are the same.

In another specific embodiment, $R^{11}$ and $R^{12}$ are the same.

In another specific embodiment, $R^6$, $R^7$ and $R^8$ are all deuterium.

In another specific embodiment, $R^6$, $R^7$ and $R^8$ are all hydrogen.

In another specific embodiment, $R^9$ and $R^{10}$ are both deuterium.

In another specific embodiment, $R^9$ and $R^{10}$ are both hydrogen.

In another specific embodiment, $R^{11}$ and $R^{12}$ are both deuterium.

In another specific embodiment, $R^{11}$ and $R^{12}$ are both hydrogen.

In a specific embodiment of the invention, X is selected from $CH_3$, $CD_3$, $CHD_2$ or $CH_2D$.

In another specific embodiment, X is selected from $CH_3$ or $CD_3$.

In a specific embodiment of the present invention, $Y^1$, $Y^2$, $Y^3$, $Y^4$ and $Y^5$ are each independently selected from hydrogen or deuterium.

In a specific embodiment of the present invention, X is $CD_3$, and $R^1$, $R^2$, $R^3$, $R^4$, $R^5$, $R^6$, $R^7$, $R^8$, $R^9$, $R^{10}$, $R^{11}$, $R^{12}$, $Y^1$, $Y^2$, $Y^3$, $Y^4$ and $Y^5$ are each independently selected from hydrogen or deuterium.

In another specific embodiment, X is $CD_3$, $Y^1$, $Y^2$, $Y^3$, $Y^4$, and $Y^5$ are all hydrogen, and $R^1$, $R^2$, $R^3$, $R^4$, $R^5$, $R^6$, $R^7$, $R^8$, $R^9$, $R^{10}$, $R^{11}$, and $R^{12}$ are each independently selected from hydrogen or deuterium.

In another specific embodiment, X is $CD_3$, $R^1$, $Y^1$, $Y^2$, $Y^3$, $Y^4$, and $Y^5$ are all hydrogen, and $R^2$, $R^3$, $R^4$, $R^5$, $R^6$, $R^7$, $R^8$, $R^9$, $R^{10}$, $R^{11}$, and $R^{12}$ are each independently selected from hydrogen or deuterium.

In another specific embodiment, X is $CD_3$, $R^1$, $R^2$, $R^3$, $R^4$, $R^5$, $Y^1$, $Y^2$, $Y^3$, $Y^4$, and $Y^5$ are all hydrogen, and $R^6$, $R^7$, $R^8$, $R^9$, $R^{10}$, $R^{11}$, and $R^{12}$ are each independently selected from hydrogen or deuterium.

In a specific embodiment of the present invention, $R^2$, $R^3$, $R^4$ and $R^5$ are all deuterium, $R^1$, $R^6$, $R^7$, $R^8$, $R^9$, $R^{10}$, $R^{11}$, $R^{12}$, $Y^1$, $Y^2$, $Y^3$, $Y^4$ and $Y^5$ are each independently selected from hydrogen or deuterium, and X is selected from $CH_3$ or $CD_3$.

In another specific embodiment, $R^2$, $R^3$, $R^4$, $R^5$, $R^6$, $R^7$, $R^8$ are all deuterium, $R^1$, $R^9$, $R^{10}$, $R^{11}$, $R^{12}$, $Y^1$, $Y^2$, $Y^3$, $Y^4$ and $Y^5$ are each independently selected from hydrogen or deuterium, and X is selected from $CH_3$ or $CD_3$.

In another specific embodiment, $R^2$, $R^3$, $R^4$, $R^5$, $R^9$ and $R^{10}$ are all deuterium, $R^6$, $R^7$, $R^8$, $R^{11}$, $R^{12}$, $Y^1$, $Y^2$, $Y^3$, $Y^4$ and $Y^5$ are each independently selected from hydrogen or deuterium, and X is selected from $CH_3$ or $CD_3$.

In another specific embodiment, $R^2$, $R^3$, $R^4$, $R^5$, $R^{11}$ and $R^{12}$ are all deuterium, $R^6$, $R^7$, $R^8$, $R^9$, $R^{10}$, $Y^1$, $Y^2$, $Y^3$, $Y^4$ and $Y^5$ are each independently selected from hydrogen or deuterium, and X is selected from $CH_3$ or $CD_3$.

In a specific embodiment of the present invention, $R^6$, $R^7$ and $R^8$ are all deuterium, $R^1$, $R^2$, $R^3$, $R^4$, $R^5$, $R^9$, $R^{10}$, $R^1$, $R^{12}$, $Y^1$, $Y^2$, $Y^3$, $Y^4$ and $Y^5$ are each independently selected from hydrogen or deuterium, and X is selected from $CH_3$ or $CD_3$.

In a specific embodiment of the present invention, $R^9$ and $R^{10}$ are both deuterium, $R^1$, $R^2$, $R^3$, $R^4$, $R^5$, $R^6$, $R^7$, $R^8$, $R^{11}$, $R^{12}$, $Y^1$, $Y^2$, $Y^3$, $Y^4$ and $Y^5$ are each independently selected from hydrogen or deuterium, and X is selected from $CH_3$ or $CD_3$.

In a specific embodiment of the present invention, $R^{11}$ and $R^{12}$ are both deuterium, $R^1$, $R^2$, $R^3$, $R^4$, $R^5$, $R^6$, $R^7$, $R^8$, $R^9$, $R^{10}$, $Y^1$, $Y^2$, $Y^3$, $Y^4$ and $Y^5$ are each independently selected from hydrogen or deuterium, and X is selected from $CH_3$ or $CD_3$.

In another embodiment, the invention relates to a compound of formula (Aa),

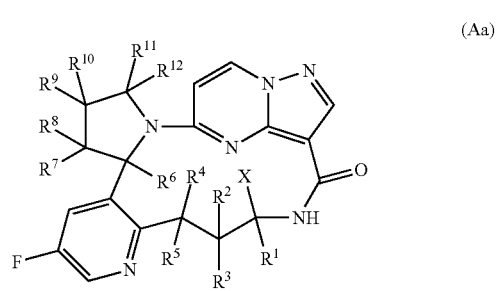

(Aa)

or a pharmaceutically acceptable salt, a prodrug, a hydrate or a solvate, a polymorph, a stereoisomer or an isotopic variant thereof,
wherein $R^1$-$R^{12}$ and X are as defined above.

In another embodiment, the invention relates to a compound of formula (Aa-1),

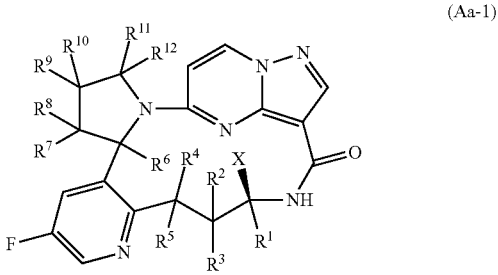

(Aa-1)

or a pharmaceutically acceptable salt, a prodrug, a hydrate or a solvate, a polymorph, a stereoisomer or an isotopic variant thereof,
wherein $R^1$-$R^{12}$ and X are as defined above.

In another specific embodiment, the present invention also relates to a compound of formula (Ia),

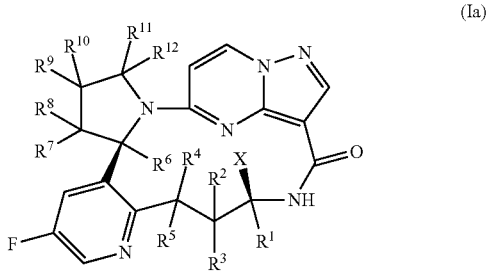

(Ia)

or a pharmaceutically acceptable salt, a prodrug, a hydrate or a solvate, a polymorph, a stereoisomer or an isotopic variant thereof,
wherein $R^1$-$R^{12}$ and X are as defined above.

In another specific embodiment, the present invention also relates to a compound of formula (IIa),

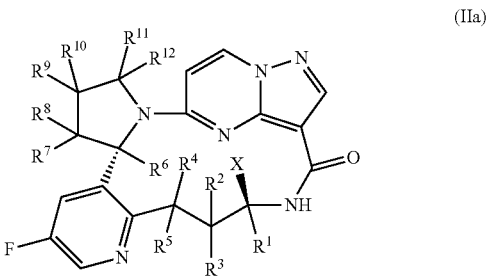

(IIa)

or a pharmaceutically acceptable salt, a prodrug, a hydrate or a solvate, a polymorph, a stereoisomer or an isotopic variant thereof,
wherein $R^1$-$R^{12}$ and X are as defined above.

In another specific embodiment, the invention provides a compound of formula (Aa), formula (Aa-1), formula (Ia) and formula (IIa), wherein $R^{11}$ and $R^{12}$ are selected from hydrogen, $R^1$-$R^{10}$ are each independently selected from hydrogen or deuterium, and X is selected from $CH_3$ or $CD_3$ with the proviso that the above compound contains at least one deuterium.

In another specific embodiment, the invention provides a compound of formula (Aa), formula (Aa-1), formula (Ia) and formula (IIa), wherein $R^9$ and $R^{10}$ are selected from hydrogen, $R^1$-$R^8$ and $R^{11}$-$R^{12}$ are each independently selected from hydrogen or deuterium, and X is selected from $CH_3$ or $CD_3$, with the proviso that the above compound contains at least one deuterium.

In another specific embodiment, the invention provides a compound of formula (Aa), formula (Aa-1), formula (Ia) and formula (IIa), wherein $R^9$-$R^{12}$ are selected from hydrogen, $R^1$-$R^8$ are each independently selected from hydrogen or deuterium, and X is selected from $CH_3$ or $CD_3$ with the proviso that the above compound contains at least one deuterium.

In another specific embodiment, the invention provides a compound of formula (Aa), formula (Aa-1), formula (Ia) and formula (IIa), wherein R is selected from H, $R^2$-$R^{12}$ are each independently selected from hydrogen or deuterium, and X is selected from $CH_3$ or $CD_3$ with the proviso that the above compound contains at least one deuterium.

In another specific embodiment, the invention provides a compound of formula (Aa), formula (Aa-1), formula (Ia) and formula (IIa), wherein $R^1$, $R^{11}$ and $R^{12}$ are selected from hydrogen, $R^2$-$R^{10}$ are each independently selected from hydrogen or deuterium, and X is selected from $CH_3$ or $CD_3$ with the proviso that the above compound contains at least one deuterium.

In another specific embodiment, the invention provides a compound of formula (Aa), formula (Aa-1), formula (Ia) and formula (IIa), wherein $R^1$, $R^9$ and $R^{10}$ are selected from hydrogen, $R^2$-$R^8$ and $R^{11}$-$R^{12}$ are each independently selected from hydrogen or deuterium, and X is selected from $CH_3$ or $CD_3$, with the proviso that the above compound contains at least one deuterium.

In another specific embodiment, the invention provides a compound of formula (Aa), formula (Aa-1), formula (Ia) and formula (IIa), wherein $R^1$, $R^9$-$R^{12}$ are selected from hydrogen, $R^2$-$R^8$ are each independently selected from hydrogen or deuterium, and X is selected from $CH_3$ or $CD_3$ with the proviso that the above compound contains at least one deuterium.

In another specific embodiment, the invention provides a compound of formula (Aa), formula (Aa-1), formula (Ia) and formula (IIa), wherein X is selected from $CH_3$, and $R^{11}$-$R^{12}$ are each independently selected from hydrogen or deuterium, with the proviso that the above compound contains at least one deuterium.

In another specific embodiment, the invention provides a compound of formula (Aa), formula (Aa-1), formula (Ia) and formula (IIa), wherein X is selected from $CH_3$, $R^{11}$ and $R^{12}$ are selected from hydrogen, and $R^1$-$R^{10}$ are each independently selected from hydrogen or deuterium, with the proviso that the above compound contains at least one deuterium.

In another specific embodiment, the invention provides a compound of formula (Aa), formula (Aa-1), formula (Ia) and formula (IIa), wherein X is selected from $CH_3$, $R^9$ and $R^{10}$ are selected from hydrogen, and $R^1$-$R^8$ and $R^{11}$-$R^{12}$ are each independently selected from hydrogen or deuterium, with the proviso that the above compound contains at least one deuterium.

In another specific embodiment, the invention provides a compound of formula (Aa), formula (Aa-1), formula (Ia)

and formula (IIa), wherein X is selected from $CH_3$, $R^9$-$R^{12}$ are selected from hydrogen, and $R^1$-$R^8$ are each independently selected from hydrogen or deuterium, with the proviso that the above compound contains at least one deuterium.

In another specific embodiment, the invention provides a compound of formula (Aa), formula (Aa-1), formula (Ia) and formula (IIa), wherein X is selected from $CH_3$, $R^1$ is selected from H, and $R^2$-$R^{12}$ are each independently selected from hydrogen or deuterium, with the proviso that the above compound contains at least one deuterium.

In another specific embodiment, the invention provides a compound of formula (Aa), formula (Aa-1), formula (Ia) and formula (IIa), wherein X is selected from $CH_3$, $R^1$, $R^{11}$ and $R^{12}$ are selected from H, and $R^2$-$R^{10}$ are each independently selected from hydrogen or deuterium, with the proviso that the above compound contains at least one deuterium.

In another specific embodiment, the invention provides a compound of formula (Aa), formula (Aa-1), formula (Ia) and formula (IIa), wherein X is selected from $CH_3$, $R^1$, $R^9$ and $R^{10}$ are selected from H, and $R^2$-$R^8$ and $R^{11}$-$R^{12}$ are each independently selected from hydrogen or deuterium, with the proviso that the above compound contains at least one deuterium.

In another specific embodiment, the invention provides a compound of formula (Aa), formula (Aa-1), formula (Ia) and formula (IIa), wherein X is selected from $CH_3$, $R^1$ and $R^9$-$R^{12}$ are selected from H, and $R^2$-$R^8$ are each independently selected from hydrogen or deuterium, with the proviso that the above compound contains at least one deuterium.

In another specific embodiment, the invention provides a compound of formula (Aa), formula (Aa-1), formula (Ia) and formula (IIa), wherein $R^2$-$R^5$ are selected from hydrogen, $R^1$ and $R^6$-$R^{12}$ are each independently selected from hydrogen or deuterium, and X is selected from $CH_3$ or $CD_3$, with the proviso that the above compound contains at least one deuterium.

In another specific embodiment, the invention provides a compound of formula (Aa), formula (Aa-1), formula (Ia) and formula (IIa), wherein $R^2$-$R^5$ and $R^{11}$-$R^{12}$ are selected from hydrogen, $R^1$ and $R^6$-$R^{10}$ are each independently selected from hydrogen or deuterium, and X is selected from $CH_3$ or $CD_3$, with the proviso that the above compound contains at least one deuterium.

In another specific embodiment, the invention provides a compound of formula (Aa), formula (Aa-1), formula (Ia) and formula (IIa), wherein $R^2$-$R^5$ and $R^9$-$R^{10}$ are selected from hydrogen, $R^1$, $R^6$-$R^8$ and $R^{11}$-$R^{12}$ are each independently selected from hydrogen or deuterium, and X is selected from $CH_3$ or $CD_3$, with the proviso that the above compound contains at least one deuterium.

In another specific embodiment, the invention provides a compound of formula (Aa), formula (Aa-1), formula (Ia) and formula (IIa), wherein $R^2$-$R^5$ and $R^9$-$R^{12}$ are selected from hydrogen, $R^1$ and $R^6$-$R^8$ are each independently selected from hydrogen or deuterium, and X is selected from $CH_3$ or $CD_3$, with the proviso that the above compound contains at least one deuterium.

In another specific embodiment, the invention provides a compound of formula (Aa), formula (Aa-1), formula (Ia) and formula (IIa), wherein $R^1$-$R^5$ are selected from hydrogen, $R^6$-$R^{12}$ are each independently selected from hydrogen or deuterium, and X is selected from $CH_3$ or $CD_3$, with the proviso that the above compound contains at least one deuterium.

In another specific embodiment, the invention provides a compound of formula (Aa), formula (Aa-1), formula (Ia) and formula (IIa), wherein $R^1$-$R^5$ and $R^{11}$-$R^{12}$ are selected from hydrogen, $R^6$-$R^{10}$ are each independently selected from hydrogen or deuterium, and X is selected from $CH_3$ or $CD_3$, with the proviso that the above compound contains at least one deuterium.

In another specific embodiment, the invention provides a compound of formula (Aa), formula (Aa-1), formula (Ia) and formula (IIa), wherein $R^1$-$R^5$ and $R^9$-$R^{10}$ are selected from hydrogen, $R^6$-$R^8$ and $R^{11}$-$R^{12}$ are each independently selected from hydrogen or deuterium, and X is selected from $CH_3$ or $CD_3$, with the proviso that the above compound contains at least one deuterium.

In another specific embodiment, the invention provides a compound of formula (Aa), formula (Aa-1), formula (Ia) and formula (IIa), wherein $R^1$-$R^5$ and $R^9$-$R^{12}$ are selected from hydrogen, $R^6$-$R^8$ are each independently selected from hydrogen or deuterium, and X is selected from $CH_3$ or $CD_3$, with the proviso that the above compound contains at least one deuterium.

In another specific embodiment, the invention provides a compound of formula (Aa), formula (Aa-1), formula (Ia) and formula (IIa), wherein $R^2$-$R^5$ is selected from hydrogen, $R^1$ and $R^6$-$R^{12}$ are each independently selected from hydrogen or deuterium, and X is selected from $CH_3$, with the proviso that the above compound contains at least one deuterium.

In another specific embodiment, the invention provides a compound of formula (Aa), formula (Aa-1), formula (Ia) and formula (IIa), wherein $R^2$-$R^5$ and $R^{11}$-$R^{12}$ are selected from hydrogen, $R^1$ and $R^6$-$R^{10}$ are each independently selected from hydrogen or deuterium, and X is selected from $CH_3$, with the proviso that the above compound contains at least one deuterium.

In another specific embodiment, the invention provides a compound of formula (Aa), formula (Aa-1), formula (Ia) and formula (IIa), wherein $R^2$-$R^5$ and $R^9$-$R^{10}$ are selected from hydrogen, $R^1$, $R^6$-$R^8$ and $R^{11}$-$R^{12}$ are each independently selected from hydrogen or deuterium, and X is selected from $CH_3$, with the proviso that the above compound contains at least one deuterium.

In another specific embodiment, the invention provides a compound of formula (Aa), formula (Aa-1), formula (Ia) and formula (IIa), wherein $R^2$-$R^5$ and $R^9$-$R^{12}$ are selected from hydrogen, $R^1$ and $R^6$-$R^8$ are each independently selected from hydrogen or deuterium, and X is selected from $CH_3$, with the proviso that the above compound contains at least one deuterium.

In another specific embodiment, the invention provides a compound of formula (Aa), formula (Aa-1), formula (Ia) and formula (IIa), wherein $R^1$-$R^5$ are selected from hydrogen, $R^6$-$R^{12}$ are each independently selected from hydrogen or deuterium, and X is selected from $CH_3$, with the proviso that the above compound contains at least one deuterium.

In another specific embodiment, the invention provides a compound of formula (Aa), formula (Aa-1), formula (Ia) and formula (IIa), wherein $R^1$-$R^5$ and $R^{11}$-$R^{12}$ are selected from hydrogen, $R^6$-$R^{10}$ are each independently selected from hydrogen or deuterium, and X is selected from $CH_3$, with the proviso that the above compound contains at least one deuterium.

In another specific embodiment, the invention provides a compound of formula (Aa), formula (Aa-1), formula (Ia) and formula (IIa), wherein $R^1$-$R^5$ and $R^9$-$R^{10}$ are selected from hydrogen, $R^6$-$R^8$ and $R^{11}$-$R^{12}$ are each independently selected from hydrogen or deuterium, and X is selected from $CH_3$, with the proviso that the above compound contains at least one deuterium.

In another specific embodiment, the invention provides a compound of formula (Aa), formula (Aa-1), formula (Ia) and formula (IIa), wherein $R^1$-$R^5$ and $R^9$-$R^{12}$ are selected from hydrogen, $R^6$-$R^8$ are each independently selected from hydrogen or deuterium, and X is selected from $CH_3$, with the proviso that the above compound contains at least one deuterium.

In another specific embodiment, the invention provides a compound of formula (Aa), formula (Aa-1), formula (Ia) and formula (IIa), wherein $R^6$-$R^8$ is selected from deuterium, $R^1$-$R^5$ and $R^9$-$R^{12}$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^6$-$R^8$ are selected from deuterium, $R^{11}$-$R^{12}$ are selected from hydrogen, $R^1$-$R^5$ and $R^9$-$R^{10}$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^6$-$R^8$ are selected from deuterium, $R^9$-$R^{10}$ are selected from hydrogen, $R^1$-$R^5$ and $R^{11}$-$R^{12}$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^6$-$R^8$ are selected from deuterium, $R^9$-$R^{12}$ are selected from hydrogen, $R^1$-$R^5$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^6$-$R^8$ is selected from deuterium, $R^2$-$R^5$ is selected from hydrogen, $R^1$ and $R^9$-$R^{12}$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^6$-$R^8$ are selected from deuterium, $R^2$-$R^5$ and $R^{11}$-$R^{12}$ are selected from hydrogen, $R^1$ and $R^9$-$R^{10}$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^6$-$R^8$ are selected from deuterium, $R^2$-$R^5$ and $R^9$-$R^{10}$ are selected from hydrogen, $R^1$ and $R^{11}$-$R^{12}$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^1$ and $R^6$-$R^8$ are selected from deuterium, $R^2$-$R^5$ and $R^9$-$R^{12}$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^1$ and $R^6$-$R^8$ are selected from deuterium, $R^{11}$-$R^{12}$ are selected from hydrogen, $R^2$-$R^5$ and $R^9$-$R^{10}$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^1$ and $R^6$-$R^8$ are selected from deuterium, $R^9$-$R^{10}$ are selected from hydrogen, $R^2$-$R^5$ and $R^{11}$-$R^{12}$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^1$ and $R^6$-$R^8$ are selected from deuterium, $R^9$-$R^{12}$ are selected from hydrogen, $R^2$-$R^5$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^1$ and $R^6$-$R^8$ are selected from deuterium, $R^2$-$R^5$ are selected from hydrogen, $R^9$-$R^{12}$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^1$ and $R^6$-$R^8$ are selected from deuterium, $R^2$-$R^5$ and $R^{11}$-$R^{12}$ are selected from hydrogen, $R^9$-$R^{10}$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^1$ and $R^6$-$R^8$ are selected from deuterium, $R^2$-$R^5$ and $R^9$-$R^{10}$ are selected from hydrogen, $R^{11}$-$R^{12}$ are each independently selected from hydrogen or deuterium, and X is selected from $CH_3$ or $CD_3$.

In another specific embodiment, the invention provides a compound of formula (Aa), formula (Aa-1), formula (Ia) and formula (IIa), wherein $R^6$-$R^8$ are selected from deuterium, $R^1$-$R^5$ and $R^9$-$R^{12}$ are each independently selected from hydrogen or deuterium, and X is selected from $CH_3$.

In another specific embodiment, the invention provides a compound of formula (Aa), formula (Aa-1), formula (Ia) and formula (IIa), wherein $R^6$-$R^8$ are selected from deuterium, $R^{11}$-$R^{12}$ are selected from hydrogen, $R^1$-$R^5$ and $R^9$-$R^{10}$ are each independently selected from hydrogen or deuterium, and X is selected from $CH_3$.

In another specific embodiment, the invention provides a compound of formula (Aa), formula (Aa-1), formula (Ia) and formula (IIa), wherein $R^6$-$R^8$ are selected from deuterium, $R^9$-$R^{10}$ are selected from hydrogen, $R^1$-$R^5$ and $R^{11}$-$R^{12}$ are each independently selected from hydrogen or deuterium, and X is selected from $CH_3$.

In another specific embodiment, the invention provides a compound of formula (Aa), formula (Aa-1), formula (Ia) and formula (IIa), wherein $R^6$-$R^8$ are selected from deuterium, $R^9$-$R^{12}$ are selected from hydrogen, $R^1$-$R^5$ are each independently selected from hydrogen or deuterium, and X is selected from $CH_3$.

In another specific embodiment, the invention provides a compound of formula (Aa), formula (Aa-1), formula (Ia) and formula (IIa), wherein $R^6$-$R^8$ are selected from deuterium, $R^2$-$R^5$ are selected from hydrogen, $R^1$ and $R^9$-$R^{12}$ are each independently selected from hydrogen or deuterium, and X is selected from $CH_3$.

In another specific embodiment, the invention provides a compound of formula (Aa), formula (Aa-1), formula (Ia) and formula (IIa), wherein $R^6$-$R^8$ are selected from deuterium, $R^2$-$R^5$ and $R^{11}$-$R^{12}$ are selected from hydrogen, $R^1$ and $R^9$-$R^{10}$ are each independently selected from hydrogen or deuterium, and X is selected from $CH_3$.

In another specific embodiment, the invention provides a compound of formula (Aa), formula (Aa-1), formula (Ia) and formula (IIa), wherein $R^6$-$R^8$ are selected from deuterium, $R^2$-$R^5$ and $R^9$-$R^{10}$ are selected from hydrogen, $R^1$ and $R^{11}$-$R^{12}$ are each independently selected from hydrogen or deuterium, and X is selected from $CH_3$.

In another specific embodiment, the invention provides a compound of formula (Aa), formula (Aa-1), formula (Ia) and formula (IIa), wherein $R^1$ and $R^6$-$R^8$ are selected from deuterium, $R^2$-$R^5$ and $R^9$-$R^{12}$ are each independently selected from hydrogen or deuterium, and X is selected from $CH_3$.

In another specific embodiment, the invention provides a compound of formula (Aa), formula (Aa-1), formula (Ia) and formula (IIa), wherein $R^1$ and $R^6$-$R^8$ are selected from deuterium, and $R^{11}$-$R^{12}$ are selected from hydrogen, $R^2$-$R^5$ and $R^9$-$R^{10}$ are each independently selected from hydrogen or deuterium, and X is selected from $CH_3$.

In another specific embodiment, the invention provides a compound of formula (Aa), formula (Aa-1), formula (Ia) and formula (IIa), wherein $R^1$ and $R^6$-$R^8$ are selected from deuterium, $R^9$-$R^{10}$ are selected from hydrogen, $R^2$-$R^5$ and $R^{11}$-$R^{12}$ are each independently selected from hydrogen or deuterium, and X is selected from $CH_3$.

In another specific embodiment, the invention provides a compound of formula (Aa), formula (Aa-1), formula (Ia) and formula (IIa), wherein $R^1$ and $R^6$-$R^8$ are selected from deuterium, $R^9$-$R^{12}$ are selected from hydrogen, $R^2$-$R^5$ are each independently selected from hydrogen or deuterium, and X is selected from $CH_3$.

In another specific embodiment, the invention provides a compound of formula (Aa), formula (Aa-1), formula (Ia) and formula (IIa), wherein $R^1$ and $R^6$-$R^8$ are selected from deuterium, $R^2$-$R^5$ are selected from hydrogen, $R^9$-$R^{12}$ are each independently selected from hydrogen or deuterium, and X is selected from $CH_3$.

In another specific embodiment, the invention provides a compound of formula (Aa), formula (Aa-1), formula (Ia) and formula (IIa), wherein $R^1$ and $R^6$-$R^8$ are selected from deuterium, $R^2$-$R^5$ and $R^{11}$-$R^{12}$ are selected from hydrogen, $R^9$-$R^{10}$ are each independently selected from hydrogen or deuterium, and X is selected from $CH_3$.

In another specific embodiment, the invention provides a compound of formula (Aa), formula (Aa-1), formula (Ia) and formula (IIa), wherein $R^1$ and $R^6$-$R^8$ are selected from deuterium, $R^2$-$R^5$ and $R^9$-$R^{10}$ are selected from hydrogen, $R^{11}$-$R^{12}$ are each independently selected from hydrogen or deuterium, and X is selected from $CH_3$.

In another embodiment, the present invention relates to a compound of formula (Aa-2), formula (IIIa) and formula (IVa),

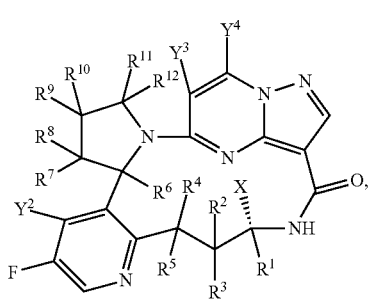
(A-2)

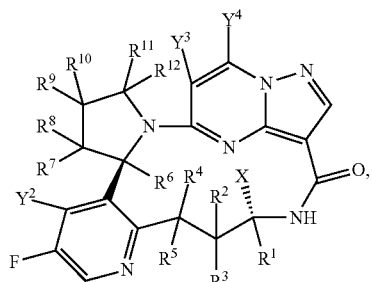
(III)

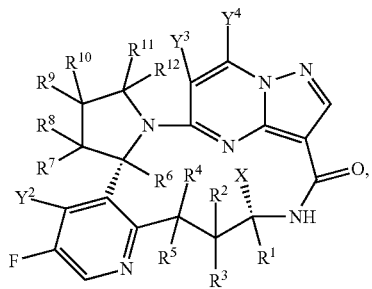
(IV)

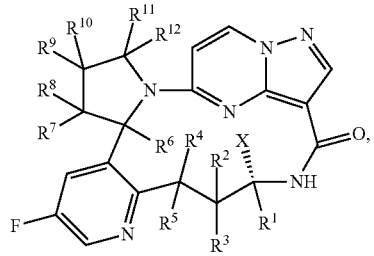
(Aa-2)

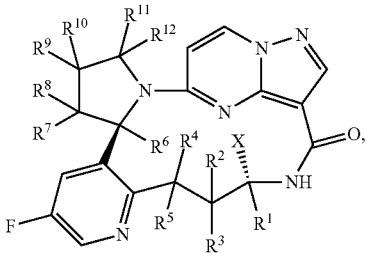
(IIIa)

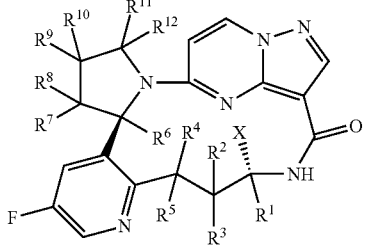
(IVa)

or a pharmaceutically acceptable salt, a prodrug, a hydrate or a solvate, a polymorph, a stereoisomer or an isotopic variant thereof, wherein $R^1$-$R^{12}$, $Y^1$-$Y^5$ and X are as defined above.

In a preferred embodiment of the invention, the compound is selected from the group consisting of:

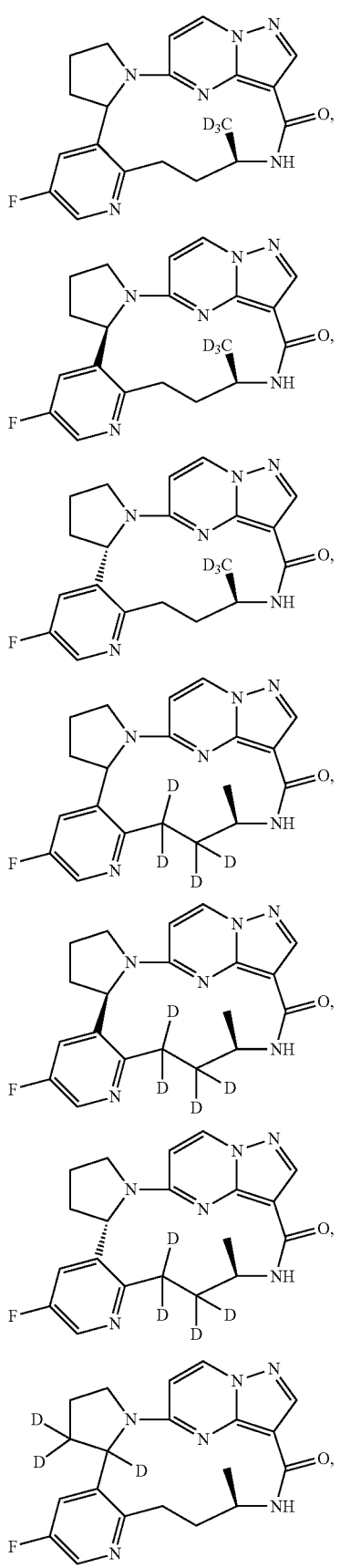
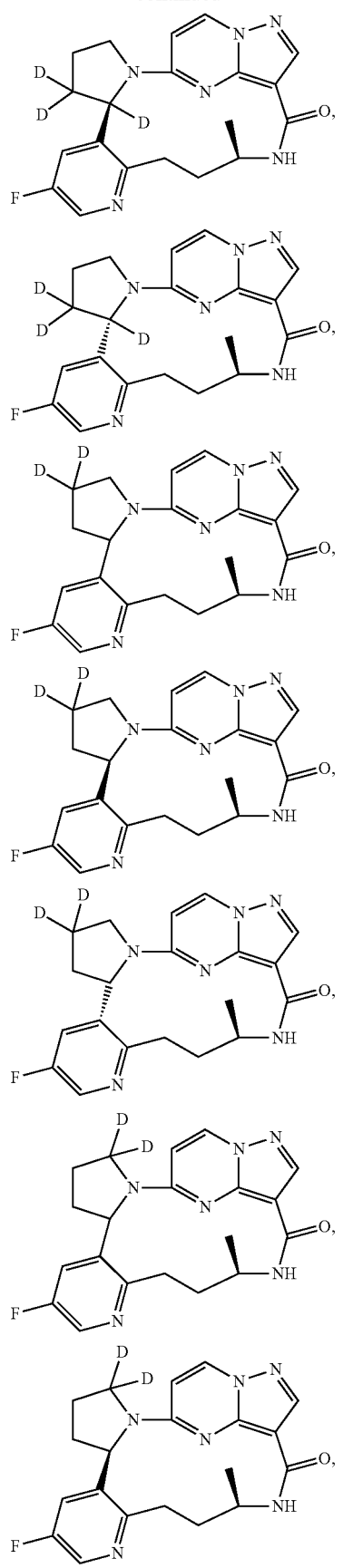

-continued
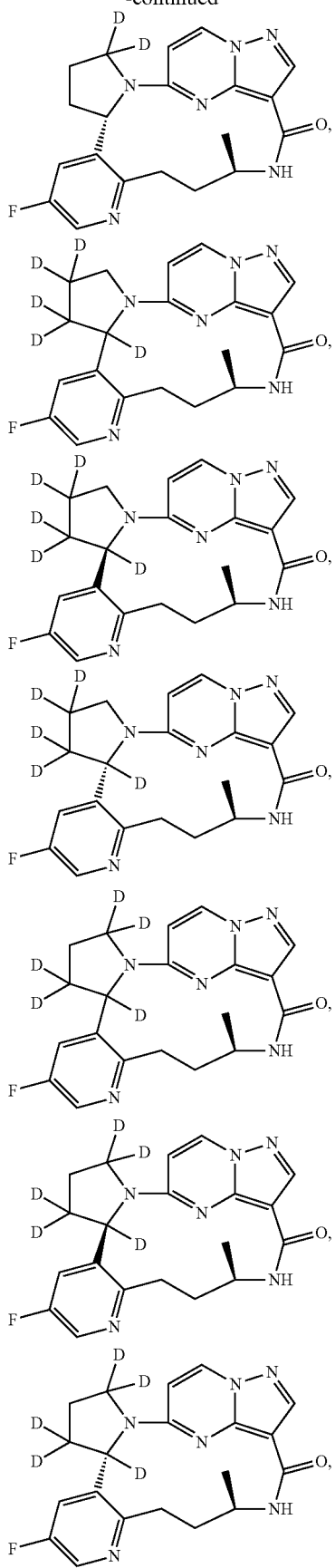
-continued
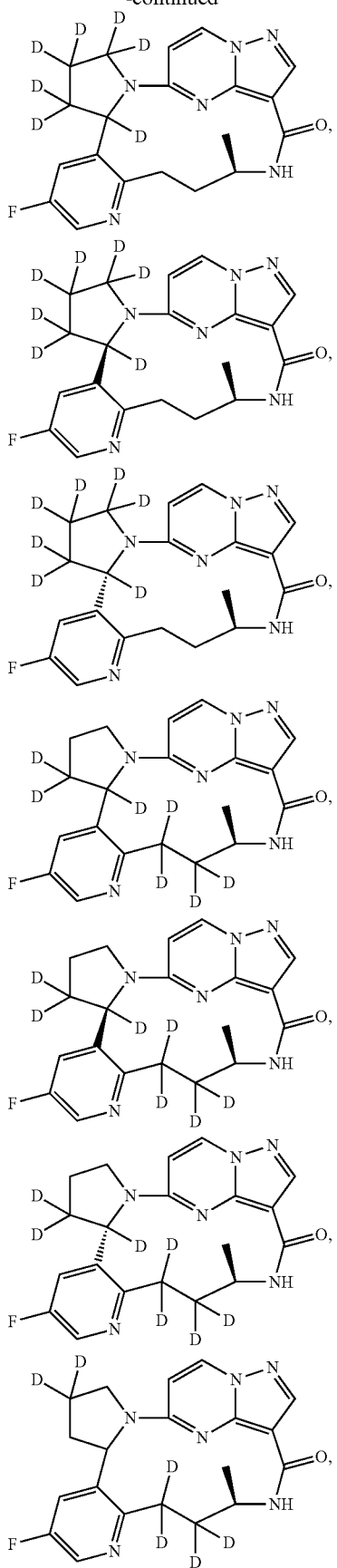

-continued
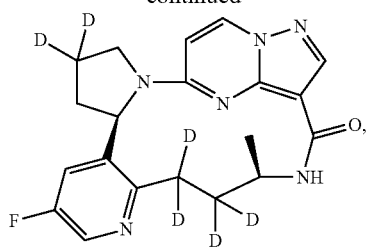
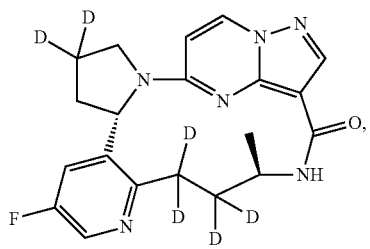
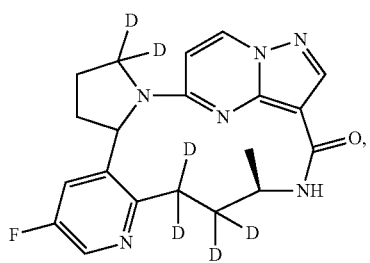
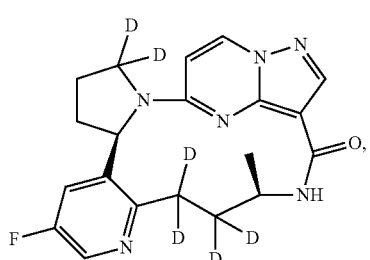
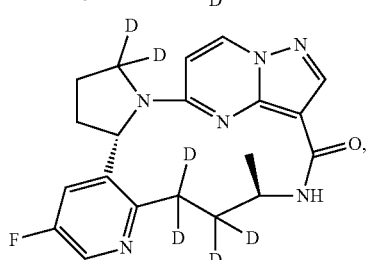
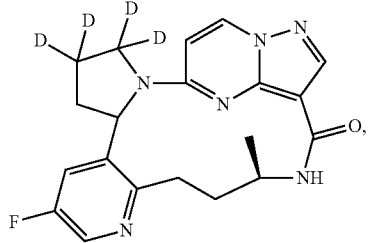
-continued
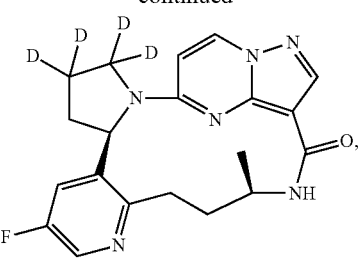
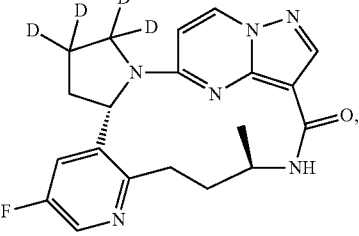
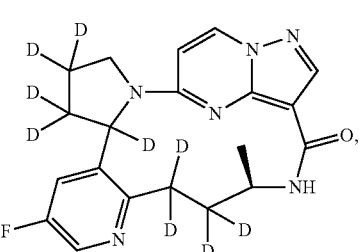
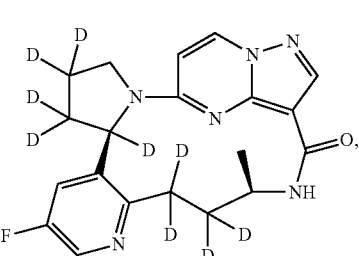
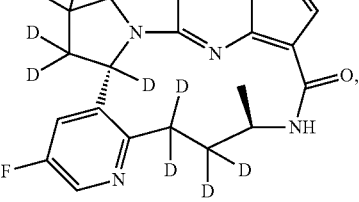
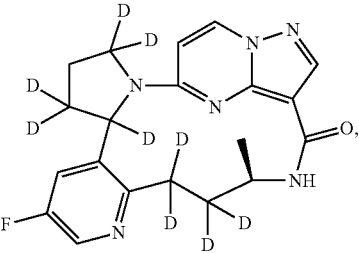

In a preferred embodiment of the invention, the compound does not include a non-deuterated compound.

Pharmaceutical Composition and Method of Administration

In another aspect, the invention provides a pharmaceutical composition comprising a compound of the invention (also referred to as "active ingredient") and a pharmaceutically acceptable excipient. In some embodiments, the pharmaceutical composition comprises an effective amount of the active ingredient. In some embodiments, the pharmaceutical composition comprises a therapeutically effective amount of the active ingredient. In some embodiments, the pharmaceutical composition comprises a prophylactically effective amount of the active ingredient.

The pharmaceutical composition of the present invention comprises a safe and effective amount of a compound of the present invention, or a pharmacologically acceptable salt thereof, and a pharmacologically acceptable excipient or carrier. By "safe and effective amount" it is meant that the amount of the compound is sufficient to significantly improve the condition without causing serious side effects. In general, the pharmaceutical composition contains from 0.5 to 2000 mg of the compound of the invention per dose, more preferably from 1 to 500 mg of the compound of the invention per dose. Preferably, the "one dose" is one capsule or tablet.

"Pharmaceutically acceptable excipient" means a non-toxic carrier, adjuvant or vehicle that does not destroy the pharmacological activity of the compound formulated together. Pharmaceutically acceptable carriers, adjuvants, or vehicles that can be used in the composition of the present invention include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolytes (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene-block polymer, polyethylene glycol and lanolin.

The pharmaceutical composition of the present invention can be prepared by combining a compound of the present invention with a suitable pharmaceutically acceptable excipient, for example, as a solid, semi-solid, liquid or gaseous preparation such as a tablet, pill, capsule, powder, granule, ointment, emulsion, suspension, solution, suppository, injection, inhalant, gel, microsphere, aerosol and the like.

Typical routes of administration of a compound of the invention or a pharmaceutical composition thereof include, but are not limited to, oral, rectal, transmucosal, enteral administration, or topical, transdermal, inhalation, parenteral, sublingual, intravaginal, intranasal, intraocular, intraperitoneal, intramuscular, subcutaneous, intravenous administration.

The pharmaceutical composition of the present invention can be produced by a method well known in the art, such as a conventional mixing method, a dissolution method, a granulation method, a dragee-producing method, a pulverization method, an emulsification method, a lyophilization method, and the like.

For oral administration, the pharmaceutical composition can be formulated by mixing the active compound with pharmaceutically acceptable excipients which are well known in the art. These excipients enable the compounds of the present invention to be formulated into tablets, pills, troches, dragees, capsules, liquids, gels, slurries, suspensions and the like for oral administration to a patient.

A solid oral composition can be prepared by a conventional method of mixing, filling or tabletting. For example, it can be obtained by mixing the active compound with a solid excipient, optionally milling the resulting mixture, adding other suitable adjuvants if necessary, and then processing the mixture into granules, to obtain the core of a tablet or dragee. Suitable adjuvants include, but are not limited to, binders, diluents, disintegrants, lubricants, glidants, sweeteners or flavoring agents, and the like. For example, microcrystalline cellulose, glucose solution, gum Arabic slurry, gelatin solution, sucrose and starch paste; talc, starch, calcium stearate or stearic acid; lactose, sucrose, starch, mannitol, sorbitol or dicalcium phosphate; silica; cross-linked hydroxymethylcellulose sodium, pregelatinized starch, sodium starch glycolate, alginic acid, corn starch, potato starch, methyl cellulose, agar, hydroxymethyl cellulose, cross-linked polyvinyl pyrrolidone and the like. The core of the dragee may optionally be coated according to methods well known in the ordinary pharmaceutical practice, especially using enteric coatings.

The pharmaceutical composition may also be suitable for parenteral administration, such as a sterile solution, suspension or lyophilized product in a suitable unit dosage form. Suitable excipients such as fillers, buffers or surfactants can be used.

A compound of the invention may be administered by any route of administration and method, for example by oral or parenteral (e.g., intravenous) administration. A therapeutically effective amount of the compound of the invention is from about 0.0001 to 20 mg/kg body weight per day, such as from 0.001 to 10 mg/kg body weight per day.

The dosage frequency of a compound of the invention is determined by the need of the individual patient, for example, once or twice daily, or more times per day. Administration may be intermittent, for example, the patient receiving a daily dose of a compound of the invention over a period of several days, followed by the patient not receiving a daily dose of the compound of the invention for a period of several days or more.

Therapeutic Indications for the Compounds of the Invention

The compounds of the invention exhibit Trk family protein tyrosine kinase inhibition and can be used to treat pain, cancers, inflammation, neurodegenerative diseases or trypanosomal infections and the like.

Some embodiments include use of a compound of the invention for treating a condition and disease that can be treated by inhibition of TrkA, TrkB, and/or TrkC kinases, e.g., a TrkA, TrkB, and/or TrkC mediated condition, such as one or more conditions described herein, including a Trk-related cancer. In some embodiments, the compounds of the invention can also be used to treat pain, including chronic and acute pain. In some embodiments, the compounds of the invention can be used to treat various types of pain, neuropathic pain, surgical pain, and pain associated with cancer, surgery, and fractures.

In some embodiments, the invention provides a method of treating or preventing inflammation in a subject, the method comprising administering to the subject a therapeutically effective amount of a compound of the invention. In one embodiment, the method comprises a method of treating the inflammation in a subject. In one embodiment, the method comprises a method of preventing the inflammation in a subject.

In some embodiments, the invention provides a method of treating a neurodegenerative disease in a subject, the method comprising administering to the subject a therapeutically effective amount of a compound of the invention. In one embodiment, the neurodegenerative disease is a demyelinating disease. In one embodiment, the neurodegenerative disease is a myelination disorder. In one embodiment, the neurodegenerative disease is multiple sclerosis. In one embodiment, the neurodegenerative disease is Parkinson's disease. In one embodiment, the neurodegenerative disease is Alzheimer's disease.

In some embodiments, the invention provides a method of treating an infectious disease in a subject, the method comprising administering to the subject a therapeutically effective amount of a compound of the invention. In one embodiment, the infectious disease is a trypanosomal infection.

In some embodiments, provided herein is a method of treating a patient diagnosed with a Trk-related cancer comprising administering to the patient a therapeutically effective amount of a compound of the invention. For example, a Trk-related cancer can be selected from the group consisting of: non-small cell lung cancer, papillary thyroid cancer, glioblastoma multiforme, acute myeloid leukemia, colorectal cancer, large cell neuroendocrine cancer, prostate cancer, colon cancer, acute myeloid leukemia, sarcoma, pediatric glioma, intrahepatic cholangiocarcinoma, hairy cell astrocytoma, low grade glioma, lung adenocarcinoma, salivary gland cancer, secretory breast cancer, fibrosarcoma, nephroma and breast cancer.

In some embodiments, the Trk-related cancer is selected from the group consisting of non-limiting examples of the TRK-related cancer include: Spitzoid melanoma, Spitz tumor (e.g., metastatic Spitz tumor), non-small cell lung cancer (NSCLC), thyroid cancer (e.g., papillary thyroid tumor (PTC)), acute myeloid leukemia (AML), sarcoma (e.g., undifferentiated sarcoma or adult soft tissue sarcoma), pediatric glioma, colorectal cancer (CRC), glioblastoma multiforme (GBM), large cell neuroendocrine cancer (LCNEC), thyroid cancer, intrahepatic cholangiocarcinoma (LCC), hairy cell astrocytoma, low grade glioma, head and neck squamous cell cancer, nephroma, melanoma, bronchial cancer, B-cell cancer, Bronchus cancer, oral or pharyngeal cancer, blood tissue cancer, cervical cancer, stomach cancer, kidney cancer, liver cancer, multiple myeloma, ovarian cancer, pancreatic cancer, salivary gland cancer, small intestine or appendix cancer, testicular cancer, urinary bladder cancer, small cell lung cancer, inflammatory myofibroblastic carcinoma, gastrointestinal stromal tumor, non-Hodgkin's lymphoma, neuroblastoma, small cell lung cancer, squamous cell cancer, esophageal-gastric cancer, skin cancer, neoplasm (e.g., melanocyte neoplasm), Spitz nevus, astrocytoma, medulloblastoma, glioma, large cell neuroendocrine tumor, bone cancer, and rectum cancer.

In some embodiments, the compounds of the invention can be used to treat a Trk-related cancer in a pediatric patient. For example, the compounds provided herein can be used to treat infantile sarcoma, neuroblastoma, congenital mesoderm nephroma, cerebral low grade glioma, and pons glioma.

In some embodiments, the compounds of the invention may be used in combination with one or more additional therapeutic agents or therapies that act by the same or different mechanisms of action for the treatment of Trk-related cancers.

In some embodiments, the compounds of the invention are inhibitors of a Trk kinase and are useful for treating, preventing or ameliorating a disease or disorder to be modulated or otherwise affected by one or more of Trk kinase domain mutants, or otherwise effective to treat, prevent or ameliorate one or more of its symptoms or causes.

In some embodiments, the Trk kinase is selected from TrkA, TrkB, or TrkC.

Point mutations in the NTRK1 gene, the NTRK2 gene, and the NTRK3 gene were found in Trk inhibitor-resistant cancer cells. Point mutations in the NTRK1/2/3 genes can produce TrkA/B/C proteins, including amino acids in wild-type TrkA/B/C proteins that are substituted with different amino acids.

The compounds of the invention may be used to treat diseases mediated by at least one point mutation in the NTRK genes that results in the expression of a Trk protein.

The compounds of the invention are useful in the manufacture of a medicament for the treatment of a disease mediated by at least one point mutation in the NTRK genes that result in the expression of a Trk protein.

In some embodiments, at least one point mutation in the NTRK genes that result in the expression of a Trk protein comprising a mutation at one or more amino acid positions can be selected from (i) at least one point mutation in the NTRK1 gene, which results in the expression of a TrkA protein comprising mutations at one or more amino acid positions selected from the group consisting of: 517, 542, 568, 573, 589, 595, 599, 600, 602, 646, 656, 657, 667, and 676, and/or (ii) at least one point mutation in the NTRK2 gene, which results in the expression of a TrkB protein comprising mutations at one or more amino acid positions selected from the group consisting of 545, 570, 596, 601, 617, 623, 624, 628, 630, 672, 682, 683, 693 and 702, and/or (iii) at least one point mutation in the NTRK3 gene, which results in the expression of a TrkC protein comprising mutations at one or more amino acid positions selected from the group consisting of: 545, 570, 596, 601, 617, 623, 624, 628, 630, 675, 685, 686, 696, and 705. In other embodiments, the Trk protein comprises one or more of the following amino acid substitutions: G517R, A542V, V573M, F589L, F589C, G595S, G595R, D596V, D596V, F600L, F646V, C656Y, C656F, L657V, G667S, G667C and Y676S. In other embodiments, the TrkB protein comprises one or more of the following amino acid substitutions: G545R, A570V, Q596E, Q596P, V601G, F617L, F617C, F617I, G623S, G623R, D624V, R630K, C682Y, C682F, L683V, G693S and G713S. In some embodiments, the TrkC protein comprises one or more of the following amino acid substitutions: G545R, A570V, F617L, G623R, D624V, C685Y, C685F, L686V and G696A. In some embodiments, the additional therapeutic agents are selected from the group consisting of therapeutic agents that target a receptor tyrosine kinase, including cabozantinib, crizotinib, erlotinib, gefitinib, imatinib, lapatinib, nilotinib, pazotinib, pertuzumab, regotinib, sunitinib and trastuzumab.

In some embodiments, the additional therapeutic agents are selected from signal transduction pathway inhibitors, including, for example, Ras-Raf-MEK-ERK pathway inhibitors (e.g., sorafenib, trimetinib, or vemurafenib), PI3K-Akt-mTOR-S6K pathway inhibitors (e.g., everolimus, rapamycin, perifosine, or sirolimus) and modulators of the apoptotic pathway (e.g., obataclax).

In some embodiments, the additional therapeutic agents are selected from the group consisting of cytotoxic chemotherapeutic agents, including, for example, arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide and vincristine.

In some embodiments, the additional therapeutic agents are selected from the group consisting of angiogenesis-targeted therapies, including, for example, aflibercept and bevacizumab.

In some embodiments, the additional therapeutic agents are selected from the group consisting of immuno-targeted agents, including, for example, aldesleukin, ipilizumab, lambrolizumab, nivolumab, and sipuleucel-T.

In some embodiments, the additional therapeutic agents are selected from agents that are effective against the downstream Trk pathway, including, for example, biopharmaceuticals that target NGF, such as NGF antibodies and panTrk inhibitors.

In some embodiments, the additional therapeutic agents or therapies are radiation therapies, including, for example, radioiodide therapy, external beam radiation, and radium 223 therapy.

In some embodiments, the additional therapeutic agents comprise any of the therapies or therapeutic agents listed above, which are the standards of care for cancer wherein the cancer has imbalance of a NTRK gene, a Trk protein, or an expression or activity or level thereof.

In some embodiments, provided herein is a method of treating cancer (e.g., a Trk-related cancer) in a patient comprising administering to the patient a compound of the invention. In some embodiments, the at least one additional therapies or therapeutic agents are selected from the group consisting of radiation therapies (e.g., radioiodide therapy, external beam radiation, or radium 223 therapy), cytotoxic chemotherapeutic agents (e.g., arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide or vincristine), tyrosine kinase-targeted therapies (e.g., afatinib, cabozantinib, cetuximab, crizotinib, darafinib, erlotinib, gefitinib, imatinib, lapatinib, nilotinib, pazopanib, pazopanib, panitumumab, pertuzumab, regorafenib, sunitinib, or trastuzumab), apoptosis regulators and signal transduction inhibitors (e.g., everolimus, perifosine, rapamycin, sorafenib, sirolimus, trimetinib, or vemurafenib), immuno-targeted therapies (e.g., aldesleukin, interferon a-2b, ipilizumab, lambrolizumab, nivolumab, prednisone, or sipuleucel-T) and angiogenesis-targeted therapies (e.g., aflibercept or bevacizumab), wherein the compound of the invention is effective in treating the cancer when combined with the additional therapies or therapeutic agents.

In some embodiments, the additional therapeutic agents are different Trk inhibitors. Non-limiting examples of other Trk inhibitors include (R)-2-phenylpyrrolidine substituted imidazopyridazine, AZD6918, GNF-4256, GTX-186, GNF-5837, AZ623, AG-879, altiratinib, CT327, AR-772, AR-523, AR-786, AR-256, AR-618, AZ-23, AZD7451, cabozantinib, CEP-701, CEP-751, PHA-739358, dovetinib, entrectinib, PLX7486, GW441756, MGCD516, ONO-5390556, PHA-848125AC, regorafenib, sorafenib, sunitinib, TSR-011, VM-902A, K252a, 4-aminopyrazolylpyrimidine and substituted pyrazolo[1,5-a]pyrimidine compounds.

These additional therapeutic agents can be administered together with one or more of the compounds provided herein as part of the same or separate dosage forms via the same or different routes of administration and based on the same or different dosing schedules according to standard drug practices known to those skilled in the art.

The compounds of the present invention have a number of advantages over non-deuterated compounds known in the art. Advantages of the present invention include: 1) the compounds and compositions employing the technical solutions of the present invention provide a more advantageous therapeutic tool for the treatment of pain, cancers, inflammation, neurodegenerative diseases or certain infectious diseases, particularly Trk-related diseases; 2) the metabolism of the compounds in the organism are improved, giving the compounds better pharmacokinetic parameter characteristics, under which circumstance the dosage can be changed and a long-acting preparation can be formed to improve the applicability; 3) the drug concentrations of the compounds in the animal are increased, and the drug efficacies are improved; and 4) certain metabolites are inhibited and the safety of the compounds is increased.

EXAMPLE

The invention is further illustrated below in conjunction with specific examples. It is to be understood that the examples are only for the purpose of illustrating the invention, and not intended to limit the scope of the invention. The experimental methods, which do not specify the specific conditions, in the following examples are usually in accordance with conventional conditions or according to the conditions recommended by the manufacturer. Parts and percentages are parts by weight and percentage by weight unless otherwise stated.

Usually, in the preparation scheme, each reaction is usually carried out in an inert solvent at room temperature to reflux temperature (e.g., 0° C. to 100° C., preferably 0° C. to 80° C.). The reaction time is usually from 0.1 to 60 hours, preferably from 0.5 to 24 hours.

Example 1: Preparation of (15R)-9-fluoro-15-methyl-2,11,16,20,21,24-hexaazapentacyclo
[16.5.2.0$^{2,6}$,0$^{7,12}$,0$^{21,25}$]pentacosane-1(24),7,9,11,18
(25),19,22-heptaene-17-one-13,13,14,14-d$_4$
(Compound 13); (6R,15R)-9-fluoro-15-methyl-2,11,
16,20,21,24-hexaazapentacyclo[16.5.2.0$^{2,6}$,0$^{7,12}$,
0$^{21,25}$]pentacosane-1(24),7,9,11,18(25),19,22-heptaene-17-one-13,13,14,14-d$_4$ (Compound L-1-a);
and (6S,15R)-9-fluoro-15-methyl-2,11,16,20,21,24-hexaazapentacyclo[16.5.2.0$^{2,6}$,0$^{7,12}$,0$^{21,25}$]pentacosane-1(24),7,9,11,18(25),19,22-heptaene-17-one-13,13,14,14-d$_4$ (Compound L-1-b)

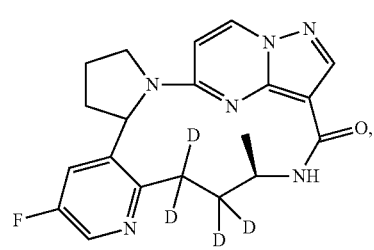

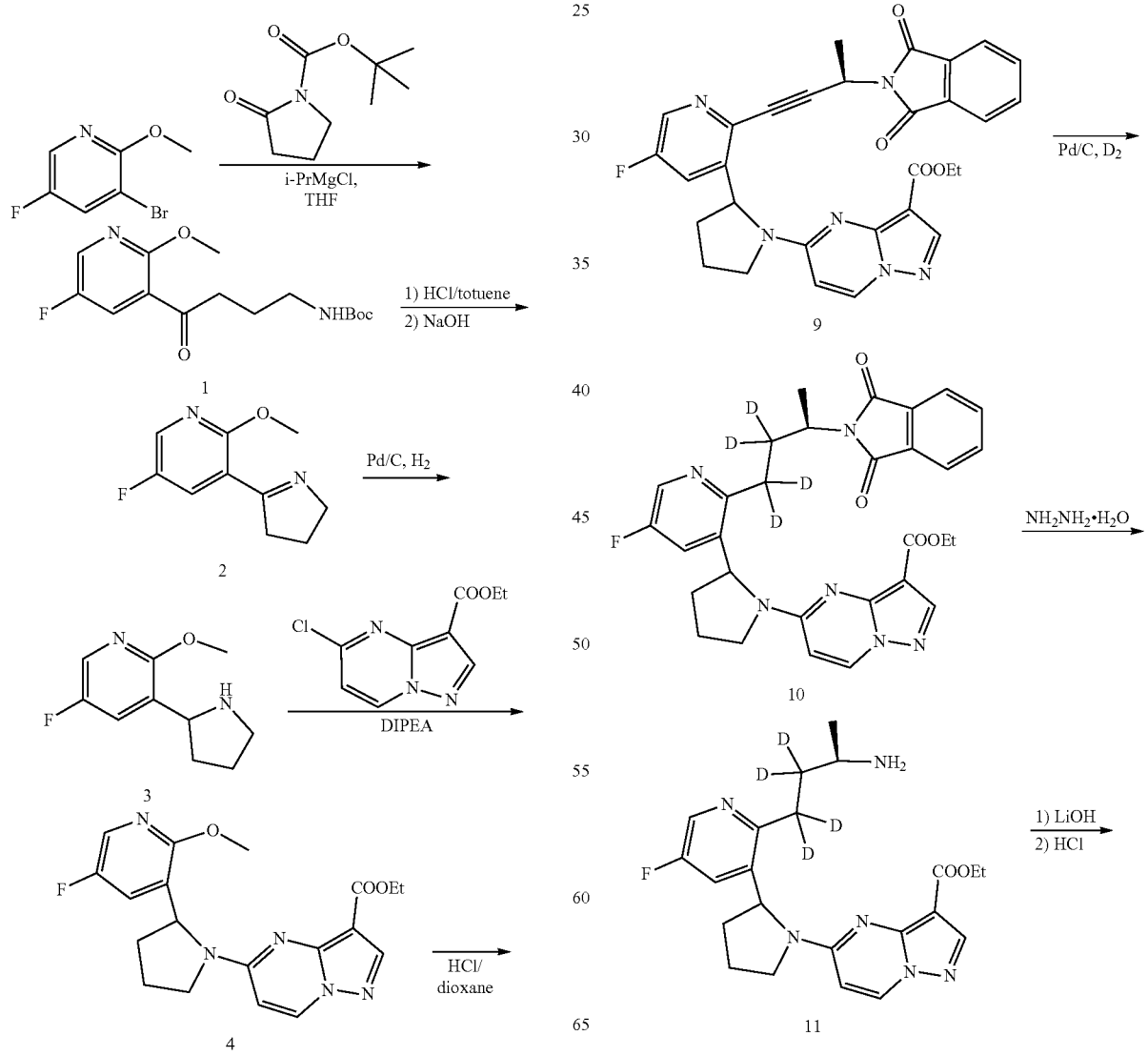
Use the following route for synthesis:

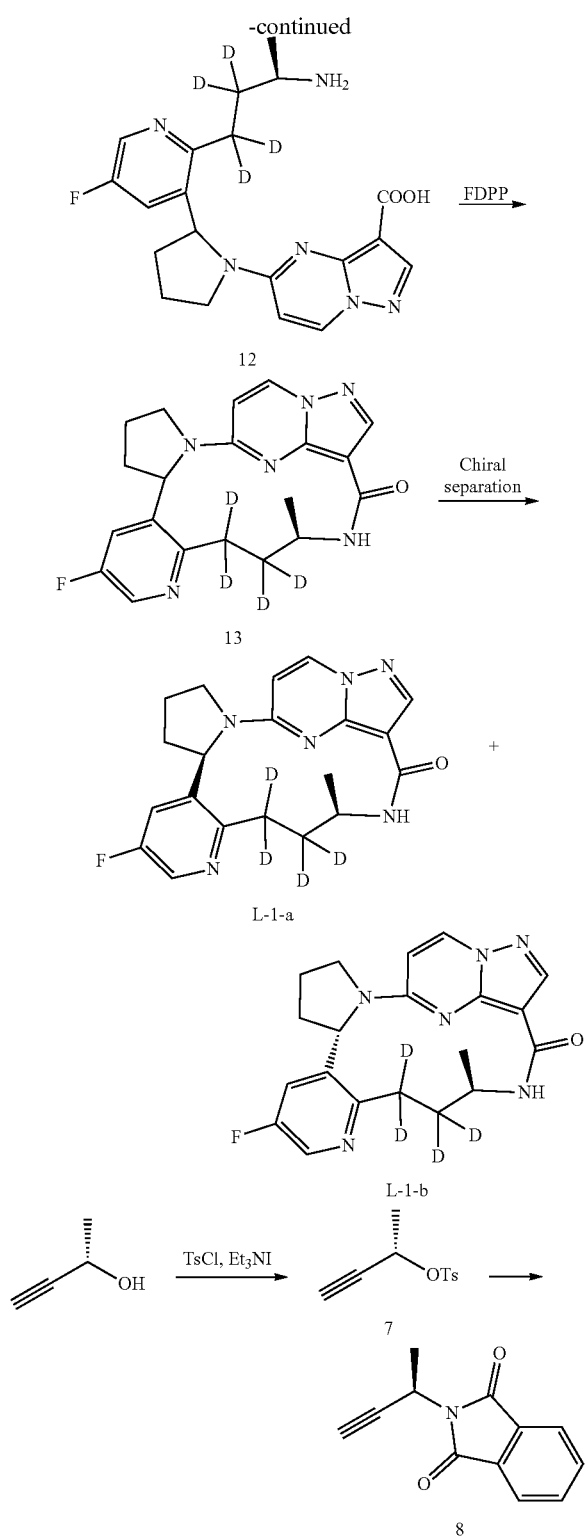

Step 1: Synthesis of Compound 1

3-Bromo-5-fluoro-2-methoxypyridine (3.09 g, 15 mmol) was dissolved in anhydrous THF (50 mL), and isopropyl magnesium chloride solution (7.0 mL, 14.0 mmol) was slowly added dropwise at 0° C. After the dropwise addition, the mixture was naturally warmed to 0° C. while stirred for 1 hour, and then a solution of N-tert-butoxycarbonyl-2-pyrrolidone (1.85 g, 10.0 mmol) in anhydrous tetrahydrofuran (10 mL) was slowly added dropwise at −15° C., and stirred at room temperature for 30 min. The reaction mixture was poured into 100 mL of a saturated aqueous solution of ammonium chloride and stirred for 10 min, and the mixture was allowed to be separated. The aqueous phase was extracted three times with 30 ml of ethyl acetate and the organic phases were combined, washed with saturated brine, and dried with anhydrous $Na_2SO_4$. Filtration, concentration and column chromatography gave 2.86 g of a pale yellow liquid as Compound 1. Yield: 61.1%. LC-MS (APCI): m/z=313.2 (M+1)$^+$.

Step 2: Synthesis of Compound 2

Compound 1 (1.87 g, 5.97 mmol) was dissolved in toluene (20 mL), 1.1 mL concentrated hydrochloric acid was added, and the mixture was warmed to 65° C. while stirred overnight. The temperature was lowered to room temperature, pH was adjusted to 14 with 2M sodium hydroxide, and stirring was continued for 1 h. The reaction was completed by TLC. The organic phase was separated, the aqueous phase was extracted three times with ethyl acetate and the organic phases were combined, washed with saturated brine, and concentrated. Column chromatography gave 624 mg of a yellow liquid as Compound 2. Yield: 53.9%. LC-MS (APCI): m/z=195.1 (M+1)$^+$.

Step 3: Synthesis of Compound 3

Compound 2 (624 mg, 3.21 mmol) was dissolved in anhydrous methanol (10 mL), and then Pd/C (50 mg) was added for hydrogenation overnight at room temperature. After filtration, the residue was washed with 20 mL of ethyl acetate, and the filtrate was concentrated to give 620 mg of a colorless oily liquid as Compound 3. Yield: 98.5%. LC-MS (APCI): m/z=197.3 (M+1)$^+$.

Step 4: Synthesis of Compound 4

Compound 3 (162 mg, 0.82 mmol) and ethyl 5-chloropyrazolo[1,5-a]pyrimidine-3-carboxylate (185.4 mg, 0.82 mmol) were dissolved in anhydrous ethanol (6 mL) and DIPEA (N,N-diisopropylethylamine, 423.9 mg, 3.28 mmol) was added at room temperature, and heated to reflux for 30 min. The reaction solution was concentrated and subjected to column chromatography (PE/EA, 30% to 50%) to give 204 mg of a pale yellow solid powder as Compound 4. Yield: 64.7%. LC-MS (APCI): m/z=386.5 (M+1)$^+$.

Step 5: Synthesis of Compound 5

Compound 4 (200 mg, 0.52 mmol) was dissolved in 4M hydrogen chloride in dioxane (5 mL, 20 mmol), and then sealed and heated to 110° C. while stirred for 24 h. After the reaction was completed by TLC, the mixture was concentrated to remove the solvent, and used directly in the next step.

Step 6: Synthesis of Compound 6

Compound 5 (1.78 g, 4.79 mmol) and N-phenylbis(trifluoromethanesulfonyl)imide (1.88 g, 5.27 mmol) were dispersed in 25 mL of anhydrous DMF, and triethylamine (581.6 mg, 5.75 mmol) was added. The reaction was stirred at room temperature under nitrogen atmosphere. After the reaction was completed by TLC, the mixture was diluted with water, and extracted with ethyl acetate three times. The organic phases were combined, washed with saturated brine, and concentrated. Column chromatography (PE/EA: 50% to 66%) gave 2.05 g of a yellow solid powder as Compound 6. Yield: 85%. LC-MS (APCI): m/z=504.3 (M+1)$^+$.

Step 7: Synthesis of Compound 7

(S)-3-butyn-2-ol (280 mg, 4.0 mmol) was dissolved in 10 mL of anhydrous dichloromethane, and then triethylamine (445.2 mg, 4.4 mmol) was added, and the solution of p-toluenesulfonyl chloride (762.6 mg, 4.0 mmol) in dichloromethane (5 mL) was slowly added dropwise at 0° C. under nitrogen atmosphere. After the reaction was completed by TLC, the mixture was diluted with dichloromethane, washed successively with water and saturated brine, and then concentrated. Column chromatography gave 806 mg of an off white solid as Compound 7. Yield: 90%.

Step 8: Synthesis of Compound 8

Compound 7 (448 mg, 2.0 mmol) was dissolved in 10 mL of anhydrous DMF, and potassium phthalimide (370.4 mg, 2.0 mmol) was added, and the reaction was stirred overnight at room temperature. After the reaction was completed by TLC, the mixture was diluted with water, the aqueous phase was extracted three times with ethyl acetate and the organic phases were combined, washed with saturated brine, and concentrated. Column chromatography gave 243 mg of a white solid as Compound 8. Yield: 61%. LC-MS (APCI): m/z=200.2 (M+1)$^+$.

Step 9: Synthesis of Compound 9

Compound 6 (503.1 mg, 1.0 mmol) and Compound 8 (199 mg, 1.0 mmol) were dissolved in 25 mL of anhydrous tetrahydrofuran, and Pd(PPh$_3$)$_2$Cl$_2$ (35 mg, 0.05 mmol) and CuI (19 mg, 0.1 mmol) were added under nitrogen atmosphere. Triethylamine (202.4 mg, 2.0 mmol) was added in one portion at room temperature and stirred at room temperature overnight. After the reaction was completed by TLC, the mixture was concentrated to remove the solvent. Column chromatography gave 287 mg of a pale yellow solid powder as Compound 9. Yield: 52%. LC-MS (APCI): m/z=553.3 (M+1)$^+$.

Step 10: Synthesis of Compound 10

Compound 9 (287 mg, 0.52 mmol) was dissolved in 10 ml of deuterated methanol, and a catalytic amount of Pd/C was added. The reaction was stirred at room temperature for 2-4 h under deuterium atmosphere. After the reaction was completed by TLC, the catalyst was removed by filtration and the filtrate was concentrated to dryness and directly used in the next step.

Step 11: Synthesis of Compound 11

Compound 10 (287 mg, 0.52 mmol) was dissolved in 10 ml of methanol, and hydrazine hydrate (130 mg, 2.6 mmol) was added, and the mixture was heated to reflux for 1-2 h. After the reaction was completed by TLC, the mixture was concentrated to remove the solvent and purified by column chromatography to obtain 181.2 mg of a pale yellow solid. Yield: 81%. LC-MS (APCI): m/z=431.2 (M+1)$^+$.

Step 12: Synthesis of Compound 12

Compound 11 (224 mg, 0.52 mmol) was dissolved in 3 ml of methanol and 2 ml of water, and lithium hydroxide (109.2 mg, 2.6 mmol) was added. The temperature was raised to 50° C., and the reaction was stirred for 4-6 h. After the reaction was completed by TLC, the mixture was cooled to room temperature. Diluted hydrochloric acid was added to adjust the pH to acidity. The mixture was concentrated to remove the solvent, and directly used in the next step.

Step 13: Synthesis of Compound 13

The product obtained in the above step was dissolved in 20 ml of anhydrous DMF, and FDPP (pentafluorophenyldiphenyl phosphate, 240 mg, 0.62 mmol) and DIPEA (336 mg, 2.6 mmol) were added at room temperature, and the reaction was stirred overnight under nitrogen atmosphere. After the reaction was completed by TLC, the mixture was diluted with water, and extracted 3-4 times with ethyl acetate. The organic phases were combined, washed with saturated brine, and concentrated. Column chromatography gave 73.9 mg of an off white solid as Compound 13. Yield: 37%. LC-MS (APCI): m/z=385.3 (M+1)$^+$. $^1$H NMR (400 MHz, DMSO) δ 8.87 (s, 1H), 8.42 (s, 1H), 8.33 (s, 1H), 8.04 (d, J=2.3 Hz, 1H), 7.52 (s, 1H), 6.74 (d, J=2.3 Hz, 1H), 4.38 (t, 1H), 3.61 (dd, J=17.0, 9.3 Hz, 2H), 3.15 (m, 2H), 2.06 (m, 2H), 2.01-1.65 (m, 2H), 1.22 (d, J=4.5 Hz, 2H).

Step 14: Preparation of Compounds L-1-a and L-1-b

The racemic compound 13 was separated using a chiral preparative chromatographic column to give Compounds L-1-a and L-1-b.

Example 2: Preparation of (15R)-9-fluoro-15-methyl-2,11,16,20,21,24-hexaazapentacyclo[16.5.2.0$^{2,6}$,0$^{7,12}$,0$^{21,25}$]pentacosane-1(24),7,9,11,18(25),19,22-heptaene-17-one-5,5,6-d$_3$ (Compound 22); (6R,15R)-9-fluoro-15-methyl-2,11,16,20,21,24-hexaazapentacyclo[16.5.2.0$^{2,6}$,0$^{7,12}$,0$^{21,25}$]pentacosane-1(24),7,9,11,18(25),19,22-heptaene-17-one-5,5,6-d$_3$ (Compound L-2-a); and (6S,15R)-9-fluoro-15-methyl-2,11,16,20,21,24-hexaazapentacyclo[16.5.2.0$^{2,6}$,0$^{7,12}$,0$^{21,25}$]pentacosane-1(24),7,9,11,18(25),19,22-heptaene-17-one-5,5,6-d$_3$ (Compound L-2-b)

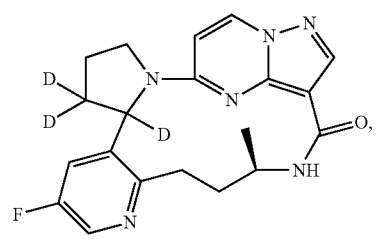

22

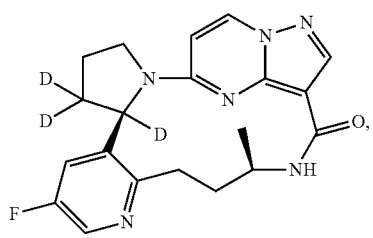

L-2-a

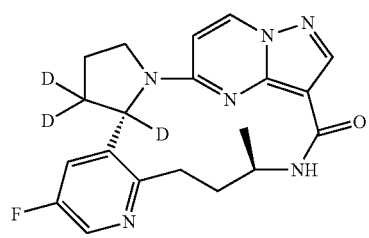

L-2-b

Use the following route for synthesis:

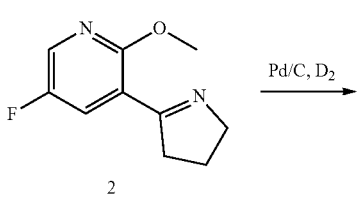

2

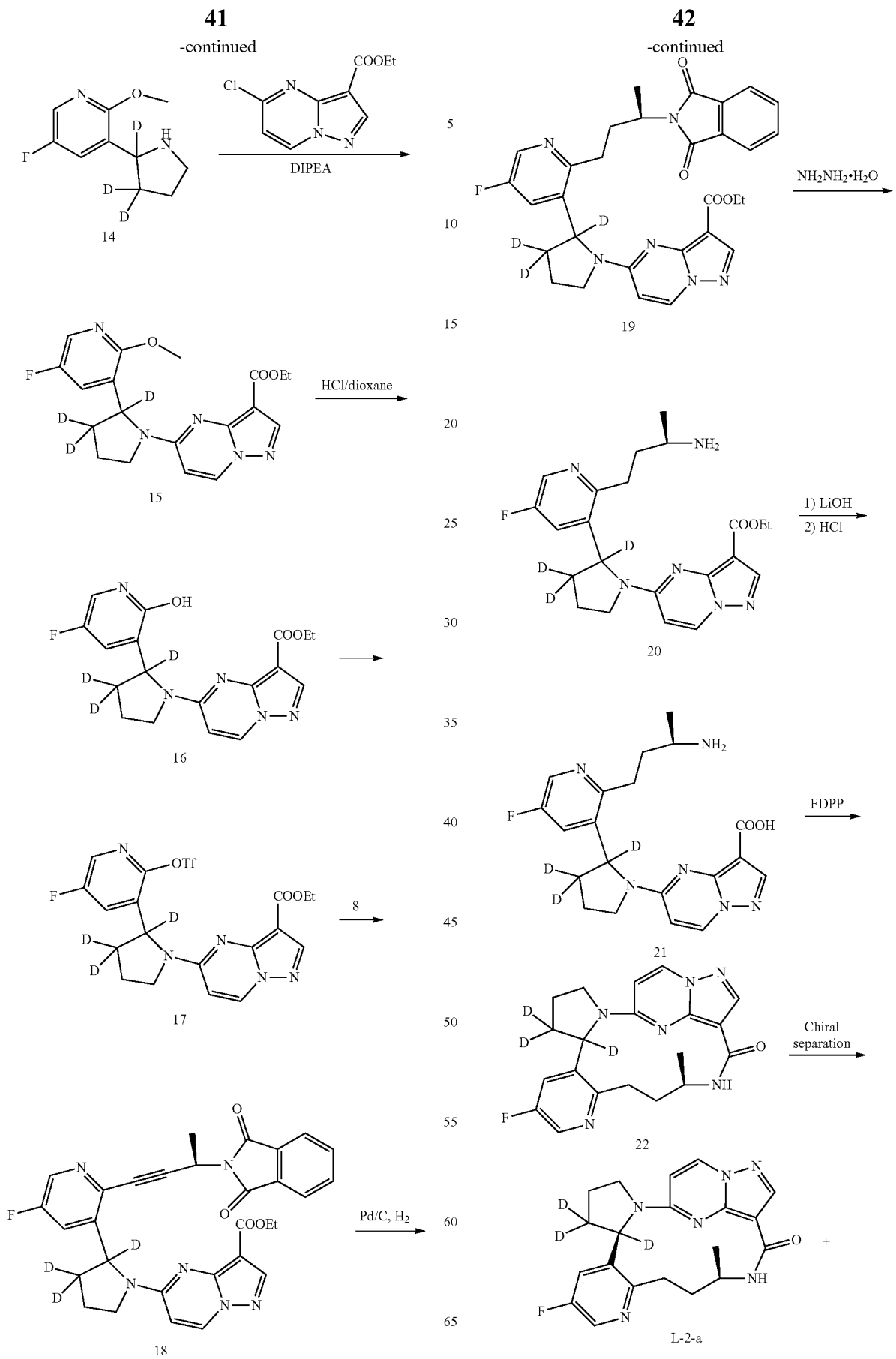

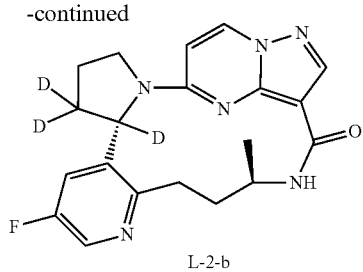

L-2-b

Step 1: Synthesis of Compound 14

Compound 2 (1.25 g, 6.42 mmol) was dissolved in deuterated methanol (20 mL), and Pd/C (100 mg) was added for hydrogenation under deuterium atmosphere overnight at room temperature. After filtration, the residue was washed with 20 mL of ethyl acetate, and the filtrate was concentrated to give 1.21 g of a colorless oily liquid as Compound 14. Yield: 95%. LC-MS (APCI): m/z=200.1 (M+1)$^+$.

Step 2: Synthesis of Compound 15

Compound 14 (326 mg, 1.64 mmol) and ethyl 5-chloro-pyrazolo[1,5-a]pyrimidine-3-carboxylate (370.8 mg, 1.64 mmol) were dissolved in anhydrous ethanol (15 mL) and DIPEA (847.8 mg, 6.56 mmol) was added at room temperature, and heated to reflux for 30 min. The reaction solution was concentrated and subjected to column chromatography (PE/EA, 30% to 50%) to give 445 mg of a pale yellow solid powder as Compound 15. Yield: 70%. LC-MS (APCI): m/z=389.5 (M+1)$^+$.

Step 3: Synthesis of Compound 16

Compound 15 (400 mg, 1.03 mmol) was dissolved in 4M hydrogen chloride in dioxane (8 ml, 32 mmol), and then sealed and heated to 110° C. while stirred for 24 h. After the reaction was completed by TLC, the mixture was concentrated to remove the solvent, and used directly in the next step.

Step 4: Synthesis of Compound 17

Compound 16 (1.79 g, 4.79 mmol) and N-phenylbis(trifluoromethanesulfonyl)imide (1.88 g, 5.27 mmol) were dispersed in 25 mL of anhydrous DMF, and triethylamine (581.6 mg, 5.75 mmol) was added. The reaction was stirred overnight at room temperature under nitrogen atmosphere. After the reaction was completed by TLC, the mixture was diluted with water, and extracted with ethyl acetate three times. The organic phases were combined, washed with saturated brine, and concentrated. Column chromatography (PE/EA: 50% to 66%) gave 2.05 g of a yellow solid powder as Compound 17. Yield: 85%. LC-MS (APCI): m/z=507.8 (M+1)$^+$.

Step 5: Synthesis of Compound 18

Compound 17 (506.1 mg, 1.0 mmol) and Compound 8 (199 mg, 1.0 mmol) were dissolved in 25 mL of anhydrous tetrahydrofuran, and Pd(PPh$_3$)$_2$Cl$_2$ (35 mg, 0.05 mmol) and CuI (19 mg, 0.1 mmol) were added under nitrogen atmosphere. Triethylamine (202.4 mg, 2.0 mmol) was added in one portion at room temperature and stirred at room temperature overnight. After the reaction was completed by TLC, the mixture was concentrated to remove the solvent. Column chromatography gave 289 mg of a pale yellow solid powder as Compound 18. Yield: 52%. LC-MS (APCI): m/z=556.3 (M+1)$^+$.

Step 6: Synthesis of Compound 19

Compound 18 (289 mg, 0.52 mmol) was dissolved in a mixed solution of 5 ml of methanol and 5 ml of tetrahydrofuran, and a catalytic amount of Pd/C was added. The reaction was stirred at room temperature for 2-4 h under hydrogen atmosphere. After the reaction was completed by TLC, the catalyst was removed by filtration and the filtrate was concentrated to dryness and directly used in the next step.

Step 7: Synthesis of Compound 20

Compound 20 (289 mg, 0.52 mmol) was dissolved in 10 ml of methanol, and hydrazine hydrate (130 mg, 2.6 mmol) was added, and the mixture was heated to reflux for 1-2 h. After the reaction was completed by TLC, the mixture was concentrated to remove the solvent and purified by column chromatography to obtain 181.2 mg of a pale yellow solid. Yield: 81%. LC-MS (APCI): m/z=430.2 (M+1)$^+$.

Step 8: Synthesis of Compound 21

Compound 20 (223 mg, 0.52 mmol) was dissolved in 3 ml of methanol and 2 ml of water, and lithium hydroxide (109.2 mg, 2.6 mmol) was added. The temperature was raised to 50° C., and the reaction was stirred for 4-6 h. After the reaction was completed by TLC, the mixture was cooled to room temperature. Diluted hydrochloric acid was added to adjust the pH to acidity. The mixture was concentrated to remove the solvent, and directly used in the next step.

Step 9: Synthesis of Compound 22

The product obtained in the above step was dissolved in 20 ml of anhydrous DMF, and FDPP (240 mg, 0.62 mmol) and DIPEA (336 mg, 2.6 mmol) were added at room temperature, and the reaction was stirred overnight under nitrogen atmosphere. After the reaction was completed by TLC, the mixture was diluted with water, and extracted 3-4 times with ethyl acetate. The organic phases were combined, washed with saturated brine, and concentrated. Column chromatography gave 65 mg of an off white solid as Compound 22. Yield: 32.5%.

Step 10: Preparation of Compounds L-2-a and L-2-b

The racemic compound 22 was separated using a chiral preparative chromatographic column to give Compounds L-2-a and L-2-b.

Example 3: Preparation of (15R)-9-fluoro-15-methyl-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-5,5,6,13,13,14,14-d$_7$ (compound 26); (6R,15R)-9-fluoro-15-methyl-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-5,5,6,13,13,14,14-d$_7$ (Compound L-3-a); and (6S,15R)-9-fluoro-15-methyl-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-5,5,6,13,13,14,14-d$_7$ (Compound L-3-b)

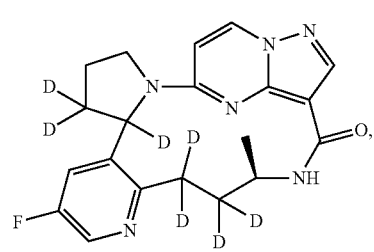

26

-continued

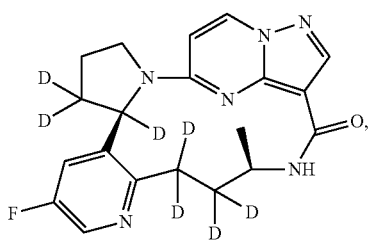
L-3-a

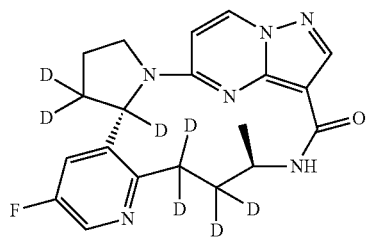
L-3-b

Use the following route for synthesis:

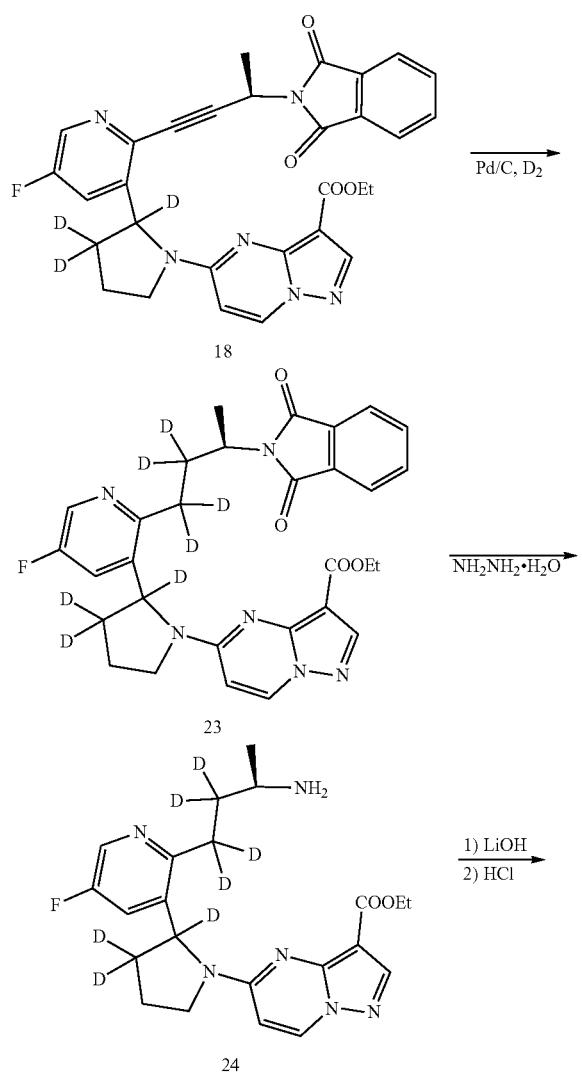

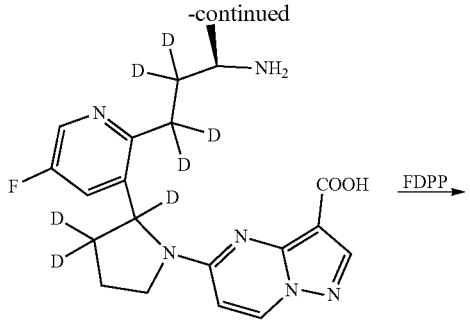

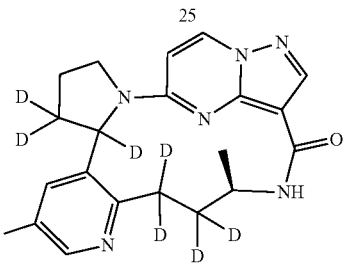

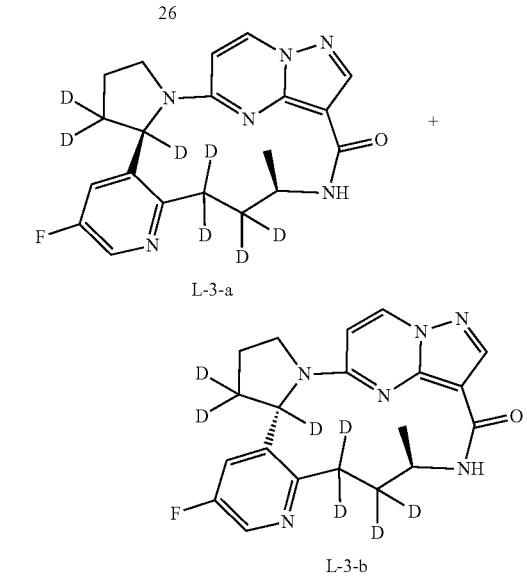

Step 1: Synthesis of Compound 23

Compound 18 (289 mg, 0.52 mmol) was dissolved in 10 ml of deuterated methanol, and a catalytic amount of Pd/C was added. The reaction was stirred at room temperature for 2-4 h under deuterium atmosphere. After the reaction was completed by TLC, the catalyst was removed by filtration and the filtrate was concentrated to dryness and directly used in the next step.

Step 2: Synthesis of Compound 24

Compound 23 (290 mg, 0.52 mmol) was dissolved in 10 ml of methanol, and hydrazine hydrate (130 mg, 2.6 mmol) was added, and the mixture was heated to reflux for 1-2 h. After the reaction was completed by TLC, the mixture was concentrated to remove the solvent and purified by column chromatography to obtain 153.2 mg of a pale yellow solid. Yield: 68%. LC-MS (APCI): m/z=434.2 $(M+1)^+$.

Step 3: Synthesis of Compound 25

Compound 24 (225.1 mg, 0.52 mmol) was dissolved in 3 ml of methanol and 2 ml of water, and lithium hydroxide (109.2 mg, 2.6 mmol) was added. The temperature was raised to 50° C., and the reaction was stirred for 4-6 h. After the reaction was completed by TLC, the mixture was cooled to room temperature. Diluted hydrochloric acid was added to adjust the pH to acidity. The mixture was concentrated to remove the solvent, and directly used in the next step.

Step 4: Synthesis of Compound 26

The product obtained in the above step was dissolved in 20 ml of anhydrous DMF, and FDPP (240 mg, 0.62 mmol) and DIPEA (336 mg, 2.6 mmol) were added at room temperature, and the reaction was stirred overnight under nitrogen atmosphere. After the reaction was completed by TLC, the mixture was diluted with water, and extracted 3-4 times with ethyl acetate. The organic phases were combined, washed with saturated brine, and concentrated. Column chromatography gave 90.55 mg of an off white solid as Compound 26. Yield: 45%. LC-MS (APCI): m/z=388.3 $(M+1)^+$.

Step 5: Preparation of Compounds L-3-a and L-3-b

The racemic compound 26 was separated using a chiral preparative chromatographic column to give Compounds L-3-a and L-3-b.

Example 4: Preparation of (15R)-9-fluoro-15-methyl-2,11,16,20,21,24-hexaazapentocyclo [16.5.2.0$^{2,6}$,0$^{7,12}$,0$^{21,25}$]pentacosane-1(24),7,9,11,18 (25),19,22-heptaene-17-one-4,4-d$_2$ (compound 40); (6R,15R)-9-fluoro-15-methyl-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-4,4-d$_2$ (Compound L-4-a); and (6S,15R)-9-fluoro-15-methyl-2,11,16,20,21,24-hexaazapentocyclo [16.5.2.0$^{2,6}$,0$^{7,12}$,0$^{21,25}$]pentacosane-1(24),7,9,11,18 (25),19,22-heptaene-17-one-4,4-d$_2$ (Compound L-4-b)

Use the following route for synthesis:

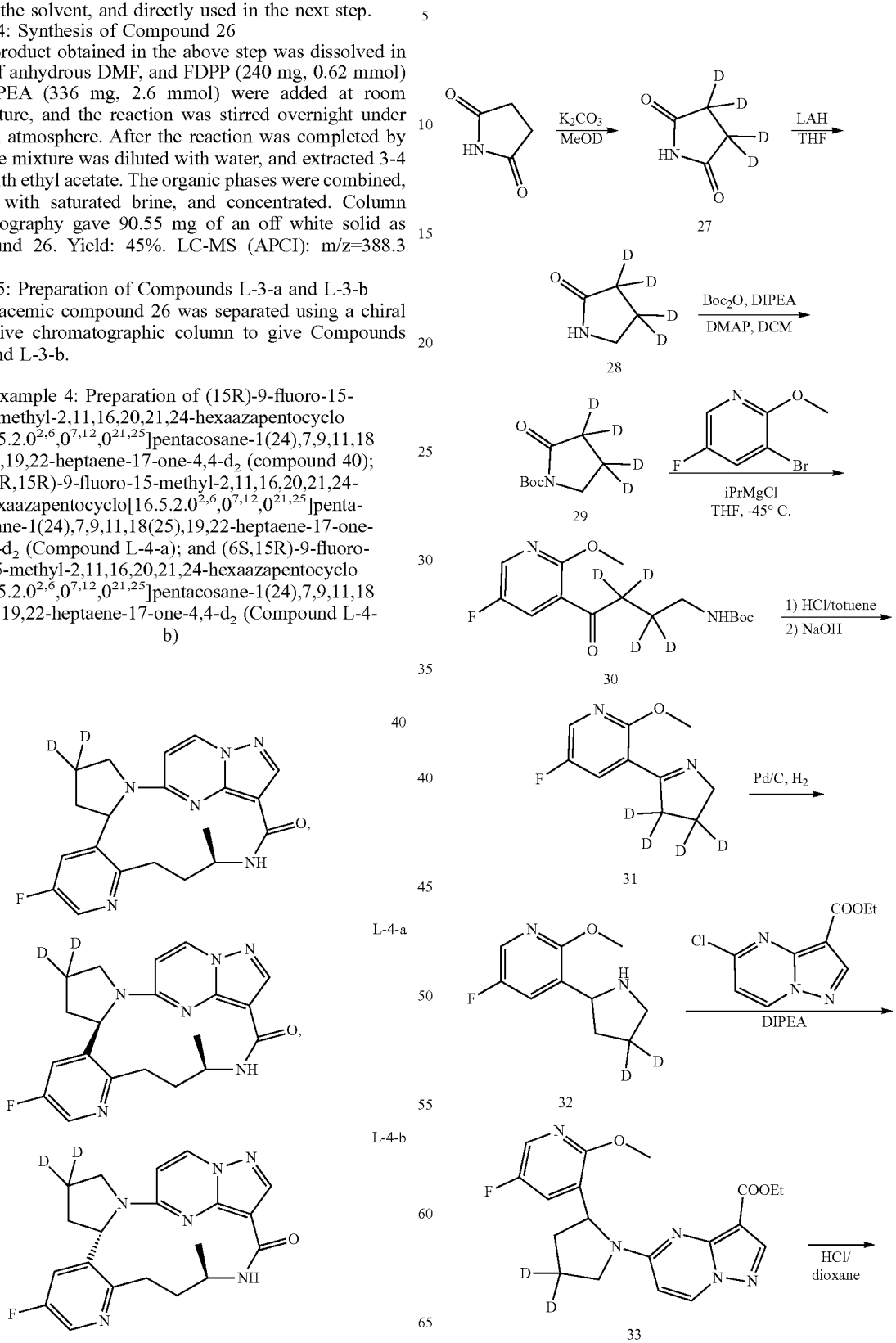

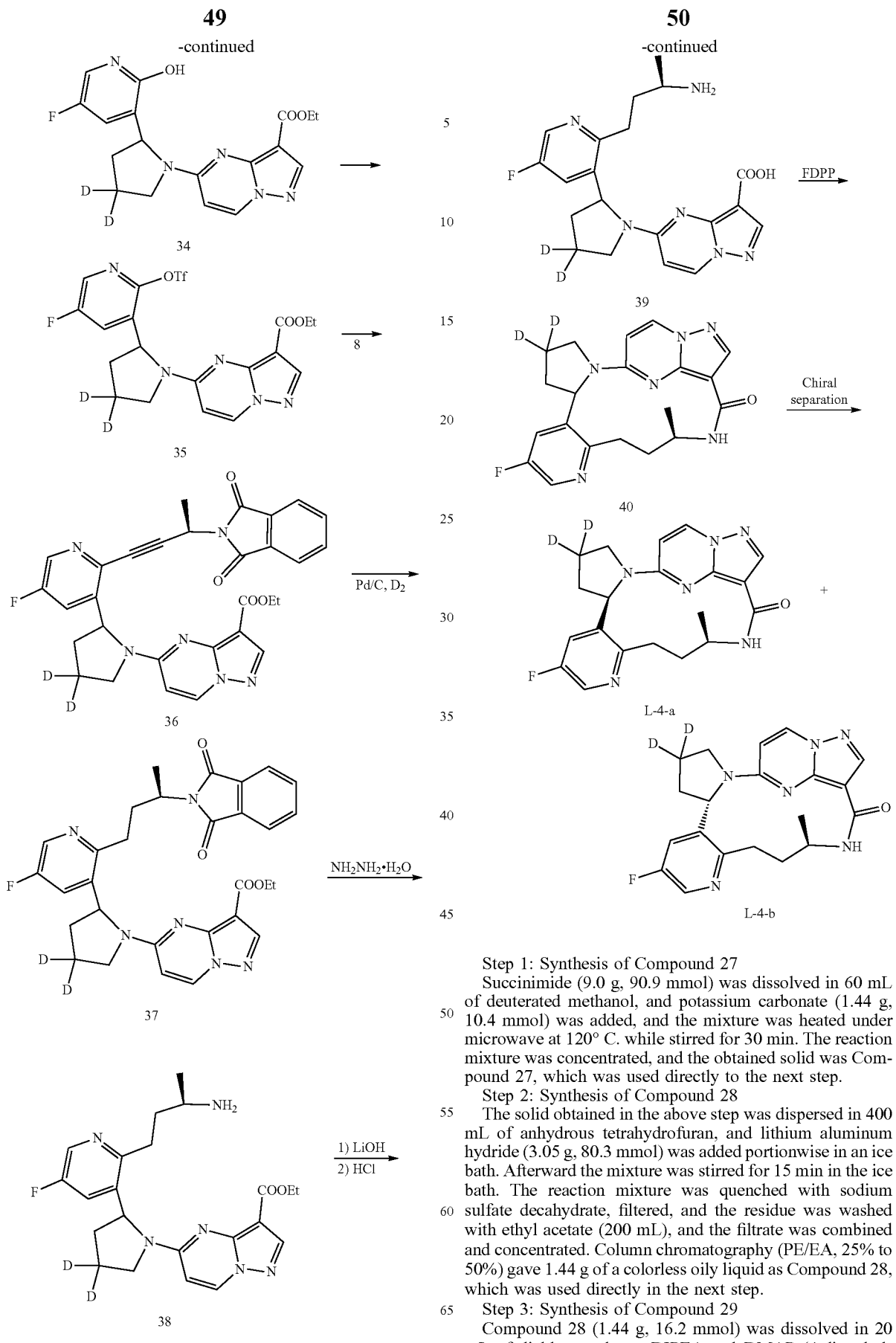

Step 1: Synthesis of Compound 27

Succinimide (9.0 g, 90.9 mmol) was dissolved in 60 mL of deuterated methanol, and potassium carbonate (1.44 g, 10.4 mmol) was added, and the mixture was heated under microwave at 120° C. while stirred for 30 min. The reaction mixture was concentrated, and the obtained solid was Compound 27, which was used directly to the next step.

Step 2: Synthesis of Compound 28

The solid obtained in the above step was dispersed in 400 mL of anhydrous tetrahydrofuran, and lithium aluminum hydride (3.05 g, 80.3 mmol) was added portionwise in an ice bath. Afterward the mixture was stirred for 15 min in the ice bath. The reaction mixture was quenched with sodium sulfate decahydrate, filtered, and the residue was washed with ethyl acetate (200 mL), and the filtrate was combined and concentrated. Column chromatography (PE/EA, 25% to 50%) gave 1.44 g of a colorless oily liquid as Compound 28, which was used directly in the next step.

Step 3: Synthesis of Compound 29

Compound 28 (1.44 g, 16.2 mmol) was dissolved in 20 mL of dichloromethane, DIPEA and DMAP (4-dimethylaminopyridine) were added at room temperature, and Boc₂O (di-tert-butyl dicarbonate) was slowly added dropwise in an ice water bath. Afterward the mixture was stirred at room temperature overnight. The reaction mixture was concentrated and subjected to column chromatography to give 586 g of a brown oily liquid as Compound 29, which was used directly in the next step.

Step 4: Synthesis of Compound 30

3-Bromo-5-fluoro-2-methoxypyridine (3.09 g, 15 mmol) was dissolved in anhydrous THF (50 mL), and isopropyl magnesium chloride solution (7.0 mL, 14.0 mmol) was slowly added dropwise at 0° C. Afterward the mixture was naturally warmed to 0° C. while stirred for 1 h, and then a solution of Compound 29 (1.89 g, 10.0 mmol) in anhydrous tetrahydrofuran (10 mL) was slowly added dropwise at −15° C., and then stirred at room temperature for 30 min. The reaction mixture was poured into 100 mL of a saturated aqueous solution of ammonium chloride and stirred for 10 min, and the mixture was allowed to be separated. The aqueous phase was extracted three times with 30 mL of ethyl acetate and the organic phases were combined, washed with saturated brine, and dried with anhydrous Na₂SO₄. Filtration, concentration and column chromatography gave Compound 30 as a pale yellow liquid.

Step 5: Synthesis of Compound 31

Compound 30 (1.88 g, 5.97 mmol) was dissolved in toluene (20 mL), and 1.1 mL of concentrated hydrochloric acid was added, and the mixture was warmed to 65° C., and the reaction was stirred overnight. Then the temperature was lowered to room temperature, and pH was adjusted to 14 with 2M sodium hydroxide, and then stirring was continued for 1 hour. The reaction was completed by TLC. The organic phase was separated, and the aqueous phase was extracted with ethyl acetate three times. The organic phases were combined, washed with saturated brine, concentrated, and then purified by column chromatography to give 650 mg of a yellow liquid as Compound 31.

Step 6: Synthesis of Compound 32

Compound 31 (650 mg, 3.28 mmol) was dissolved in anhydrous methanol (10 mL). Pd/C (50 mg) was added for hydrogenation at room temperature overnight. After filtration, the residue was washed with 20 mL of ethyl acetate, and the filtrate was concentrated to give 650 mg of a colorless oily liquid as Compound 32.

Step 7: Synthesis of Compound 33

Compound 32 (162 mg, 0.82 mmol) and ethyl 5-chloropyrazolo[1,5-a]pyrimidine-3-carboxylate (185.4 mg, 0.82 mmol) were dissolved in anhydrous ethanol (6 mL) and DIPEA (423.9 mg, 3.28 mmol) was added at room temperature, and heated to reflux for 30 min. The reaction solution was concentrated and subjected to column chromatography (PE/EA, 30% to 50%) to give a pale yellow solid powder as Compound 33.

Step 8: Synthesis of Compound 34

Compound 33 (201 mg, 0.52 mmol) was dissolved in 4M hydrogen chloride in dioxane (5 ml, 20 mmol), and then sealed and heated to 110° C. while stirred for 24 h. After the reaction was completed by TLC, the mixture was concentrated to remove the solvent, and used directly in the next step.

Step 9: Synthesis of Compound 35

Compound 34 (1.79 g, 4.79 mmol) and N-phenylbis(trifluoromethanesulfonyl)imide (1.88 g, 5.27 mmol) were dispersed in 25 mL of anhydrous DMF, and triethylamine (581.6 mg, 5.75 mmol) was added. The reaction was stirred at room temperature under nitrogen atmosphere. After the reaction was completed by TLC, the mixture was diluted with water, and extracted with ethyl acetate three times. The organic phases were combined, washed with saturated brine, and concentrated. Column chromatography (PE/EA: 50% to 66%) gave a yellow solid powder as Compound 35.

Step 10: Synthesis of Compound 36

Compound 35 (503.1 mg, 1.0 mmol) and Compound 8 (199 mg, 1.0 mmol) were dissolved in 25 mL of anhydrous tetrahydrofuran, and Pd(PPh₃)₂Cl₂ (35 mg, 0.05 mmol) and CuI (19 mg, 0.1 mmol) were added under nitrogen atmosphere. Triethylamine (202.4 mg, 2.0 mmol) was added in one portion at room temperature and stirred at room temperature overnight. After the reaction was completed by TLC, the mixture was concentrated to remove the solvent. Column chromatography gave a pale yellow solid powder as Compound 36.

Step 11: Synthesis of Compound 37

Compound 36 (288 mg, 0.52 mmol) was dissolved in a mixed solution of 5 ml of methanol and 5 ml of tetrahydrofuran, and a catalytic amount of Pd/C was added. The reaction was stirred at room temperature for 2-4 h under hydrogen atmosphere. After the reaction was completed by TLC, the catalyst was removed by filtration and the filtrate was concentrated to dryness and directly used in the next step.

Step 12: Synthesis of Compound 38

Compound 37 (289 mg, 0.52 mmol) was dissolved in 10 ml of methanol, and hydrazine hydrate (130 mg, 2.6 mmol) was added, and the mixture was heated to reflux for 1-2 h. After the reaction was completed by TLC, the mixture was concentrated to remove the solvent and purified by column chromatography to obtain a pale yellow solid as Compound 38.

Step 13: Synthesis of Compound 39

Compound 38 (224 mg, 0.52 mmol) was dissolved in 3 ml of methanol and 2 ml of water, and lithium hydroxide (109.2 mg, 2.6 mmol) was added. The temperature was raised to 50° C., and the reaction was stirred for 4-6 h. After the reaction was completed by TLC, the mixture was cooled to room temperature. Diluted hydrochloric acid was added to adjust the pH to acidity. The mixture was concentrated to remove the solvent, and directly used in the next step.

Step 14: Synthesis of Compound 40

The product obtained in the above step was dissolved in 20 ml of anhydrous DMF, and FDPP (240 mg, 0.62 mmol) and DIPEA (336 mg, 2.6 mmol) were added at room temperature, and the reaction was stirred overnight under nitrogen atmosphere. After the reaction was completed by TLC, the mixture was diluted with water, and extracted 3-4 times with ethyl acetate. The organic phase was combined, washed with saturated brine, and concentrated. Column chromatography gave an off white solid as Compound 40.

Step 15: Preparation of Compounds L-4-a and L-4-b

The racemic compound 40 was separated using a chiral preparative chromatographic column to give Compounds L-4-a and L-4-b.

Example 5: Preparation of (15R)-9-fluoro-15-methyl-2,11,16,20,21,24-hexaazapentocyclo[16.5.2.0²,⁶,0⁷,¹²,0²¹,²⁵]pentacosane-1(24),7,9,11,18(25),19,22-heptaene-17-one-3,3-d₂ (compound 53); (6R,15R)-9-fluoro-15-methyl-2,11,16,20,21,24-hexaazapentocyclo[16.5.2.0²,⁶,0⁷,¹²,0²¹,²⁵]pentacosane-1(24),7,9,11,18(25),19,22-heptaene-17-one-3,3-d₂ (Compound L-5-a); and (6S,15R)-9-fluoro-15-methyl-2,11,16,20,21,24-hexaazapentocyclo[16.5.2.0²,⁶,0⁷,¹²,0²¹,²⁵]pentacosane-1(24),7,9,11,18(25),19,22-heptaene-17-one-3,3-d₂ (Compound L-5-b)
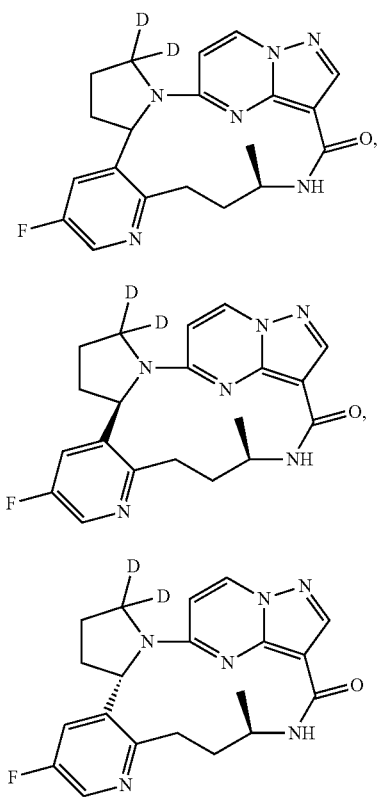
Use the following route for synthesis:
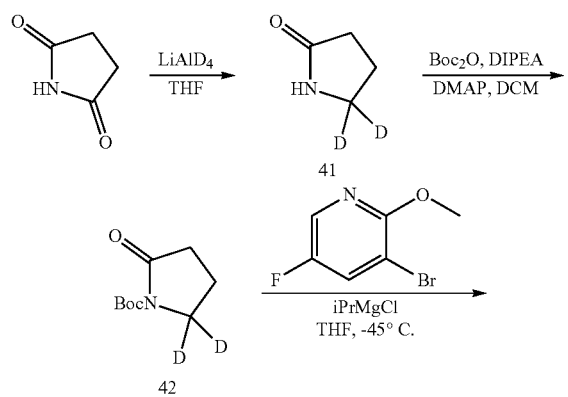
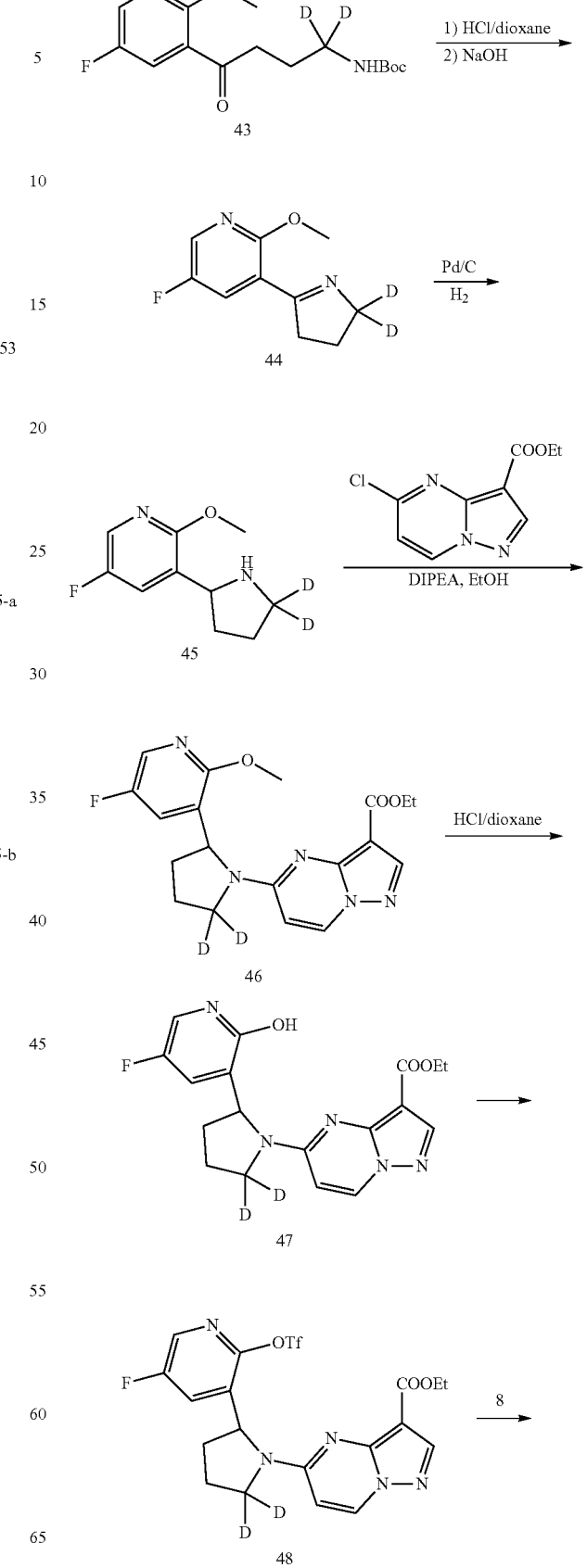

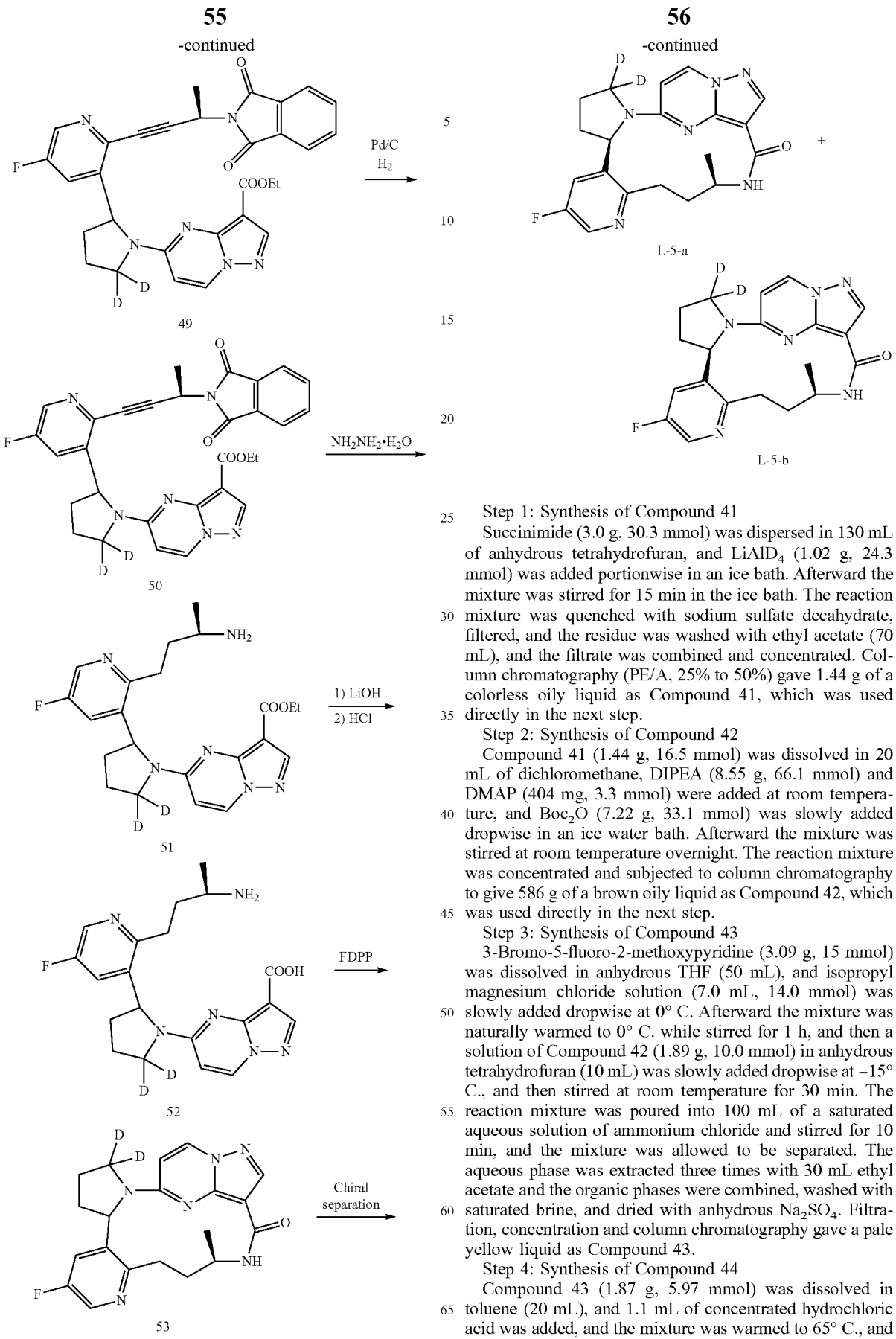

Step 1: Synthesis of Compound 41

Succinimide (3.0 g, 30.3 mmol) was dispersed in 130 mL of anhydrous tetrahydrofuran, and LiAlD$_4$ (1.02 g, 24.3 mmol) was added portionwise in an ice bath. Afterward the mixture was stirred for 15 min in the ice bath. The reaction mixture was quenched with sodium sulfate decahydrate, filtered, and the residue was washed with ethyl acetate (70 mL), and the filtrate was combined and concentrated. Column chromatography (PE/A, 25% to 50%) gave 1.44 g of a colorless oily liquid as Compound 41, which was used directly in the next step.

Step 2: Synthesis of Compound 42

Compound 41 (1.44 g, 16.5 mmol) was dissolved in 20 mL of dichloromethane, DIPEA (8.55 g, 66.1 mmol) and DMAP (404 mg, 3.3 mmol) were added at room temperature, and Boc$_2$O (7.22 g, 33.1 mmol) was slowly added dropwise in an ice water bath. Afterward the mixture was stirred at room temperature overnight. The reaction mixture was concentrated and subjected to column chromatography to give 586 g of a brown oily liquid as Compound 42, which was used directly in the next step.

Step 3: Synthesis of Compound 43

3-Bromo-5-fluoro-2-methoxypyridine (3.09 g, 15 mmol) was dissolved in anhydrous THF (50 mL), and isopropyl magnesium chloride solution (7.0 mL, 14.0 mmol) was slowly added dropwise at 0° C. Afterward the mixture was naturally warmed to 0° C. while stirred for 1 h, and then a solution of Compound 42 (1.89 g, 10.0 mmol) in anhydrous tetrahydrofuran (10 mL) was slowly added dropwise at −15° C., and then stirred at room temperature for 30 min. The reaction mixture was poured into 100 mL of a saturated aqueous solution of ammonium chloride and stirred for 10 min, and the mixture was allowed to be separated. The aqueous phase was extracted three times with 30 mL ethyl acetate and the organic phases were combined, washed with saturated brine, and dried with anhydrous Na$_2$SO$_4$. Filtration, concentration and column chromatography gave a pale yellow liquid as Compound 43.

Step 4: Synthesis of Compound 44

Compound 43 (1.87 g, 5.97 mmol) was dissolved in toluene (20 mL), and 1.1 mL of concentrated hydrochloric acid was added, and the mixture was warmed to 65° C., and the reaction was stirred overnight. Then the temperature was lowered to room temperature, and pH was adjusted to 14 with 2M sodium hydroxide, and then stirring was continued for 1 hour. The reaction was completed by TLC. The organic phase was separated, and the aqueous phase was extracted with ethyl acetate three times. The organic phases were combined, washed with saturated brine, concentrated, and then purified by column chromatography to give 624 mg of a yellow liquid as Compound 44.

Step 5: Synthesis of Compound 45

Compound 44 (624 mg, 3.21 mmol) was dissolved in anhydrous methanol (10 mL). Pd/C (50 mg) was added for hydrogenation at room temperature overnight. After filtration, the residue was washed with 20 mL of ethyl acetate, and the filtrate was concentrated to give 620 mg of a colorless oily liquid as Compound 45.

Step 6: Synthesis of Compound 46

Compound 45 (162 mg, 0.82 mmol) and ethyl 5-chloropyrazolo[1,5-a]pyrimidine-3-carboxylate (185.4 mg, 0.82 mmol) were dissolved in anhydrous ethanol (6 mL) and DIPEA (423.9 mg, 3.28 mmol) was added at room temperature, and heated to reflux for 30 min. The reaction solution was concentrated and subjected to column chromatography (PE/EA, 30% to 50%) to give 204 mg of a pale yellow solid powder as Compound 46.

Step 7: Synthesis of Compound 47

Compound 46 (200 mg, 0.52 mmol) was dissolved in 4M hydrogen chloride in dioxane (5 ml, 20 mmol), and then sealed and heated to 110° C. while stirred for 24 h. After the reaction was completed by TLC, the mixture was concentrated to remove the solvent, and used directly in the next step.

Step 8: Synthesis of Compound 48

Compound 47 (1.78 g, 4.79 mmol) and N-phenylbis(trifluoromethanesulfonyl)imide (1.88 g, 5.27 mmol) were dispersed in 25 mL of anhydrous DMF, and triethylamine (581.6 mg, 5.75 mmol) was added. The reaction was stirred at room temperature under nitrogen atmosphere. After the reaction was completed by TLC, the mixture was diluted with water, and extracted with ethyl acetate three times. The organic phases were combined, washed with saturated brine, and concentrated. Column chromatography (PE/EA: 50% to 66%) gave a yellow solid powder as Compound 48.

Step 9: Synthesis of Compound 49

Compound 48 (503.1 mg, 1.0 mmol) and Compound 8 (199 mg, 1.0 mmol) were dissolved in 25 mL of anhydrous tetrahydrofuran, and Pd(PPh$_3$)$_2$Cl$_2$ (35 mg, 0.05 mmol) and CuI (19 mg, 0.1 mmol) were added under nitrogen atmosphere. Triethylamine (202.4 mg, 2.0 mmol) was added in one portion at room temperature and stirred at room temperature overnight. After the reaction was completed by TLC, the mixture was concentrated to remove the solvent. Column chromatography gave a pale yellow solid powder as Compound 49.

Step 10: Synthesis of Compound 50

Compound 49 (287 mg, 0.52 mmol) was dissolved in a mixed solution of 5 ml of methanol and 5 ml of tetrahydrofuran, and a catalytic amount of Pd/C was added. The reaction was stirred at room temperature for 2-4 h under hydrogen atmosphere. After the reaction was completed by TLC, the catalyst was removed by filtration and the filtrate was concentrated to dryness and directly used in the next step.

Step 11: Synthesis of Compound 51

Compound 50 (287 mg, 0.52 mmol) was dissolved in 10 ml of methanol, and hydrazine hydrate (130 mg, 2.6 mmol) was added, and the mixture was heated to reflux for 1-2 h. After the reaction was completed by TLC, the mixture was concentrated to remove the solvent and purified by column chromatography to obtain a pale yellow solid as Compound 51.

Step 12: Synthesis of Compound 52

Compound 51 (224 mg, 0.52 mmol) was dissolved in 3 ml of methanol and 2 ml of water, and lithium hydroxide (109.2 mg, 2.6 mmol) was added. The temperature was raised to 50° C., and the reaction was stirred for 4-6 h. After the reaction was completed by TLC, the mixture was cooled to room temperature. Diluted hydrochloric acid was added to adjust the pH to acidity. The mixture was concentrated to remove the solvent, and directly used in the next step.

Step 13: Synthesis of Compound 53

The product obtained in the above step was dissolved in 20 ml of anhydrous DMF, and FDPP (240 mg, 0.62 mmol) and DIPEA (336 mg, 2.6 mmol) were added at room temperature, and the reaction was stirred overnight under nitrogen atmosphere. After the reaction was completed by TLC, the mixture was diluted with water, and extracted 3-4 times with ethyl acetate. The organic phase was combined, washed with saturated brine, and concentrated. Column chromatography gave an off white solid as Compound 53.

Step 14: Preparation of Compounds L-5-a and L-5-b

The racemic compound 53 was separated using a chiral preparative chromatographic column to give Compounds L-5-a and L-5-b.

Example 6: Preparation of (15R)-9-fluoro-15-methyl-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-4,4,13,13,14,14-d$_6$ (compound 57); (6R,15R)-9-fluoro-15-methyl-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-4,4,13,13,14,14-d$_6$ (Compound L-6-a); and (6S,15R)-9-fluoro-15-methyl-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-4,4,13,13,14,14-d$_6$ (Compound L-6-b)

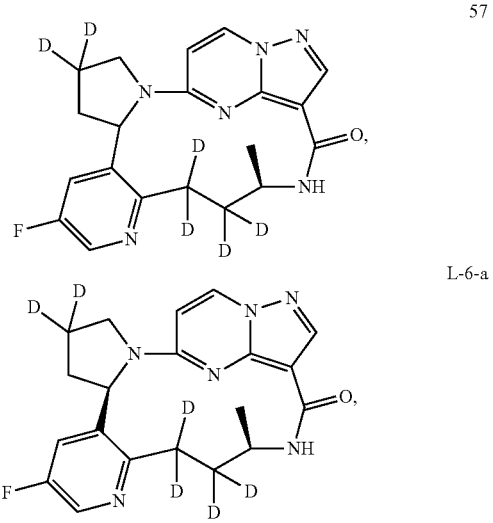

59
-continued

L-6-b

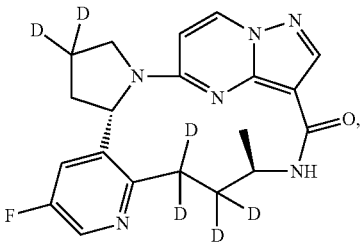

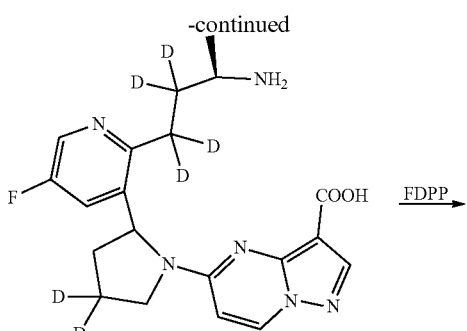

56

Use the following route for synthesis:

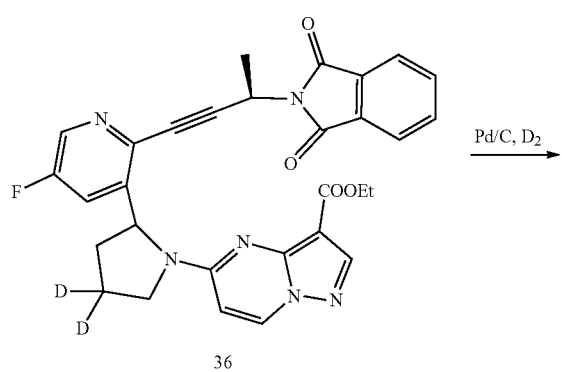

36

Pd/C, D₂

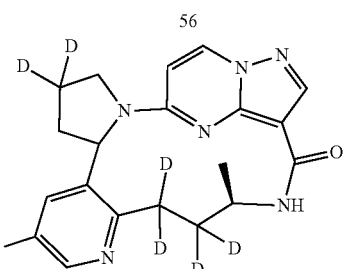

57

Chiral separation

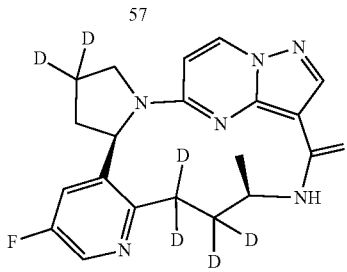

L-6-a

+

NH₂NH₂·H₂O

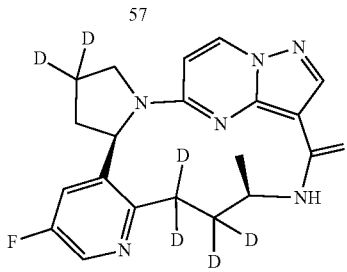

L-6-b

54

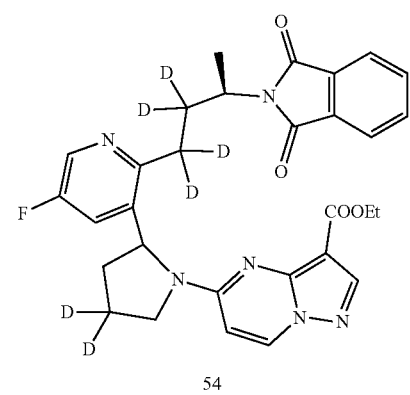

55

1) LiOH
2) HCl

Step 1: Synthesis of Compound 54

Compound 36 (287 mg, 0.52 mmol) was dissolved in 10 ml of deuterated methanol, and a catalytic amount of Pd/C was added. The reaction was stirred at room temperature for 2-4 h under deuterium atmosphere. After the reaction was completed by TLC, the catalyst was removed by filtration and the filtrate was concentrated to dryness and directly used in the next step.

Step 2: Synthesis of Compound 55

Compound 54 (289 mg, 0.52 mmol) was dissolved in 10 ml of methanol, and hydrazine hydrate (130 mg, 2.6 mmol) was added, and the mixture was heated to reflux for 1-2 h. After the reaction was completed by TLC, the mixture was concentrated to remove the solvent and purified by column chromatography to obtain a pale yellow solid as Compound 55.

Step 3: Synthesis of Compound 56

Compound 55 (226 mg, 0.52 mmol) was dissolved in 3 ml of methanol and 2 ml of water, and lithium hydroxide (109.2 mg, 2.6 mmol) was added. The temperature was raised to 50° C., and the reaction was stirred for 4-6 h. After the reaction was completed by TLC, the mixture was cooled to room temperature. Diluted hydrochloric acid was added to adjust the pH to acidity. The mixture was concentrated to remove the solvent, and directly used in the next step.

Step 4: Synthesis of Compound 57

The product obtained in the above step was dissolved in 20 ml of anhydrous DMF, and FDPP (240 mg, 0.62 mmol) and DIPEA (336 mg, 2.6 mmol) were added at room temperature, and the reaction was stirred overnight under nitrogen atmosphere. After the reaction was completed by TLC, the mixture was diluted with water, and extracted 3-4 times with ethyl acetate. The organic phases were combined, washed with saturated brine, and concentrated. Column chromatography gave an off white solid as Compound 57.

Step 5: Preparation of Compounds L-6-a and L-6-b

The racemic compound 57 was separated using a chiral preparative chromatographic column to give Compounds L-6-a and L-6-b.

Example 7: Preparation of (15R)-9-fluoro-15-methyl-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-3,3,13,13,14,14-d$_6$ (Compound 61); (6R,15R)-9-fluoro-15-methyl-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-3,3,13,13,14,14-d$_6$ (Compound L-7-a); and (6S,15R)-9-fluoro-15-methyl-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-3,3,13,13,14,14-d$_6$ (Compound L-7-b)

Use the following route for synthesis:

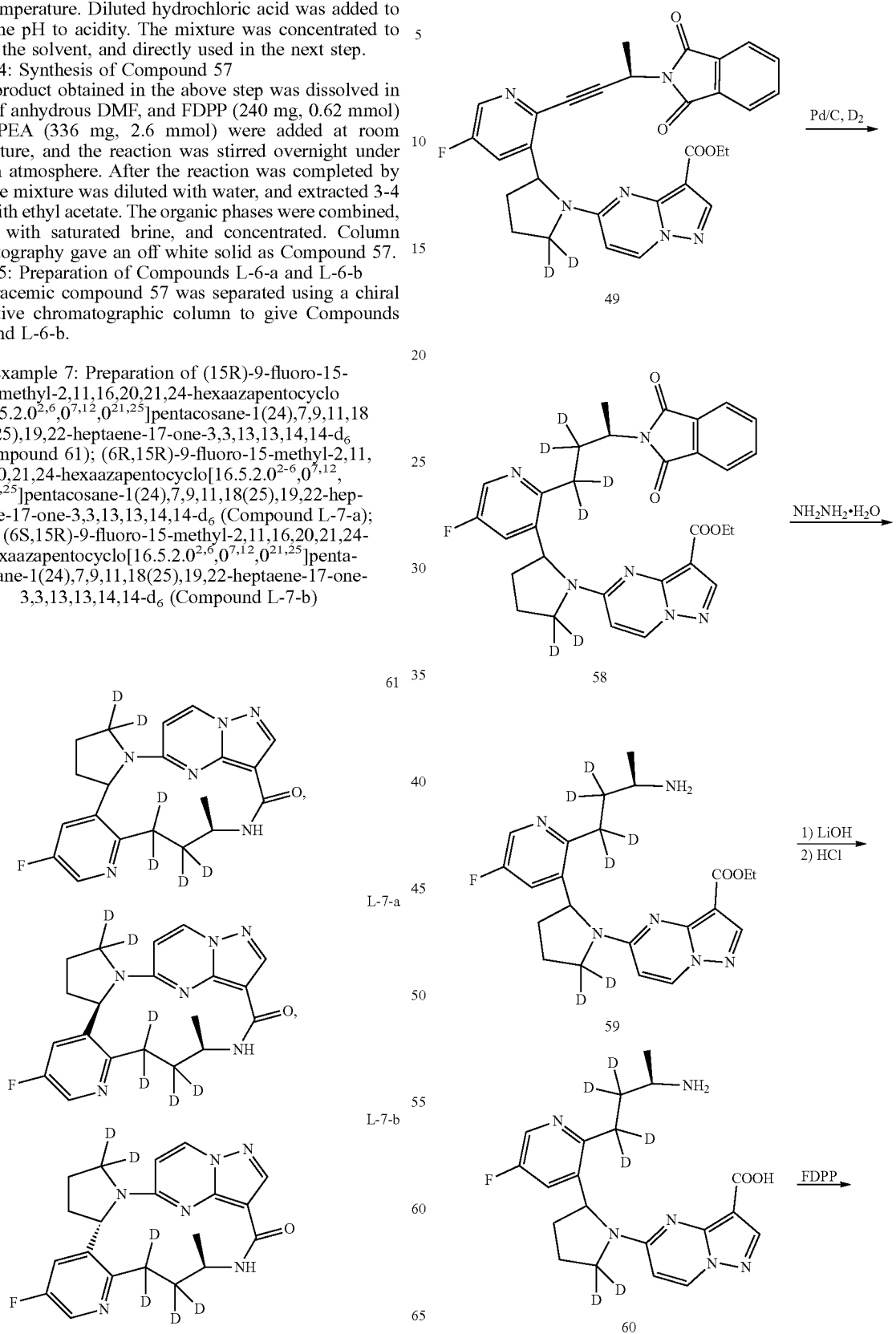

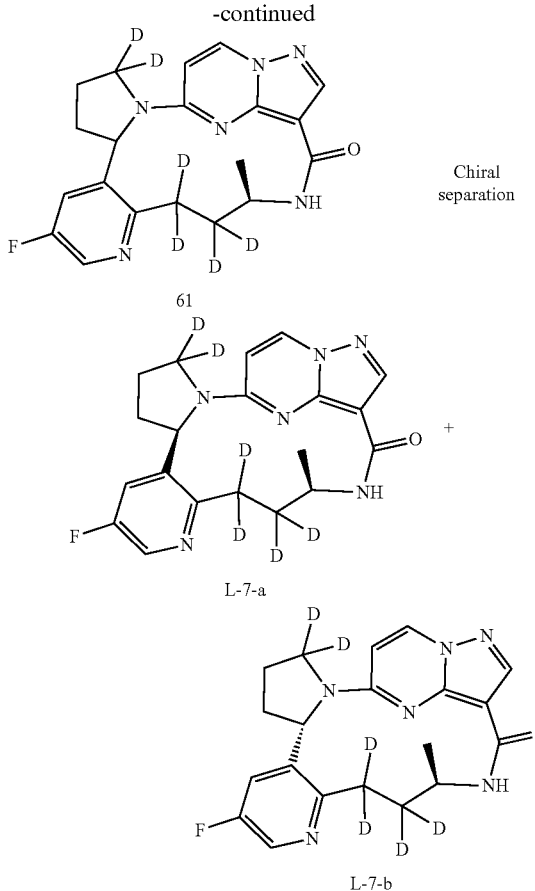

Step 1: Synthesis of Compound 58

Compound 49 (287 mg, 0.52 mmol) was dissolved in 10 ml of deuterated methanol, and a catalytic amount of Pd/C was added. The reaction was stirred at room temperature for 2-4 h under deuterium atmosphere. After the reaction was completed by TLC, the catalyst was removed by filtration and the filtrate was concentrated to dryness and directly used in the next step.

Step 2: Synthesis of Compound 59

Compound 58 (289 mg, 0.52 mmol) was dissolved in 10 ml of methanol, and hydrazine hydrate (130 mg, 2.6 mmol) was added, and the mixture was heated to reflux for 1-2 h. After the reaction was completed by TLC, the mixture was concentrated to remove the solvent and purified by column chromatography to obtain a pale yellow solid as Compound 59.

Step 3: Synthesis of Compound 60

Compound 59 (226 mg, 0.52 mmol) was dissolved in 3 ml of methanol and 2 ml of water, and lithium hydroxide (109.2 mg, 2.6 mmol) was added. The temperature was raised to 50° C., and the reaction was stirred for 4-6 h. After the reaction was completed by TLC, the mixture was cooled to room temperature. Diluted hydrochloric acid was added to adjust the pH to acidity. The mixture was concentrated to remove the solvent, and directly used in the next step.

Step 4: Synthesis of Compound 61

The product obtained in the above step was dissolved in 20 ml of anhydrous DMF, and FDPP (240 mg, 0.62 mmol) and DIPEA (336 mg, 2.6 mmol) were added at room temperature, and the reaction was stirred overnight under nitrogen atmosphere. After the reaction was completed by TLC, the mixture was diluted with water, and extracted 3-4 times with ethyl acetate. The organic phases were combined, washed with saturated brine, and concentrated. Column chromatography gave an off white solid as Compound 61.

Step 5: Preparation of Compounds L-7-a and L-7-b

The racemic compound 61 was separated using a chiral preparative chromatographic column to give Compounds L-7-a and L-7-b.

Example 8: Preparation of 9-fluoro-15-(methyl-d$_3$)-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-15-d (Compound 70); (6R, 15R)-9-fluoro-15-(methyl-d$_3$)-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-15-d (Compound L-8-a); (6S,15R)-9-fluoro-15-(methyl-d$_3$)-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-15-d (Compound L-8-b); (6R,15S)-9-fluoro-15-(methyl-d$_3$)-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-15-d (Compound L-8-c); and (6S,15S)-9-fluoro-15-(methyl-d$_3$)-2,11,16,20,21,24-hexaazapentocyclo[16.5.2.0$^{2,6}$,0$^{7,12}$,0$^{21,25}$]pentacosane-1(24),7,9,11,18(25),19,22-heptaene-17-one-15-d (Compound L-8-d)

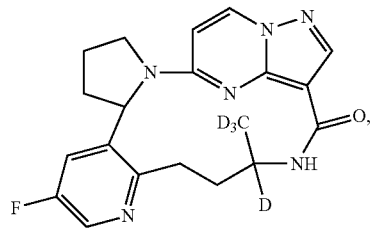

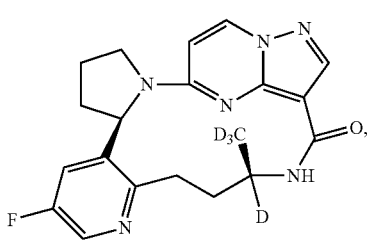

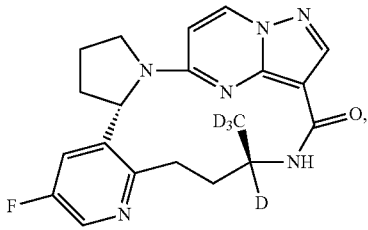

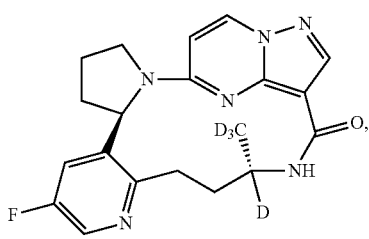
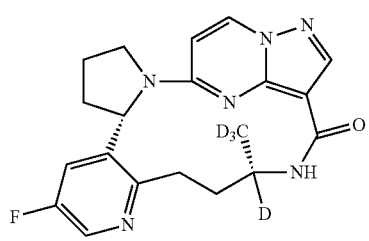
Use the following route for synthesis:
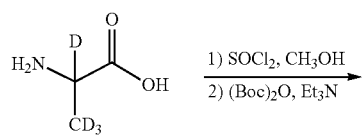
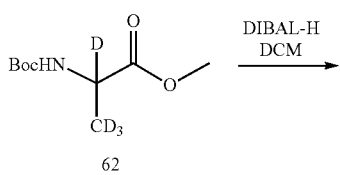
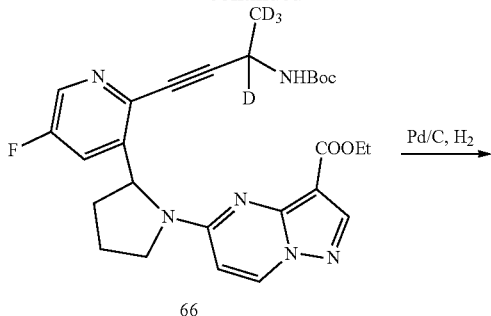
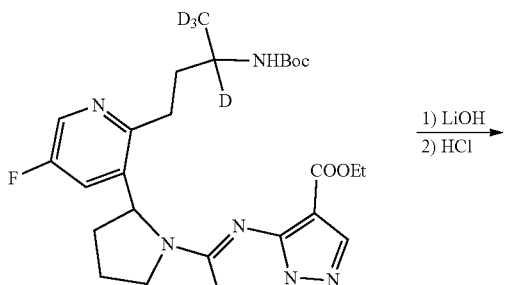
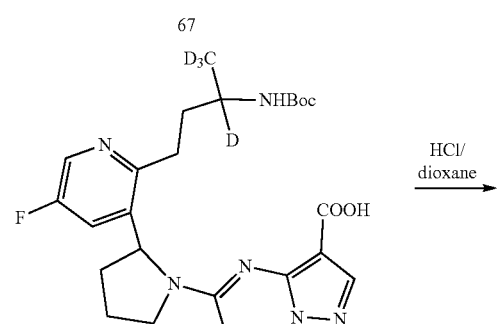
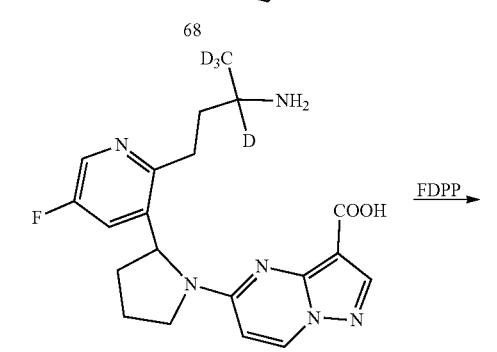

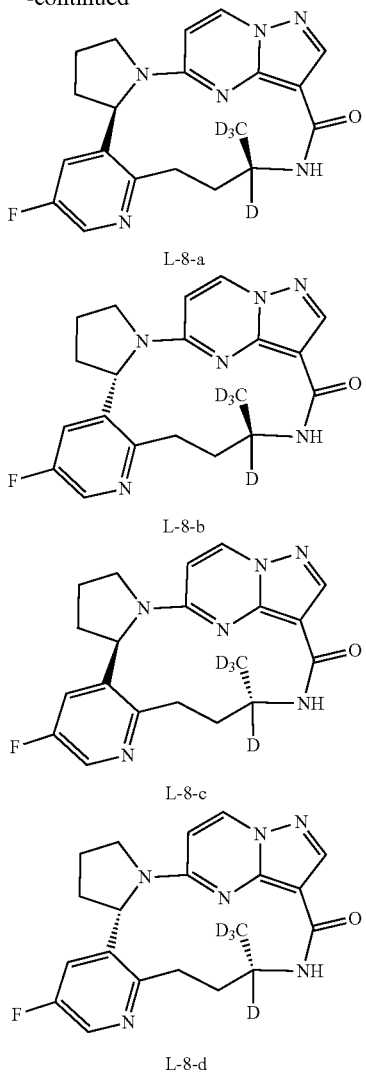

L-8-a

L-8-b

L-8-c

L-8-d

Step 1: Synthesis of Compound 62

Alanine-d$_4$ (1.0 g, 10.74 mmol) was dissolved in 20 mL of anhydrous methanol, and thionyl chloride (6.4 g, 53.7 mmol) was slowly added dropwise at 0° C. Afterward, the reaction was refluxed for 2-4 h. After the reaction was completed by TLC, the mixture was concentrated to remove the solvent. Toluene was added 2-3 times, dichloromethane (20 ml) was added to be dissolved, triethylamine (2.17 g, 21.48 mmol) was added, and (Boc)$_2$O (2.81 g, 12.89 mmol) was slowly added dropwise at 0° C. under nitrogen atmosphere, and then the mixture was stirred at room temperature for 5 h. After the reaction was completed by TLC, the mixture was diluted with dichloromethane, washed successively with water and saturated brine, and then concentrated. Column chromatography gave 1.82 g of a colorless oily liquid. Yield: 82%.

Step 2: Synthesis of Compound 63

Compound 62 (1.82 g, 8.8 mmol) was dissolved in 20 mL of anhydrous dichloromethane, and then cooled to −78° C. under nitrogen atmosphere, and DIBAL-H (diisobutylaluminum hydride, 8.8 ml, 8.8 mmol) was slowly added dropwise. The reaction was stirred overnight at a low temperature. After the reaction was completed by TLC, the mixture was diluted with water, and the aqueous phase was extracted three times with ethyl acetate. The organic phase was combined, washed with saturated brine, and concentrated. Column chromatography gave 1.01 g of a colorless liquid. Yield: 65%. LC-MS (APCI): m/z=178.2 (M+1)$^+$.

Step 3: Synthesis of Compound 65

Compound 63 (1.01 g, 5.7 mmol) and Compound 64 (1.1 g, 5.7 mmol) were dissolved in 25 mL of anhydrous methanol, and potassium carbonate (2.36 g, 17.1 mol) was added and the mixture was stirred at room temperature overnight. After the reaction was completed by TLC, the mixture was concentrated to remove the solvent. Column chromatography gave 759 mg of a pale yellow solid powder. Yield: 77%. LC-MS (APCI): m/z=174.3 (M+1)$^+$.

Step 4: Synthesis of Compound 66

Compound 6 (287 mg, 0.52 mmol) and Compound 65 (135 mg, 0.78 mmol) were dissolved in 10 ml of anhydrous tetrahydrofuran, and di(triphenylphosphine)palladium dichloride (36.5 mg, 0.052 mmol) and Copper iodide (19 mg, 0.1 mmol) were added under nitrogen atmosphere. Then potassium carbonate (107.8 mg, 0.78 mmol) was added, and the mixture was heated to 100° C. while stirred overnight. After the reaction was completed by TLC, the catalyst was removed by filtration, and the filtrate was concentrated to dryness. Column chromatography gave 194 mg of a pale yellow powder. Yield: 71%. LC-MS (APCI): m/z=527.3 (M+1)$^+$.

Step 5: Synthesis of Compound 67

Compound 66 (194 mg, 0.37 mmol) was dissolved in 10 ml of methanol, and a catalytic amount of Pd/C was added. The reaction was carried out at room temperature for 2-4 h under hydrogen atmosphere. After the reaction was completed by TLC, the catalyst was removed by filtration and the filtrate was concentrated to dryness and directly used in the next step.

Step 6: Synthesis of Compound 68

Compound 67 (196 mg, 0.37 mmol) was dissolved in 3 ml of methanol and 2 ml of water, and lithium hydroxide (109.2 mg, 2.6 mmol) was added. The temperature was raised to 50° C., and the reaction was stirred for 4-6 h. After the reaction was completed by TLC, the mixture was cooled to room temperature. Diluted hydrochloric acid was added to adjust the pH to acidity. The mixture was extracted 3-4 times with ethyl acetate. The organic phases were combined, and concentrated. Column chromatography gave 175 mg of a pale yellow solid. Yield: 94%. LC-MS (APCI): m/z=503.1 (M+1)$^+$.

Step 7: Synthesis of Compound 69

Compound 68 (175 mg, 0.35 mmol) was added into 4M hydrogen chloride in dioxane (5 ml, 20 mmol), and the mixture was stirred at room temperature for 1-2 hrs. After the reaction was completed by TLC, the mixture was concentrated to remove the solvent, and used directly in the next step.

Step 7: Synthesis of Compound 70

The product obtained in the above step was dissolved in 10 ml of anhydrous DMF, and FDPP (240 mg, 0.62 mmol) and DIPEA (336 mg, 2.6 mmol) were added at room temperature, and the reaction was stirred overnight under nitrogen atmosphere. After the reaction was completed by TLC, the mixture was diluted with water, and extracted 3-4 times with ethyl acetate. The organic phases were combined, washed with saturated brine, and concentrated. Column chromatography gave 58.3 mg of an off white solid. Yield: 43.3%. LC-MS (APCI): m/z=385.3 (M+1)+. $^1$H NMR (400 MHz, DMSO) δ 8.85 (s, 1H), 8.42 (s, 1H), 8.31 (s, 1H), 8.06 (d, J=2.3 Hz, 1H), 7.51 (s, 1H), 6.74 (d, J=2.3 Hz, 1H), 4.38

(t, 1H), 3.61 (dd, J=17.0, 9.3 Hz, 2H), 3.15 (m, 2H), 2.06 (m, 2H), 2.01-1.65 (m, 2H), 1.22 (d, J=4.5 Hz, 2H).

Step 7: Preparation of Compounds L-8-a, L-8-b, L-8-c and L-8-d

The racemic compound 70 was separated using a chiral preparative chromatographic column to give Compounds L-8-a, L-8-b, L-8-c, and L-8-d.

Biological Activity Test (1) Kinase Inhibition

Compound Preparation: The test compounds were dissolved in DMSO to make a 20 mM stock solution. The compounds were diluted to 0.1 mM (100 times the final concentration of the dilution) in DMSO before use, and performed 3× gradient dilutions with 11 concentrations. They were diluted to 4 times the final concentration of the dilution with the buffer when administration.

Kinase assay: After the buffer was prepared, the enzyme was mixed with different concentrations of the compound prepared by pre-diluting, and allowed to stand at room temperature for 30 minutes, with each concentration in duplicate. The corresponding substrate and ATP were added and reacted at room temperature for 60 minutes (wherein negative and positive controls were set). After the reaction was completed, the antibody was added for detection. After incubation at room temperature for 60 minutes, Evnvision detection was performed, and data were collected. The enzyme activities in the presence of varying concentration of the compounds of the present invention were determined by Evnvision microplate reader, and the inhibitory activities of the compounds at different concentrations on the enzyme activity were calculated. Then, the inhibitory activities of the compounds at different concentrations on the enzyme activity were fitted to the four-parameter equation according to the Graphpad 5.0 software, and the $IC_{50}$ values were calculated.

The inhibitory activities of the compounds of the present invention against TRK A, TRK B, and TRK C kinases were tested as described above. The results of kinase inhibition in the representative example compounds are shown in Table 1.

TABLE 1

| Example compound | TRK A $IC_{50}$(nM) | TRK B $IC_{50}$(nM) | TRK C $IC_{50}$(nM) |
|---|---|---|---|
| Compound Φ | 8.27 | 4.19 | 3.10 |
| Compound Φ-a | 0.29 | 0.08 | 0.11 |
| Compound L-2-a | 0.17 | 0.07 | 0.07 |

As shown in Table 1, the compounds of the present invention have significant protein kinase inhibitory activities and generally have $IC_{50}$ values below 1 nM. In particular, the compounds of the present invention exhibited strong inhibitory activities against TRKA/B/C as compared with the Compound Φ and Compound Φ-a, both of which were not deuterated.

(2) Cytotoxicity Test

The inhibitory effect of the example compounds on the activity of KM12 (TPM3-TRKA) cells was examined.

Materials and reagents: RPMI-1640 medium (GIBCO, Cat. No. A10491-01), fetal bovine serum (GIBCO, Cat. No. 10099141), antibiotic (Penicillin-Streptomycin), IL-3 (PeproTech), puromycin; living cell assay kit CellTiter-Glo4 (Promega, Cat. No. G7572), 96-well black-wall clear flat bottom cell culture plate (Corning, Cat. No. 3340).

Experimental methods: 1. Preparation of cell plates—KM12 cells were separately seeded in 96-well plates, and 8 ng/ml IL-3 was added to KM12 cells, and the cell plates were incubated in a carbon dioxide incubator overnight. 2. The test compound was dissolved in DMSO and subjected to a 3.16-fold gradient dilution with 9 compound concentrations in triplicate. 3. Compound Treatment of Cells—The compounds were transferred to cell plates at a starting concentration of 10 μM. The cell plates were incubated in a carbon dioxide incubator for 3 days. 4. Detection—The CellTiter-Glo reagent was added to the cell plate and incubated for 30 minutes at room temperature to stabilize the luminescence signal. Readings were performed using a PerkinElmer Envision multi-label analyzer. The results of inhibition of cell proliferation by representative example compounds are shown in Table 2.

TABLE 2

| Example Compound | KM12 $IC_{50}$(nM) |
|---|---|
| Compound Φ-a | 2.56 |
| Compound L-2-a | 2.51 |

As shown in Table 2, the compounds of the present invention both exhibited better effects for inhibiting the proliferation of KM12 cells.

(3) Metabolic Stability Evaluation

Microsome tests: human liver microsomes: 0.5 mg/mL, Xenotech; rat liver microsomes: 0.5 mg/mL, Xenotech; coenzyme (NADPH/NADH): 1 mM, Sigma Life Science; magnesium chloride: 5 mM, 100 mM phosphate buffer agent (pH 7.4).

Preparation of the stock solution: A certain amount of the powder of the example compounds was accurately weighed and dissolved to 5 mM with DMSO.

Preparation of phosphate buffer (100 mM, pH 7.4): 150 mL of pre-prepared 0.5 M potassium dihydrogen phosphate solution was mixed with 700 mL of pre-prepared 0.5 M dipotassium hydrogen phosphate solution, and the pH of the mixture was adjusted with 0.5 M dipotassium hydrogen phosphate solution to 7.4. It was diluted 5 times with ultrapure water before use, and magnesium chloride was added to obtain a phosphate buffer (100 mM) containing 100 mM potassium phosphate, 3.3 mM magnesium chloride, and a pH of 7.4.

A solution of NADPH regeneration system (containing 6.5 mM NADP, 16.5 mM G-6-P, 3 U/mL G-6-P D, 3.3 mM magnesium chloride) was prepared and placed on wet ice before use.

Preparation of stop solution: acetonitrile solution containing 50 ng/mL propranolol hydrochloride and 200 ng/mL tolbutamide (internal standard). 25057.5 μL of phosphate buffer (pH 7.4) was taken into a 50 mL centrifuge tube, 812.5 μL of human liver microsomes was added respectively, and mixed uniformly to obtain a liver microsome dilution with a protein concentration of 0.625 mg/mL. 25057.5 μL of phosphate buffer (pH 7.4) was taken into a 50 mL centrifuge tube, and 812.5 μL of SD rat liver microsomes was added respectively, and mixed uniformly to obtain a liver microsome dilution with a protein concentration of 0.625 mg/mL.

Incubation of the sample: The stock solutions of the corresponding compounds were diluted to 0.25 mM as working solutions with an aqueous solution containing 70% acetonitrile before use. 398 μL of human liver microsome or rat liver microsome dilutions were added to 96-well incubation plates (N=2), and 2 μL of 0.25 mM working solutions were added and mixed uniformly, respectively.

Determination of metabolic stability: 300 μL of pre-cooled stop solution was added to each well of a 96-well deep well plate, which was placed on ice as a stop plate. The 96-well incubation plate and the NADPH regeneration system were placed in a 37° C. water bath, shaken at 100 rpm, and pre-incubated for 5 min. 80 μL of the incubation solution was removed from each well of the incubation plate, added to the stop plate, and mixed uniformly, and 20 μL of the NADPH regeneration system solution was supplemented as a sample at 0 min. Then, 80 μL of the NADPH regeneration system solution was added to each well of the incubation plate to start the reaction and the timing was started. The corresponding compounds had a reaction concentration of 1 μM and a protein concentration of 0.5 mg/mL. 100 μL of the reaction solution was removed at 10, 30, and 90 min of the reaction, respectively, and added to the stop plate, and the reaction was terminated by vortexing for 3 min. The stop plate was centrifuged at 5000×g for 10 min at 4° C. 100 μL of the supernatant was removed into a 96-well plate to which 100 μL of distilled water was previously added, mixed uniformly, and sample analysis was performed by LC-MS/MS.

Data analysis: The peak areas of the corresponding compounds and the internal standard were detected by LC-MS/MS system, and the ratios of the peak areas of the compounds to the internal standard were calculated. The slope was measured by the natural logarithm of the percentages of the remaining amounts of the compounds versus time, and $t_{1/2}$ and $CL_{int}$ were calculated according to the following formula, where V/M is equal to 1/protein concentration.

$$t_{1/2} = -\frac{0.693}{\text{slope}}, \quad CL_{int} = \frac{0.693}{t_{1/2}} \cdot \frac{V}{M}, \quad t_{1/2}(\min); CL_{int}(\mu L/\min/mg).$$

The metabolic stability in human and rat liver microsomes was evaluated by simultaneously testing and comparing the compounds of the present invention and the compound without deuteration. The non-deuterated compound LOXO-195 was used as a control. In the human and rat liver microsome tests, the compounds of the invention could significantly improve metabolic stability by comparison with the non-deuterated compound LOXO-195. The results of human and rat liver microsome tests of representative example compounds are shown in Table 3 below:

TABLE 3

| Compound NO. | human liver microsome test | | rat liver microsome test | |
| --- | --- | --- | --- | --- |
| | $t_{1/2}$(min) | $CL_{int}$ (μL/min/mg) | $t_{1/2}$(min) | $CL_{int}$ (μL/min/mg) |
| Compound Φ | 14.7 | 94.3 | 23.3 | 59.5 |
| Compound Φ-a | 12.9 | 107.7 | 16.7 | 83.2 |
| Compound Φ-b | 17.7 | 78.4 | 17.5 | 79.2 |
| Compound 13 | 36.0 | 38.5 | 59.4 | 23.3 |
| Compound L-1-a | 24.5 | 56.5 | 31.3 | 44.2 |
| Compound L-1-b | 27.8 | 49.8 | 18.5 | 75.1 |

TABLE 3-continued

| Compound NO. | human liver microsome test | | rat liver microsome test | |
| --- | --- | --- | --- | --- |
| | $t_{1/2}$(min) | $CL_{int}$ (μL/min/mg) | $t_{1/2}$(min) | $CL_{int}$ (μL/min/mg) |
| Compound L-2-a | 17.4 | 79.6 | 30.4 | 45.6 |
| Compound L-2-b | 25.1 | 55.2 | 23.9 | 57.9 |
| Compound 70 | 17.6 | 78.7 | 39.1 | 35.5 |

(4) Rat Pharmacokinetic Experiment 6 male Sprague-Dawley rats, 7-8 weeks old, weighing approximately 210 g, were divided into 2 groups of 3 animals, and the pharmacokinetic differences were compared by intravenous or oral single dose of the compounds (10 mg/kg orally).

Rats were fed a standard diet and given water. Fasting began 16 hours before the experiment. The drugs were dissolved with PEG400 and dimethyl sulfoxide. Blood was collected from the fossa orbitalis at time points of 0.083 hours, 0.25 hours, 0.5 hours, 1 hour, 2 hours, 4 hours, 6 hours, 8 hours, 12 hours, and 24 hours after administration.

Rats were briefly anesthetized after inhalation of ether, and 300 μL of blood samples were collected from the fossa orbitalis into test tubes. There was 30 μL of 1% heparinate solution in the test tubes. The tubes were dried overnight at 60° C. before use. After the blood sample collection was completed at the last time point, the rats were anesthetized with ether and sacrificed.

Immediately after the blood sample was collected, the tubes were gently inverted at least 5 times to ensure adequate mixing and then placed on ice. Blood samples were centrifuged at 5000 rpm for 5 minutes at 4° C. to separate plasma from red blood cells. 100 μL of plasma was pipetted into a clean plastic centrifuge tube, indicating the names and time points of the compounds. Plasma was stored at −80° C. prior to analysis. The concentrations of the compounds of the invention in plasma were determined by LC-MS/MS. Pharmacokinetic parameters were calculated based on the plasma concentration of each animal at different time points.

The experiment has shown that the compounds of the invention have better pharmacokinetic properties in animals and therefore have better pharmacodynamics and therapeutic efficacy.

The above is a further detailed description of the present invention in connection with the specific preferred embodiments, and the specific embodiments of the present invention are not limited to the description. It will be apparent to those of ordinary skill in the art to which the present invention belongs that without departing from the spirit and scope of the invention, several simple deductions or replacements can be made, which should be regarded as falling within the protection scope of the present invention.

What is claimed is:

1. A compound of formula (Aa),

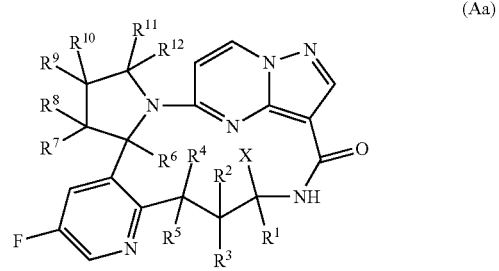

(Aa)

or a pharmaceutically acceptable salt, a hydrate or a solvate, a stereoisomer or an isotopic variant thereof, wherein, $R^1, R^2, R^3, R^4, R^5, R^6, R^7, R^8, R^9, R^{10}, R^{11}$ and $R^{12}$ are each independently selected from hydrogen or deuterium;

X is selected from $CH_3$, $CD_3$, $CHD_2$ or $CH_2D$;

wherein the content of deuterium isotope in each deuterated position is at least 5%, with the proviso that if X is $CH_3$, then at least one of $R^1, R^2, R^3, R^4, R^5, R^6, R^7, R^8, R^9, R^{10}, R^{11}$ and $R^{12}$ is deuterium.

2. A compound according to claim 1 which is a compound of formula (Aa-1),

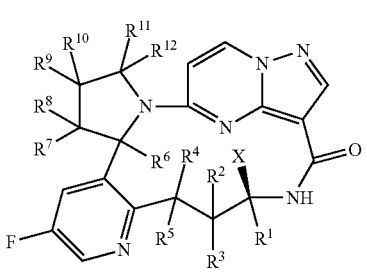

(Aa-1)

or a pharmaceutically acceptable salt, a hydrate or a solvate, a stereoisomer or an isotopic variant thereof, wherein $R^1, R^2, R^3, R^4, R^5, R^6, R^7, R^8, R^9, R^{10}, R^{11}, R^{12}$ and X are as defined in claim 1.

3. A compound according to claim 2 which is a compound of formula (Ia) or formula (IIa),

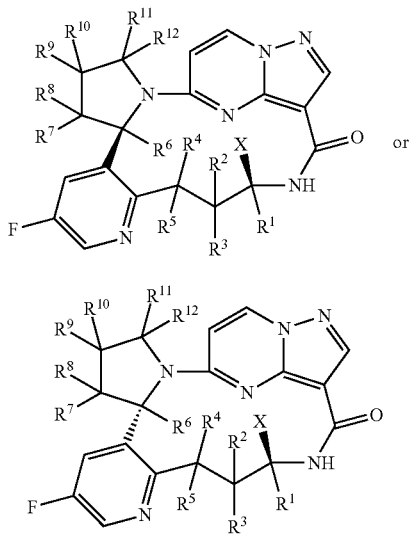

(Ia)

or (IIa)

or a pharmaceutically acceptable salt, a hydrate or a solvate, a stereoisomer or an isotopic variant thereof, wherein $R^1, R^2, R^3, R^4, R^5, R^6, R^7, R^8, R^9, R^{10}, R^{11}, R^{12}$ and X are as defined in claim 2.

4. The compound according to claim 1, wherein $R^{11}$ and $R^{12}$ are each independently selected from hydrogen.

5. The compound according to claim 1, wherein $R^9$ and $R^{10}$ are each independently selected from hydrogen.

6. The compound according to claim 1, wherein $R^1$ is selected from hydrogen.

7. The compound according to claim 1, wherein X is selected from $CH_3$.

8. The compound according to claim 1, wherein $R^2, R^3, R^4$ and $R^5$ are each independently selected from hydrogen.

9. The compound according to claim 1, wherein $R^6, R^7$ and $R^8$ are each independently selected from deuterium.

10. The compound according to claim 1, wherein the compound is selected from the group consisting of

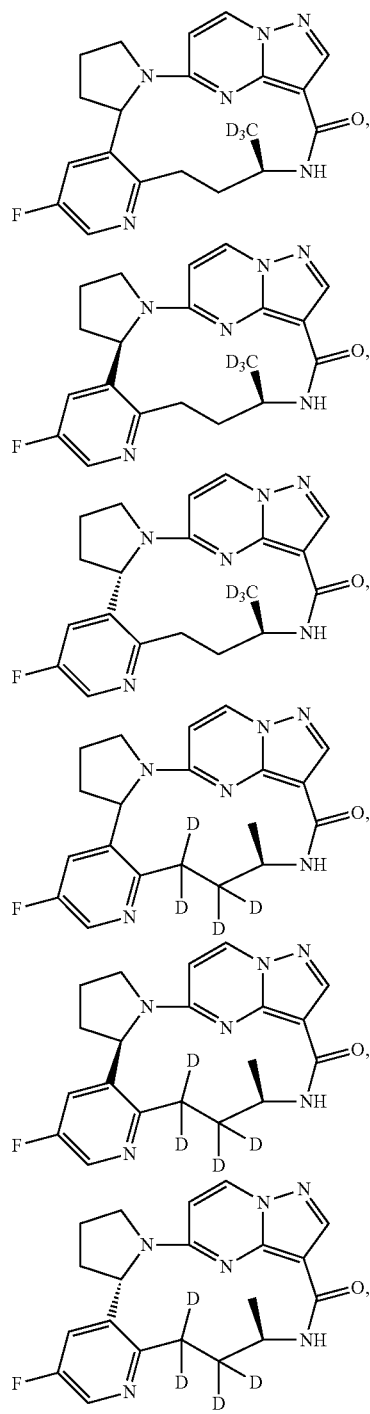

75
-continued
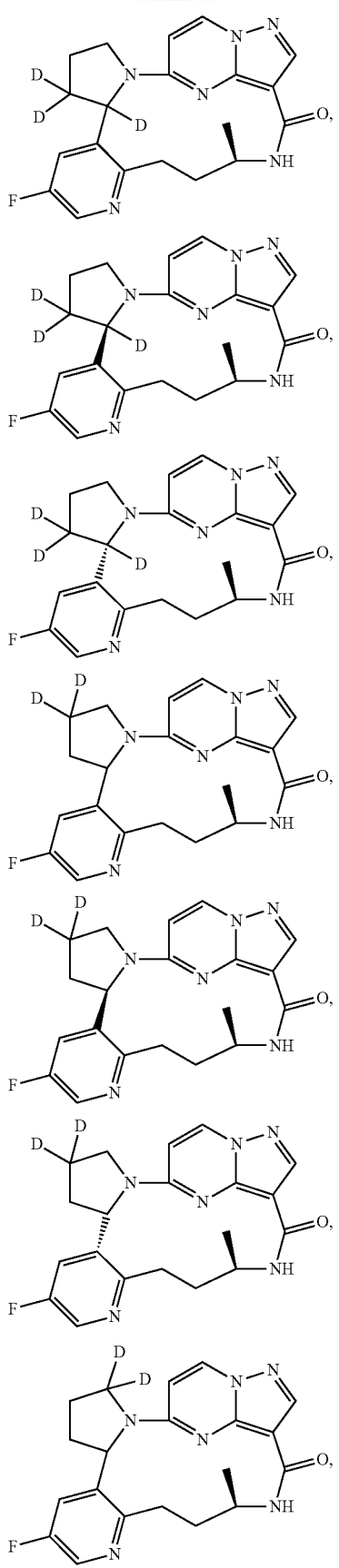
76
-continued
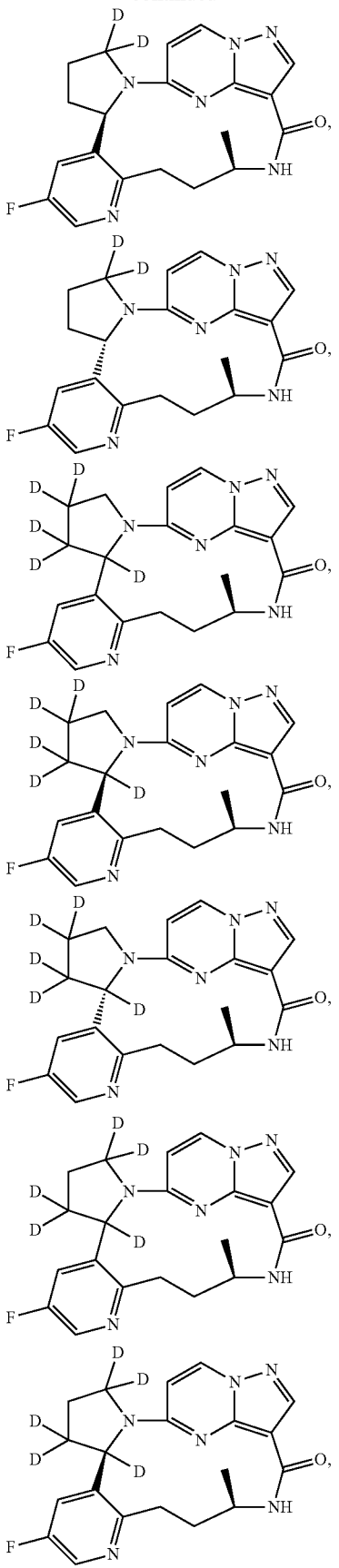

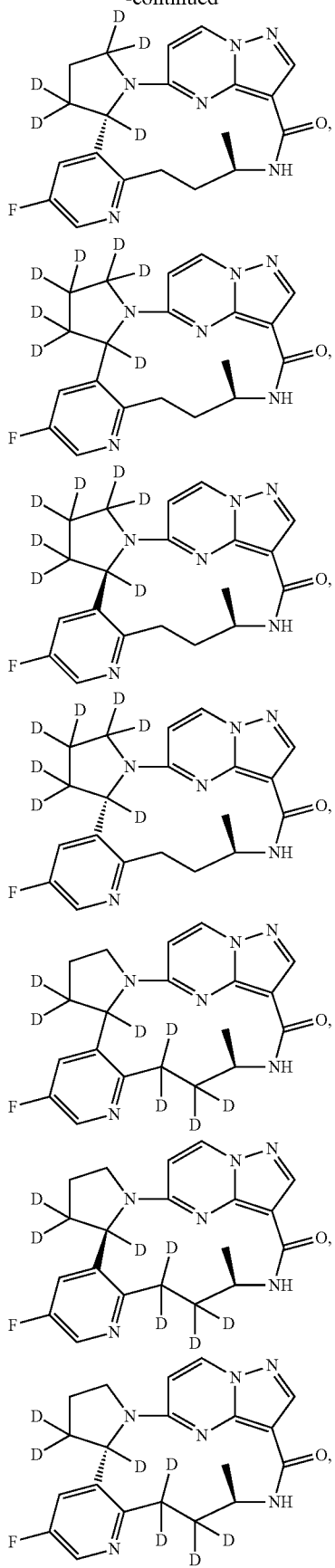
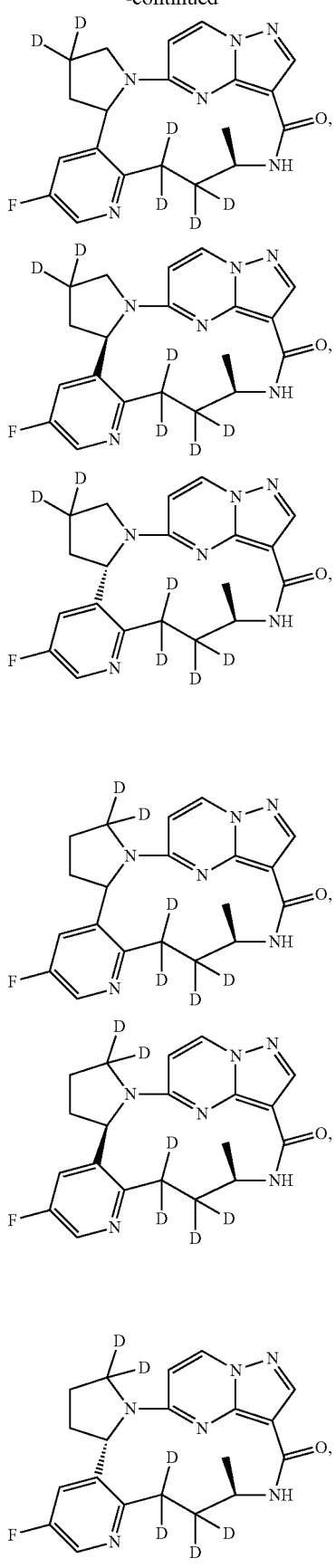

-continued
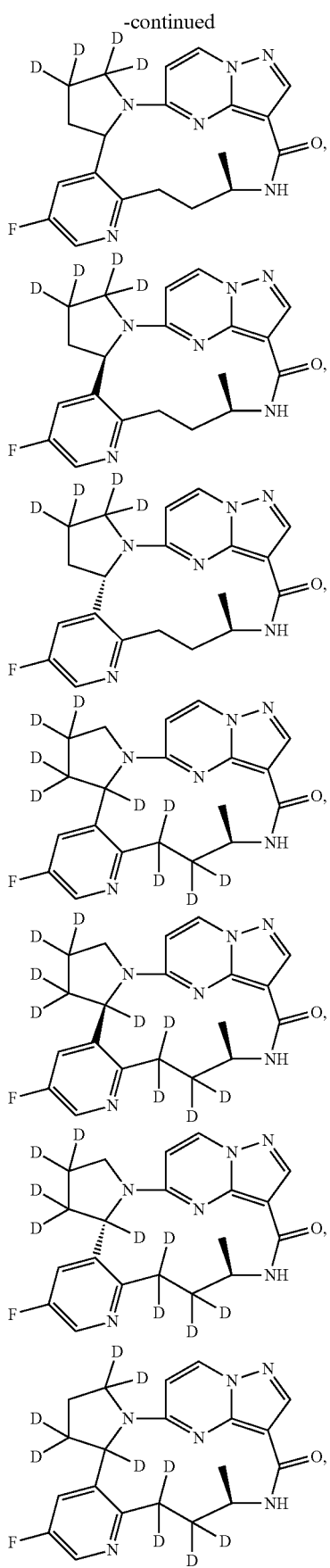
-continued
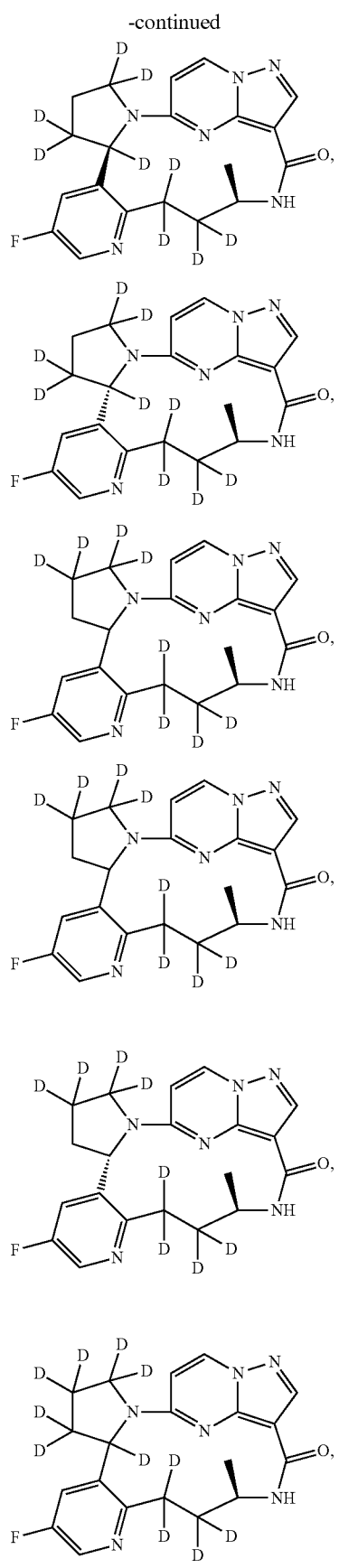

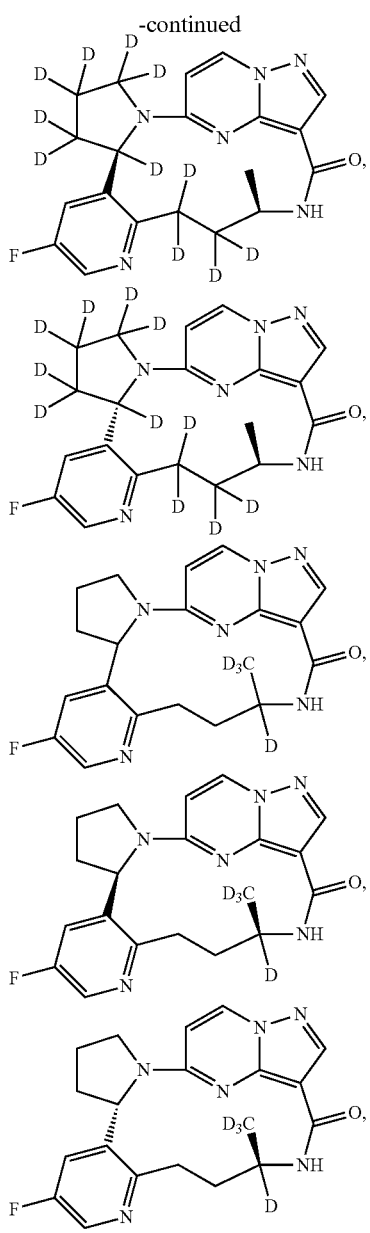
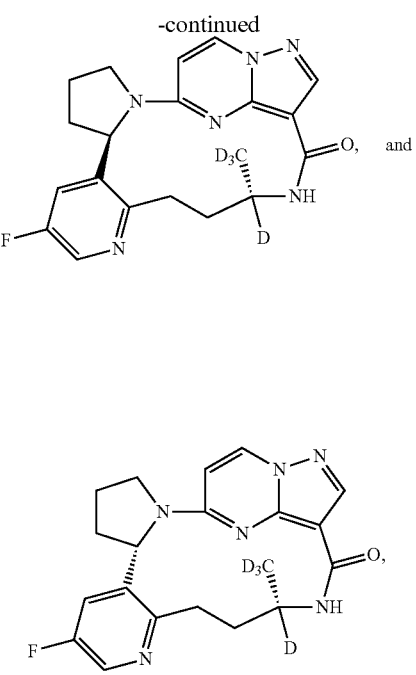

or a pharmaceutically acceptable salt, a hydrate or a solvate, a stereoisomer or an isotopic variant thereof.

11. A pharmaceutical composition comprising a pharmaceutically acceptable excipient and a compound according to claim 1, or a pharmaceutically acceptable salt, a hydrate or a solvate, a stereoisomer or an isotopic variant thereof.

12. A method for treating a disease mediated by wild-type and mutant Trk kinases in a subject, comprising administering to the subject a therapeutically effective amount of a compound of claim 1, or a pharmaceutically acceptable salt, a hydrate or a solvate, a stereoisomer or an isotopic variant thereof.

13. The method according to claim 12, wherein the disease is mediated by TrkA, TrkB or both.

14. The method according to claim 12, wherein the disease is selected from the group consisting of pain, cancers, inflammation, neurodegenerative diseases or trypanosomal infections.

\* \* \* \* \*